US011421219B2

(12) United States Patent
Wu et al.

(10) Patent No.: US 11,421,219 B2
(45) Date of Patent: Aug. 23, 2022

(54) METHODS AND COMPOSITIONS FOR TREATING LEBER CONGENITAL AMAUROSIS

(71) Applicant: The USA, as represented by the Secretary, Department of Health and Human Services, Bethesda, MD (US)

(72) Inventors: Zhijian Wu, Gaithersburg, MD (US); Anand Swaroop, Bethesda, MD (US); Suddhasil Mookherjee, Rockville, MD (US); Suja Hiriyanna, Boyds, MD (US)

(73) Assignee: THE USA, AS REPRESENTED BY THE SECRETARY, DHHS, Bethesda, MD (US)

( * ) Notice: Subject to any disclaimer, the term of this patent is extended or adjusted under 35 U.S.C. 154(b) by 530 days.

(21) Appl. No.: 16/423,962

(22) Filed: May 28, 2019

(65) Prior Publication Data

US 2020/0024593 A1 Jan. 23, 2020

Related U.S. Application Data

(62) Division of application No. 15/506,323, filed as application No. PCT/US2015/047209 on Aug. 27, 2015, now Pat. No. 10,351,844.

(60) Provisional application No. 62/042,703, filed on Aug. 27, 2014.

(51) Int. Cl.
*A61K 48/00* (2006.01)
*C12N 15/10* (2006.01)
*C07K 14/47* (2006.01)
*A61K 31/7088* (2006.01)
*C12N 9/22* (2006.01)
*C12N 15/113* (2010.01)
*C12N 15/86* (2006.01)

(52) U.S. Cl.
CPC ...... *C12N 15/1024* (2013.01); *A61K 31/7088* (2013.01); *C07K 14/4702* (2013.01); *C12N 9/22* (2013.01); *C12N 15/113* (2013.01); *C12N 15/86* (2013.01); *A61K 48/00* (2013.01); *A61K 48/005* (2013.01); *C12N 2310/10* (2013.01); *C12N 2750/14145* (2013.01)

(58) Field of Classification Search
None
See application file for complete search history.

(56) References Cited

U.S. PATENT DOCUMENTS

| | | |
|---|---|---|
| 2003/0104426 A1 | 6/2003 | Linsley |
| 2016/0022836 A1 | 1/2016 | Banfi et al. |
| 2016/0185832 A1* | 6/2016 | Drivas ............... C07K 14/47 514/20.8 |
| 2017/0275615 A1 | 9/2017 | Wu et al. |

OTHER PUBLICATIONS

Burnight et al (Gene Therapy 2014, vol. 21, pp. 662-672) (Year: 2014).*
Official Action for European Patent Application No. 15760025.5, dated Aug. 27, 2019 4 pages.
Database Geneseq [Online] Jun. 11, 2007, "Human CML marker gene, SEQ ID No. 158.", XP002750193, retrieved from EBI accession No. GSN: AEM95879.
Database EMBL [Online] May 17, 2012 "TSA: Macaca mulatta Mamu_551944 Mrna Sequence", xp002750194, retrieved from EBI accession No. EM_TSA:JV723973.
Database EMBL [Online] Nov. 30, 2000 (Nov. 30, 2000), "*Homo sapiens* CTCL tumor antigen se2-2 mRNA, partial cds.", XP002750195, retrieved from EBI accession No. EM_STD:AF273044.
Database Geneseq [Online] Oct. 23, 2014 (Oct. 23, 2014), "Human retinal dystrophy gene CEP290, SEQ ID:304.", XP002750198, retrieved from EBI accession No. GSN: BBM85064.
L.M. Baye et al: "The N-terminal region of centrosomal protein 290 (CEP290) restores vision in a zebrafish model of human blindness", Human Molecular Genetics, vol. 20, No. 8, Apr. 15, 2011 (Apr. 15, 2011), pp. 1467-1477.
Boye Shannon et al: "Natural History of Cone Disease in the Murine Model of Leber Congenital Amaurosis Due to CEP290 Mutation: Determining the Timing and Expectation of Therapy", PLOS ONE, vol. 9, No. 3, E92928, Mar. 2014 (Mar. 2014), pp. 1-12, XP002750196, p. 10.
Gao et al. "Novel adeno-associated viruses from rhesus monkeys as vectors for human gene therapy," PNAS, Sep. 2002, vol. 99, No. 18, pp. 11854-11859.
International Search Report and Written Opinion prepared by the European Patent Office dated Nov. 4, 2015, for International Application No. PCT/US2015/047209.
Official Action for Canada Patent Application No. 2,959,540, dated Jul. 27, 2017 3 pages.
Official Action for Canada Patent Application No. 2,959,540, dated May 2, 2018 3 pages.
Official Action for Canada Patent Application No. 2,959,540, dated Dec. 11, 2018 3 pages.
Official Action for European Patent Application No. 15760025.5, dated Jan. 4, 2018 3 pages.
Official Action for European Patent Application No. 15760025.5, dated Apr. 4, 2019 5 pages.
Official Action for U.S. Appl. No. 15/506,323, dated Dec. 14, 2017 7 pages Restriction Requirement.

(Continued)

*Primary Examiner* — Celine X Qian
(74) *Attorney, Agent, or Firm* — McBee Moore & Vanik IP, LLC

(57) ABSTRACT

Expression vectors, viral particles and therapeutic methods of using such constructs to improve the visual function of a patient suffering from diseases of the eye, resulting from failure to produce a specific protein in the eye, or the production of a non-functional protein in the eye, particularly Leber Congenital Amaurosis (LCA) and CEP290-related LCA.

11 Claims, 6 Drawing Sheets

Specification includes a Sequence Listing.

(56) References Cited

OTHER PUBLICATIONS

Official Action for U.S. Appl. No. 15/506,323, dated May 31, 2018 12 pages.
Official Action for U.S. Appl. No. 15/506,323, dated Oct. 19, 2018 10 pages.
Notice of Allowance for U.S. Appl. No. 15/506,323, dated Apr. 3, 2019 8 pages.

* cited by examiner

SEQUENCE LISTING

<160> NUMBER OF SEQ ID NOS: 45

<210> SEQ ID NO 1
<211> LENGTH: 7440
<212> TYPE: DNA
<213> ORGANISM: Mus musculus

<400> SEQUENCE: 1

```
atgccaccta atataaagtg gaaagaatta atcaaagttg atccagatga cctgccacgg      60
caagaagagt tagcagataa attattgata tctttatcca aggtggaagt aaatgaacta     120
aaaaatgaag accaagaaaa catgatacat ctattcagaa ttacccagtc tctaatgaag     180
atgaaagccc aggaagtaga gctcgctttg gaagaagttg aaaaggctgg agaagaacaa     240
gcaaaatttg aaaatcaatt aaagacaaaa gtaatgaaac tggaaaatga actggagatg     300
gctcagcagt ctgcagggggg acgtgacact cggttttttac gtgacgaaat tcgccaactt     360
gagaagcagc tggaacaaaa agatagagaa ttagaggata tggaaaaaga attggataaa     420
gaaaagaagg ttaatgaaca attggctctt cgaaatgagg aggcagaaaa tgaaaacagc     480
aaattaagaa gagagaacaa acgtctaaag aaaaagaatg agcagcttcg gcaggacatt     540
attgactacc agaaacaaat agattcacag aaagaatcac ttctgtcaag gagaggagaa     600
```

-continued

```
gacagtgact accgatcaca gttgtctaaa aagaactatg aacttgttca atatctggac    660
gaaatacaga ccttaacaga agctaatgag aagattgaag ttcagaacca agaaatgagg    720
aaaaacctgg aagagtctgt gcaggagatg agaagatga ctgatgagta caacaggatg     780
aaagcgcttg tgcatcagtc ggatgctgtc atggaccaga tcaagaagga gaatgagcac    840
tatcgcctgc aagttcgaga gctcacggat cttctgaagg cgaaggatga agaggacgat    900
ccagtcatga tggctgttaa cgcaaaagtg gaagagtgga agttaatttt gtcttctaaa    960
gatgatgaaa tcattgaata tcagcaaatg ctacagagtc tgagagggaa acttaaaaat   1020
gcccaacttg atgcagacaa aagtaacatc atggctctga acagggtat ccaggagcga    1080 gacagtcaaa ttaagatgct tactgagcaa gtagaacagt atacgaaaga aatggaaaaa   1140
aatacgttta ttattgaaga tttgaaaaat gaactccaaa aagacaaagg tacttcaaac   1200 tttatcagc agactcatta tatgaaaatt cactcaaaag tacaattttt agaagagaaa    1260 acaaagagg ccgagagaat agctgagctg gctgaggctg atgccaggga aaggacaaa     1320 gaattggttg aggctctgaa gagattaaaa gattatgaat ctggagtata tggcttagaa   1380
gatgctgtta tcgaaataaa gaattgtaaa gcccaaatta aataagaga tggagagatg    1440 gaagtgttga ccaaggagat caataagctt gagatgaaga tcaatgacat ccttgatgaa   1500
aacgaagccc ttagagagcg ggctggcctt gaacccaaga caatgattga tttgactgaa   1560
tttagaaaca gcaaacggtt aaagcagcaa cagtacagag ctgagaacca ggttcttttg   1620
aaagagatcg aaagtctaga ggaggagcgt cttgacttga aaagaaagat tcgtcaaatg   1680
gctcaagaaa gaggcaaaag gaacgcagcc tcaggattaa ccattgacga cttgaactta   1740
tctgaaacct ttctcatga aaataaaata aaggaagaa aactaaattt tatgagcctc      1800
aataatatga atgaaacaca atcaaagaat gagtttcttt caagagaatt ggctgaaaag   1860
gaaaaagatt tagaaagaag taggacagta attgctaaat tccagagtaa actaaaagaa   1920
ttagtcgaag aaaataagca acttgaagaa ggtatgaaag aaattttgca agctattaag   1980
gacatgccga aggattctga tgtgaaagga ggtgaaacat ctttaatcat cccgagtctt   2040
gaaagactgg ttaacgctat ggaatcaaag aatgcagaag gaatcttcga tgccagcttg   2100
catctaaaag cccaagttga ccaacttaca ggaaggaatg aagaattaag gcaagaactc   2160
aggcaatctc ggaaagaggc tgtaaattat tcacagcagt tggtaaaagc aaacttaaag   2220
attgaccacc ttgagaagga aactgacctt ctacgtcagt ctgcaggctc caatgtagta   2280
tacaaaggca tagacttacc cgatgggata gcaccatcca gtgcctatat catcaattct   2340
cagaatgaat acttaataca tcttttgcag gaactagaca ataaagaaaa gaaattaaaa   2400
catttagaag attcccttga agattataac agaaagtttg cagtgattcg tcatcaacaa   2460
agtttattat ataaagaata cctaagtgaa aaggatattt ggaaaacaga ctctgagatg   2520
ataagagagg agaagagaaa actggaagat caagctgagc aggatgctgt gaaagtaaaa   2580
gagtacaaca atttgctcag tgctcttcag atggattcga acgagatgaa gaaaatgctc   2640
tcagaaaaca gtaggaaaat caccgttctg caagtgaacg agaagtccct catccggcag   2700
tacaccacct tagtggagat ggagcggcac ctgagaaagg aaaacgggaa acacaggaat   2760
gacgtcatag ccatggaggc cgaagtcact gaaaaacttg aagtttgca aagattcaag    2820 gaaatggcca tcttcaagat tgcagctctt cagaaggtta tagataatag tgtttctttg   2880
tctgaattag aactagccaa taacagtac aatgagctga ctactaagta cagggacatc    2940
ttgcagaaag ataatatgct tgttcaaaga acaagtaact tagaacacct ggagtgtgag   3000
```

```
aatgcatcgc taaaagaaca gatggaggct atcagtaaag agctggagat tacaaaggaa    3060
aaactccata ccattgaaca ggcctgggaa caagaaacga agttaggaaa tgactcaaac    3120
atggataagg ctaagaaatc aatgacaaac agtgacattg tttctatttc aaagaaaatc    3180
actgtgttgg agatgaagga attaaatgaa aggcagaggg ctgaacactg tcagaaaatg    3240
tatgagcact taaggacttc attaaagcaa atggaagaac gtaattttga attggaaacc    3300
aagttcactg agcttactaa aatcaacctg gatgcacaaa aggtggagca gatgttgaga    3360
gacgaattag ctgatagtgt gaccaaggca gtaagtgatg ctgaccgaca gcggattcta    3420
gaactagaga agagtgaagt ggagctcaaa gttgaagtgt ccaagctgag agagatttca    3480
gatattgcca aaagacaagt tgatttttg aattcgcaac aacagtccag ggaaaaggaa    3540
gtggaatccc tcagaacgca gctgctggac ttccaggcac aatctgacga aaaggctcta    3600
attgccaaat tgcaccaaca tgttgtctct cttcaaatta gtgaggccac tgccctcggt    3660
aagttagagt cagttacgtc caaactccag aagatggaag cctacaattt gcgcttagaa    3720
cagaaactgg atgaaaaaga gcaggcgctc tactatgctc gtttggaagg tagaaacaga    3780
gcaaaacacc tgcgccaaac cattcagtcg cttcgaagac agttcagtgg agctctaccc    3840
ttagcacagc aggaaaagtt ctccaaaacg atgattcagt tgcaaaatga caaacttaag    3900
ataatgcaag aaatgaagaa ttcgcaacag gaacacagaa atatgaaaaa caaaacactg    3960
gagttggaat taaaattaaa aggcttagaa gaattgatca gtactttaaa ggatgccagg    4020
ggagcccaga aggtaatcaa ttggcatgtg aaaatagaag aacttcgcct ccaagaactt    4080
aagctaaata gagaactagt caagggtaaa gaagaaatca atatttgaa taatatcatc    4140 tctgaatatg agcatacaat caacagtcta gaggaagaaa ttgttcagca aagcaagttc    4200
catgaagaaa gacagatggc ttgggatcaa agagaagttg agctggaacg ccagttagac    4260 attttgatc atcagcaaaa tgaaatactc agtgcagcac aaaagtttga agactctaca    4320
ggatcaatgc cagaccccag cttgcctctt ccaaaccaac ttgaaattgc tctaagaaaa    4380
attaaggaga atattcaagt aattcttaaa acacaagcaa cttgcaagtc actagaagag    4440
aaactaaaag aaaaagaatc tgctttacgg ttggcagagc aaaatattct gtcaagagac    4500
aaagtaatca atgaactgag gcttcgattg cctgccacgg ctgatcgaga aaaacttata    4560
gctgagctag aaagaaaaga gctggagccg aaatctcatc acacaatgaa aattgcccac    4620
caaactattg ccaacatgca ggcaaggtta aatcacaagg aagaagtatt gaagaaatac    4680
cagcaccttc tggagaaggc cagagaggag caaagagaaa ttgttaagaa gcatgaggaa    4740
gaccttcatg ttcttcatca caaattagaa caacaggccg ataattcact caataaattc    4800
agacagacag ctcaggattt acttaagcag tctcctgctc cagttcccac caacaaacat    4860
ttcattcgtc tggccgagat ggagcagaca gtagcagaac aagatgactc tctgtcctca    4920
cttttgacca aactaaagaa agtatcaaaa gatttggaaa aacaaaaaga atcactgag    4980 ttaaaagtca gagagtttga aaataccaaa ctacggctcc aagaaactca tgccagtgag    5040
gtaaagaaag tgaaagcaga ggtagaggac ttaaggcatg ctctagccca agcacacaag    5100
gactcccaga gtttaaagtc tgaactccag gctcagaaag aagcaaactc cagagctcca    5160
acaaccacaa tgaggaatct tgtagacagg ctaaagagcc aactagcctt gaaagagaag    5220
caacaaaagg cacttagtcg agccctgttg gaacttcggt cggaaatgac agcagcagct    5280
gaggaacgta taatcgctgt aacttctcaa aaagaggcaa atctcaatgt tcaacaagtt    5340
```

| | |
|---|---|
| gttgagcgcc atactagaga gctaaagtca caaattgaag atttaaatga aaatctttta | 5400 |
| aaattgaaag aagctcttaa acaagtaag aacaaagaaa attcactagc tgatgattta | 5460 |
| aatgaattaa ataatgaact gcaaaaaaag caaaaagctt ataataaaat ccttagagag | 5520 |
| aaagatggaa ttgatcaaga aaatgatgaa ctgagaagac agattaaaag actgtccagt | 5580 |
| ggactgcaga gcaaaacttt gatagataac aagcaaagtt taatcgatga acttcaaaag | 5640 |
| aaagttaaaa aacttgaaag ccaactggaa agaaaggtgg atgacgtaga cataaagccg | 5700 |
| gtgaaggaaa agagtagtaa agaagaatta attaggtggg aagaaggtaa gaaatggcaa | 5760 |
| accaaagtag agggactacg aaacagacta aggagaagg aaggagaagc ccacggcctg | 5820 |
| gcaaagcagc tgaataccct aaaggaactt tttgccaaag ctgataaaga gaaacttact | 5880 |
| ttgcagaaga aactgaaaac aacaggaatg actgttgacc aggttttagg agtgcgagct | 5940 |
| ttggaatctg aaaagagtt ggaagagcta aaaagaaaa atctggacct agaaaatgac | 6000 |
| atattataca tgaggaccca gcaggctctt ccacgagatt ctgttgtgga agacttacat | 6060 |
| ttacaaaata aataccttca agaaaaactt catactttag aaaaaaaact ttcaaaggag | 6120 |
| aaatattctc agtctttgac ttcagaaata gagtcagatg atcactgtca aaaagaacaa | 6180 |
| gaacttcaga aggaaaattt gaagttgtca tctgaaaaca tcgagctgaa atttcaactt | 6240 |
| gaacaagcaa ataaagattt gccaagacta agaatcaag tgaaagattt gaaggaaatg | 6300 |
| tgtgaatttc ttaagaaagg aaaactggaa cttgagcgga agcttggtca ggtcagaggg | 6360 |
| gctggtagaa gtgggaagac aatcccagaa ctagaaaaaa ccattgggtt aatgaagaaa | 6420 |
| gtagttgaaa aagtccaaag agaaaatgaa caattgaaaa aggcatcagg aatactgact | 6480 |
| agtgaaaaaa tggctactat tgaggaagaa aatagaaact taaaggctga actagaaaag | 6540 |
| cttaaagctc actttggacg tcagttgagt atgcagtttg aatctaagaa caaaggtact | 6600 |
| gagaaaattg ttgccgaaaa tgaacggctt cggaaagaac ttaagaaaga aatagaagcc | 6660 |
| tctgagaaac tgcggatagc taagaacaac ttagagctgg tgaacgacaa gatggcagct | 6720 |
| caactcgaag aaactgggaa gagactacag tttgcagaaa gtagagcccc acagctggaa | 6780 |
| ggtgctgaca gcaagagctg gaagtcaatt gtggtctcaa gagtgtatga gaccaagatg | 6840 |
| aaagagcttg aaagtgacat tgccaaaaag aatcaaagta tcactgacct taaacagctt | 6900 |
| gtaagagaag caacagagag agaacagaaa gctaagaaat acactgaaga ccttgaacaa | 6960 |
| cagattgaga tcctcaaaaa tgttcctgaa ggtgccgaga cagagcaaga gcttatacgg | 7020 |
| gaactccagc ttcttagatt agccaataat cagatggata agaaagggc agaattaatc | 7080 |
| catcagatag aaattaacaa ggaccaaacc agagctgaca gtagcatacc tgattctgat | 7140 |
| caactaaagg aaaagataaa tgacctggag acacaactca gaaagttgga gctagaaaag | 7200 |
| caacattcga aggaggaagt taaaaagctg aaaaaagaac tggaaaattt tgatccttca | 7260 |
| tttttttgaag aaattgaaga cctgaagtat aattataagg aagaagtgaa aaagaatatc | 7320 |
| ctattagaag agaagctaaa aaaactgtcg aacagtttg gatttgaact gcctagtcct | 7380 |
| cttgctgctt ctgaacactc ggaagatgga gaaagtcctc atagtttccc tatttattag | 7440 |

<210> SEQ ID NO 2
<211> LENGTH: 2479
<212> TYPE: PRT
<213> ORGANISM: Mus musculus

<400> SEQUENCE: 2

Met Pro Pro Asn Ile Lys Trp Lys Glu Leu Ile Lys Val Asp Pro Asp

```
1               5                   10                  15
Asp Leu Pro Arg Gln Glu Glu Leu Ala Asp Lys Leu Leu Ile Ser Leu
            20                  25                  30

Ser Lys Val Glu Val Asn Glu Leu Lys Asn Glu Asp Gln Glu Asn Met
            35                  40                  45

Ile His Leu Phe Arg Ile Thr Gln Ser Leu Met Lys Met Lys Ala Gln
            50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
            85                  90                  95

Glu Leu Glu Met Ala Gln Gln Ser Ala Gly Gly Arg Asp Thr Arg Phe
            100                 105                 110

Leu Arg Asp Glu Ile Arg Gln Leu Glu Lys Gln Leu Glu Gln Lys Asp
            115                 120                 125

Arg Glu Leu Glu Asp Met Glu Lys Glu Leu Asp Lys Glu Lys Lys Val
            130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Asn Glu Gln Leu
            165                 170                 175

Arg Gln Asp Ile Ile Asp Tyr Gln Lys Gln Ile Asp Ser Gln Lys Glu
            180                 185                 190

Ser Leu Leu Ser Arg Arg Gly Glu Asp Ser Asp Tyr Arg Ser Gln Leu
            195                 200                 205

Ser Lys Lys Asn Tyr Glu Leu Val Gln Tyr Leu Asp Glu Ile Gln Thr
            210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
            245                 250                 255

Tyr Asn Arg Met Lys Ala Leu Val His Gln Ser Asp Ala Val Met Asp
            260                 265                 270

Gln Ile Lys Lys Glu Asn Glu His Tyr Arg Leu Gln Val Arg Glu Leu
            275                 280                 285

Thr Asp Leu Leu Lys Ala Lys Asp Glu Asp Asp Pro Val Met Met
            290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu Gln Ser Leu Arg Gly
            325                 330                 335

Lys Leu Lys Asn Ala Gln Leu Asp Ala Asp Lys Ser Asn Ile Met Ala
            340                 345                 350

Leu Lys Gln Gly Ile Gln Glu Arg Asp Ser Gln Ile Lys Met Leu Thr
            355                 360                 365

Glu Gln Val Glu Gln Tyr Thr Lys Glu Met Glu Lys Asn Thr Phe Ile
            370                 375                 380

Ile Glu Asp Leu Lys Asn Glu Leu Gln Lys Asp Lys Gly Thr Ser Asn
385                 390                 395                 400

Phe Tyr Gln Gln Thr His Tyr Met Lys Ile His Ser Lys Val Gln Ile
            405                 410                 415

Leu Glu Glu Lys Thr Lys Glu Ala Glu Arg Ile Ala Glu Leu Ala Glu
            420                 425                 430
```

```
Ala Asp Ala Arg Glu Lys Asp Lys Glu Leu Val Glu Ala Leu Lys Arg
        435                 440                 445

Leu Lys Asp Tyr Glu Ser Gly Val Tyr Gly Leu Glu Asp Ala Val Ile
    450                 455                 460

Glu Ile Lys Asn Cys Lys Ala Gln Ile Lys Ile Arg Asp Gly Glu Met
465                 470                 475                 480

Glu Val Leu Thr Lys Glu Ile Asn Lys Leu Glu Met Lys Ile Asn Asp
                485                 490                 495

Ile Leu Asp Glu Asn Glu Ala Leu Arg Glu Arg Ala Gly Leu Glu Pro
            500                 505                 510

Lys Thr Met Ile Asp Leu Thr Glu Phe Arg Asn Ser Lys Arg Leu Lys
        515                 520                 525

Gln Gln Gln Tyr Arg Ala Glu Asn Gln Val Leu Leu Lys Glu Ile Glu
    530                 535                 540

Ser Leu Glu Glu Glu Arg Leu Asp Leu Lys Arg Lys Ile Arg Gln Met
545                 550                 555                 560

Ala Gln Glu Arg Gly Lys Arg Asn Ala Ala Ser Gly Leu Thr Ile Asp
                565                 570                 575

Asp Leu Asn Leu Ser Glu Thr Phe Ser His Glu Asn Lys Ile Glu Gly
            580                 585                 590

Arg Lys Leu Asn Phe Met Ser Leu Asn Asn Met Asn Glu Thr Gln Ser
        595                 600                 605

Lys Asn Glu Phe Leu Ser Arg Glu Leu Ala Glu Lys Glu Lys Asp Leu
    610                 615                 620

Glu Arg Ser Arg Thr Val Ile Ala Lys Phe Gln Ser Lys Leu Lys Glu
625                 630                 635                 640

Leu Val Glu Glu Asn Lys Gln Leu Glu Glu Gly Met Lys Glu Ile Leu
                645                 650                 655

Gln Ala Ile Lys Asp Met Pro Lys Asp Ser Asp Val Lys Gly Gly Glu
            660                 665                 670

Thr Ser Leu Ile Ile Pro Ser Leu Glu Arg Leu Val Asn Ala Met Glu
        675                 680                 685

Ser Lys Asn Ala Glu Gly Ile Phe Asp Ala Ser Leu His Leu Lys Ala
    690                 695                 700

Gln Val Asp Gln Leu Thr Gly Arg Asn Glu Glu Leu Arg Gln Glu Leu
705                 710                 715                 720

Arg Gln Ser Arg Lys Glu Ala Val Asn Tyr Ser Gln Leu Val Lys
                725                 730                 735

Ala Asn Leu Lys Ile Asp His Leu Glu Lys Glu Thr Asp Leu Leu Arg
            740                 745                 750

Gln Ser Ala Gly Ser Asn Val Val Tyr Lys Gly Ile Asp Leu Pro Asp
        755                 760                 765

Gly Ile Ala Pro Ser Ser Ala Tyr Ile Ile Asn Ser Gln Asn Glu Tyr
    770                 775                 780

Leu Ile His Leu Leu Gln Glu Leu Asp Asn Lys Glu Lys Lys Leu Lys
785                 790                 795                 800

His Leu Glu Asp Ser Leu Glu Asp Tyr Asn Arg Lys Phe Ala Val Ile
                805                 810                 815

Arg His Gln Gln Ser Leu Leu Tyr Lys Glu Tyr Leu Ser Glu Lys Asp
            820                 825                 830

Ile Trp Lys Thr Asp Ser Glu Met Ile Arg Glu Glu Lys Arg Lys Leu
        835                 840                 845
```

-continued

```
Glu Asp Gln Ala Glu Gln Asp Ala Val Lys Val Lys Glu Tyr Asn Asn
850                 855                 860

Leu Leu Ser Ala Leu Gln Met Asp Ser Asn Glu Met Lys Lys Met Leu
865                 870                 875                 880

Ser Glu Asn Ser Arg Lys Ile Thr Val Leu Gln Val Asn Glu Lys Ser
                885                 890                 895

Leu Ile Arg Gln Tyr Thr Thr Leu Val Glu Met Glu Arg His Leu Arg
                900                 905                 910

Lys Glu Asn Gly Lys His Arg Asn Asp Val Ile Ala Met Glu Ala Glu
                915                 920                 925

Val Thr Glu Lys Leu Gly Ser Leu Gln Arg Phe Lys Glu Met Ala Ile
930                 935                 940

Phe Lys Ile Ala Ala Leu Gln Lys Val Ile Asp Asn Ser Val Ser Leu
945                 950                 955                 960

Ser Glu Leu Glu Leu Ala Asn Lys Gln Tyr Asn Glu Leu Thr Thr Lys
                965                 970                 975

Tyr Arg Asp Ile Leu Gln Lys Asp Asn Met Leu Val Gln Arg Thr Ser
                980                 985                 990

Asn Leu Glu His Leu Glu Cys Glu Asn Ala Ser Leu Lys Glu Gln Met
                995                 1000                1005

Glu Ala Ile Ser Lys Glu Leu Glu Ile Thr Lys Glu Lys Leu His
1010                1015                1020

Thr Ile Glu Gln Ala Trp Glu Gln Thr Lys Leu Gly Asn Asp
1025                1030                1035

Ser Asn Met Asp Lys Ala Lys Lys Ser Met Thr Asn Ser Asp Ile
1040                1045                1050

Val Ser Ile Ser Lys Lys Ile Thr Val Leu Glu Met Lys Glu Leu
1055                1060                1065

Asn Glu Arg Gln Arg Ala Glu His Cys Gln Lys Met Tyr Glu His
1070                1075                1080

Leu Arg Thr Ser Leu Lys Gln Met Glu Glu Arg Asn Phe Glu Leu
1085                1090                1095

Glu Thr Lys Phe Thr Glu Leu Thr Lys Ile Asn Leu Asp Ala Gln
1100                1105                1110

Lys Val Glu Gln Met Leu Arg Asp Glu Leu Ala Asp Ser Val Thr
1115                1120                1125

Lys Ala Val Ser Asp Ala Asp Arg Gln Arg Ile Leu Glu Leu Glu
1130                1135                1140

Lys Ser Glu Val Glu Leu Lys Val Glu Val Ser Lys Leu Arg Glu
1145                1150                1155

Ile Ser Asp Ile Ala Lys Arg Gln Val Asp Phe Leu Asn Ser Gln
1160                1165                1170

Gln Gln Ser Arg Glu Lys Glu Val Glu Ser Leu Arg Thr Gln Leu
1175                1180                1185

Leu Asp Phe Gln Ala Gln Ser Asp Glu Lys Ala Leu Ile Ala Lys
1190                1195                1200

Leu His Gln His Val Val Ser Leu Gln Ile Ser Glu Ala Thr Ala
1205                1210                1215

Leu Gly Lys Leu Glu Ser Val Thr Ser Lys Leu Gln Lys Met Glu
1220                1225                1230

Ala Tyr Asn Leu Arg Leu Glu Gln Lys Leu Asp Glu Lys Glu Gln
1235                1240                1245

Ala Leu Tyr Tyr Ala Arg Leu Glu Gly Arg Asn Arg Ala Lys His
```

```
              1250                1255                1260
Leu Arg Gln Thr Ile Gln Ser Leu Arg Arg Gln Phe Ser Gly Ala
         1265                1270                1275
Leu Pro Leu Ala Gln Gln Glu Lys Phe Ser Lys Thr Met Ile Gln
         1280                1285                1290
Leu Gln Asn Asp Lys Leu Lys Ile Met Gln Glu Met Lys Asn Ser
         1295                1300                1305
Gln Gln Glu His Arg Asn Met Glu Asn Lys Thr Leu Glu Leu Glu
         1310                1315                1320
Leu Lys Leu Lys Gly Leu Glu Glu Leu Ile Ser Thr Leu Lys Asp
         1325                1330                1335
Ala Arg Gly Ala Gln Lys Val Ile Asn Trp His Val Lys Ile Glu
         1340                1345                1350
Glu Leu Arg Leu Gln Glu Leu Lys Leu Asn Arg Glu Leu Val Lys
         1355                1360                1365
Gly Lys Glu Glu Ile Lys Tyr Leu Asn Asn Ile Ile Ser Glu Tyr
         1370                1375                1380
Glu His Thr Ile Asn Ser Leu Glu Glu Glu Ile Val Gln Gln Ser
         1385                1390                1395
Lys Phe His Glu Glu Arg Gln Met Ala Trp Asp Gln Arg Glu Val
         1400                1405                1410
Glu Leu Glu Arg Gln Leu Asp Ile Phe Asp His Gln Gln Asn Glu
         1415                1420                1425
Ile Leu Ser Ala Ala Gln Lys Phe Glu Asp Ser Thr Gly Ser Met
         1430                1435                1440
Pro Asp Pro Ser Leu Pro Leu Pro Asn Gln Leu Glu Ile Ala Leu
         1445                1450                1455
Arg Lys Ile Lys Glu Asn Ile Gln Val Ile Leu Lys Thr Gln Ala
         1460                1465                1470
Thr Cys Lys Ser Leu Glu Glu Lys Leu Lys Glu Lys Glu Ser Ala
         1475                1480                1485
Leu Arg Leu Ala Glu Gln Asn Ile Leu Ser Arg Asp Lys Val Ile
         1490                1495                1500
Asn Glu Leu Arg Leu Arg Leu Pro Ala Thr Ala Asp Arg Glu Lys
         1505                1510                1515
Leu Ile Ala Glu Leu Glu Arg Lys Glu Leu Glu Pro Lys Ser His
         1520                1525                1530
His Thr Met Lys Ile Ala His Gln Thr Ile Ala Asn Met Gln Ala
         1535                1540                1545
Arg Leu Asn His Lys Glu Glu Val Leu Lys Lys Tyr Gln His Leu
         1550                1555                1560
Leu Glu Lys Ala Arg Glu Glu Gln Arg Glu Ile Val Lys Lys His
         1565                1570                1575
Glu Glu Asp Leu His Val Leu His His Lys Leu Glu Gln Gln Ala
         1580                1585                1590
Asp Asn Ser Leu Asn Lys Phe Arg Gln Thr Ala Gln Asp Leu Leu
         1595                1600                1605
Lys Gln Ser Pro Ala Pro Val Pro Thr Asn Lys His Phe Ile Arg
         1610                1615                1620
Leu Ala Glu Met Glu Gln Thr Val Ala Glu Gln Asp Asp Ser Leu
         1625                1630                1635
Ser Ser Leu Leu Thr Lys Leu Lys Lys Val Ser Lys Asp Leu Glu
         1640                1645                1650
```

```
Lys Gln Lys Glu Ile Thr Glu Leu Lys Val Arg Glu Phe Glu Asn
    1655                1660                1665

Thr Lys Leu Arg Leu Gln Glu Thr His Ala Ser Glu Val Lys Lys
    1670                1675                1680

Val Lys Ala Glu Val Glu Asp Leu Arg His Ala Leu Ala Gln Ala
    1685                1690                1695

His Lys Asp Ser Gln Ser Leu Lys Ser Glu Leu Gln Ala Gln Lys
    1700                1705                1710

Glu Ala Asn Ser Arg Ala Pro Thr Thr Thr Met Arg Asn Leu Val
    1715                1720                1725

Asp Arg Leu Lys Ser Gln Leu Ala Leu Lys Glu Lys Gln Gln Lys
    1730                1735                1740

Ala Leu Ser Arg Ala Leu Leu Glu Leu Arg Ser Glu Met Thr Ala
    1745                1750                1755

Ala Ala Glu Glu Arg Ile Ile Ala Val Thr Ser Gln Lys Glu Ala
    1760                1765                1770

Asn Leu Asn Val Gln Gln Val Val Glu Arg His Thr Arg Glu Leu
    1775                1780                1785

Lys Ser Gln Ile Glu Asp Leu Asn Glu Asn Leu Leu Lys Leu Lys
    1790                1795                1800

Glu Ala Leu Lys Thr Ser Lys Asn Lys Glu Asn Ser Leu Ala Asp
    1805                1810                1815

Asp Leu Asn Glu Leu Asn Asn Glu Leu Gln Lys Lys Gln Lys Ala
    1820                1825                1830

Tyr Asn Lys Ile Leu Arg Glu Lys Asp Gly Ile Asp Gln Glu Asn
    1835                1840                1845

Asp Glu Leu Arg Arg Gln Ile Lys Arg Leu Ser Ser Gly Leu Gln
    1850                1855                1860

Ser Lys Thr Leu Ile Asp Asn Lys Gln Ser Leu Ile Asp Glu Leu
    1865                1870                1875

Gln Lys Lys Val Lys Lys Leu Glu Ser Gln Leu Glu Arg Lys Val
    1880                1885                1890

Asp Asp Val Asp Ile Lys Pro Val Lys Glu Lys Ser Ser Lys Glu
    1895                1900                1905

Glu Leu Ile Arg Trp Glu Glu Gly Lys Lys Trp Gln Thr Lys Val
    1910                1915                1920

Glu Gly Leu Arg Asn Arg Leu Lys Glu Lys Gly Glu Ala His
    1925                1930                1935

Gly Leu Ala Lys Gln Leu Asn Thr Leu Lys Glu Leu Phe Ala Lys
    1940                1945                1950

Ala Asp Lys Glu Lys Leu Thr Leu Gln Lys Lys Leu Lys Thr Thr
    1955                1960                1965

Gly Met Thr Val Asp Gln Val Leu Gly Val Arg Ala Leu Glu Ser
    1970                1975                1980

Glu Lys Glu Leu Glu Glu Leu Lys Lys Lys Asn Leu Asp Leu Glu
    1985                1990                1995

Asn Asp Ile Leu Tyr Met Arg Thr Gln Gln Ala Leu Pro Arg Asp
    2000                2005                2010

Ser Val Val Glu Asp Leu His Leu Gln Asn Lys Tyr Leu Gln Glu
    2015                2020                2025

Lys Leu His Thr Leu Glu Lys Lys Leu Ser Lys Glu Lys Tyr Ser
    2030                2035                2040
```

```
Gln Ser Leu Thr Ser Glu Ile Glu Ser Asp Asp His Cys Gln Lys
2045                2050                2055

Glu Gln Glu Leu Gln Lys Glu Asn Leu Lys Leu Ser Ser Glu Asn
2060                2065                2070

Ile Glu Leu Lys Phe Gln Leu Glu Gln Ala Asn Lys Asp Leu Pro
2075                2080                2085

Arg Leu Lys Asn Gln Val Lys Asp Leu Lys Glu Met Cys Glu Phe
2090                2095                2100

Leu Lys Lys Gly Lys Leu Glu Leu Glu Arg Lys Leu Gly Gln Val
2105                2110                2115

Arg Gly Ala Gly Arg Ser Gly Lys Thr Ile Pro Glu Leu Glu Lys
2120                2125                2130

Thr Ile Gly Leu Met Lys Lys Val Val Glu Lys Val Gln Arg Glu
2135                2140                2145

Asn Glu Gln Leu Lys Lys Ala Ser Gly Ile Leu Thr Ser Glu Lys
2150                2155                2160

Met Ala Thr Ile Glu Glu Glu Asn Arg Asn Leu Lys Ala Glu Leu
2165                2170                2175

Glu Lys Leu Lys Ala His Phe Gly Arg Gln Leu Ser Met Gln Phe
2180                2185                2190

Glu Ser Lys Asn Lys Gly Thr Glu Lys Ile Val Ala Glu Asn Glu
2195                2200                2205

Arg Leu Arg Lys Glu Leu Lys Lys Glu Ile Glu Ala Ser Glu Lys
2210                2215                2220

Leu Arg Ile Ala Lys Asn Asn Leu Glu Leu Val Asn Asp Lys Met
2225                2230                2235

Ala Ala Gln Leu Glu Glu Thr Gly Lys Arg Leu Gln Phe Ala Glu
2240                2245                2250

Ser Arg Ala Pro Gln Leu Glu Gly Ala Asp Ser Lys Ser Trp Lys
2255                2260                2265

Ser Ile Val Val Ser Arg Val Tyr Glu Thr Lys Met Lys Glu Leu
2270                2275                2280

Glu Ser Asp Ile Ala Lys Lys Asn Gln Ser Ile Thr Asp Leu Lys
2285                2290                2295

Gln Leu Val Arg Glu Ala Thr Glu Arg Glu Gln Lys Ala Lys Lys
2300                2305                2310

Tyr Thr Glu Asp Leu Glu Gln Gln Ile Glu Ile Leu Lys Asn Val
2315                2320                2325

Pro Glu Gly Ala Glu Thr Glu Gln Glu Leu Ile Arg Glu Leu Gln
2330                2335                2340

Leu Leu Arg Leu Ala Asn Asn Gln Met Asp Lys Glu Arg Ala Glu
2345                2350                2355

Leu Ile His Gln Ile Glu Ile Asn Lys Asp Gln Thr Arg Ala Asp
2360                2365                2370

Ser Ser Ile Pro Asp Ser Asp Gln Leu Lys Glu Lys Ile Asn Asp
2375                2380                2385

Leu Glu Thr Gln Leu Arg Lys Leu Glu Leu Glu Lys Gln His Ser
2390                2395                2400

Lys Glu Glu Val Lys Lys Leu Lys Lys Glu Leu Glu Asn Phe Asp
2405                2410                2415

Pro Ser Phe Phe Glu Glu Ile Glu Asp Leu Lys Tyr Asn Tyr Lys
2420                2425                2430

Glu Glu Val Lys Lys Asn Ile Leu Leu Glu Glu Lys Leu Lys Lys
```

|  | 2435 | | | 2440 | | | 2445 | | |
|---|---|---|---|---|---|---|---|---|---|

Leu Ser Glu Gln Phe Gly Phe Glu Leu Pro Ser Pro Leu Ala Ala
    2450            2455            2460

Ser Glu His Ser Glu Asp Gly Glu Ser Pro His Ser Phe Pro Ile
    2465            2470            2475

Tyr

<210> SEQ ID NO 3
<211> LENGTH: 7440
<212> TYPE: DNA
<213> ORGANISM: Mus musculus

<400> SEQUENCE: 3

| ctaataaata gggaaactat gaggactttc tccatcttcc gagtgttcag aagcagcaag | 60 |
|---|---|
| aggactaggc agttcaaatc caaactgttc cgacagtttt tttagcttct cttctaatag | 120 |
| gatattcttt ttcacttctt ccttataatt atacttcagg tcttcaattt cttcaaaaaa | 180 |
| tgaaggatca aaattttcca gttcttttt cagcttttta acttcctcct tcgaatgttg | 240 |
| cttttctagc tccaactttc tgagttgtgt ctccaggtca tttatctttt cctttagttg | 300 |
| atcagaatca ggtatgctac tgtcagctct ggtttggtcc ttgttaattt ctatctgatg | 360 |
| gattaattct gccctttctt tatccatctg attattggct aatctaagaa gctggagttc | 420 |
| ccgtataagc tcttgctctg tctcggcacc tcaggaaaca ttttttgagga tctcaatctg | 480 |
| ttgttcaagg tcttcagtgt atttcttagc tttctgttct ctctctgttg cttctcttac | 540 |
| aagctgttta aggtcagtga tactttgatt cttttggca atgtcacttt caagctcttt | 600 |
| catcttggtc tcatacactc ttgagaccac aattgacttc cagctcttgc tgtcagcacc | 660 |
| ttccagctgt ggggctctac tttctgcaaa ctgtagtctc ttcccagttt cttcgagttg | 720 |
| agctgccatc ttgtcgttca ccagctctaa gttgttctta gctatccgca gtttctcaga | 780 |
| ggcttctatt tcttcttaa gttctttccg aagccgttca ttttcggcaa caattttctc | 840 |
| agtacctttg ttcttagatt caaactgcat actcaactga cgtccaaagt gagctttaag | 900 |
| cttttctagt tcagccttta agtttctatt ttcttcctca atagtagcca ttttttcact | 960 |
| agtcagtatt cctgatgcct ttttcaattg ttcattttct ctttggactt tttcaactac | 1020 |
| tttcttcatt aacccaatgg ttttttctag ttctgggatt gtcttcccac ttctaccagc | 1080 |
| ccctctgacc tgaccaagct tccgctcaag ttccagtttt cctttcttaa gaaattcaca | 1140 |
| catttccttc aaatctttca cttgattctt tagtcttggc aaatctttat ttgcttgttc | 1200 |
| aagttgaaat ttcagctcga tgttttcaga tgacaacttc aaattttcct tctgaagttc | 1260 |
| ttgttctttt tgacagtgat catctgactc tatttctgaa gtcaaagact gagaatattt | 1320 |
| ctcctttgaa agtttttttt ctaaagtatg aagttttct tgaaggtatt tattttgtaa | 1380 |
| atgtaagtct tccacaacag aatctcgtgg aagagcctgc tgggtcctca tgtataatat | 1440 |
| gtcattttct aggtccagat ttttctttt tagctcttcc aactctttt cagattccaa | 1500 |
| agctcgcact cctaaaacct ggtcaacagt cattcctgtt gttttcagtt cttctgcaa | 1560 |
| agtaagtttc tctttatcag ctttggcaaa aagttccttt aaggtattca gctgctttgc | 1620 |
| caggccgtgg gcttctcctt cctctccctt tagtctgttt cgtagtccct ctactttggt | 1680 |
| ttgccatttc ttaccttctt cccacctaat taattcttct ttactactct tttccttcac | 1740 |
| cggctttatg tctacgtcat ccacctttct ttccagttgg ctttcaagtt ttttaacttt | 1800 |
| cttttgaagt tcatcgatta aactttgctt gttatctatc aaagttttgc tctgcagtcc | 1860 |

```
actggacagt cttttaatct gtcttctcag ttcatcattt tcttgatcaa ttccatcttt   1920
ctctctaagg attttattat aagcttttg cttttttgc agttcattat ttaattcatt    1980
taaatcatca gctagtgaat tttctttgtt cttacttgtt ttaagagctt ctttcaattt   2040
taaaagattt tcatttaaat cttcaatttg tgactttagc tctctagtat ggcgctcaac   2100
aacttgttga acattgagat ttgcctcttt ttgagaagtt acagcgatta tacgttcctc   2160
agctgctgct gtcatttccg accgaagttc aacagggct cgactaagtg ccttttgttg    2220
cttctctttc aaggctagtt ggctctttag cctgtctaca agattcctca ttgtggttgt   2280
tggagctctg gagtttgctt cttctgagc ctggagttca gactttaaac tctgggagtc    2340
cttgtgtgct tgggctagag catgccttaa gtcctctacc tctgctttca ctttctttac   2400
ctcactggca tgagtttctt ggagccgtag tttggtattt tcaaactctc tgacttttaa   2460
ctcagtgatt tcttttgtt tttccaaatc ttttgatact ttctttagtt tggtcaaaag    2520
tgaggacaga gagtcatctt gttctgctac tgtctgctcc atctcggcca gacgaatgaa   2580
atgtttgttg gtgggaactg gagcaggaga ctgcttaagt aaatcctgag ctgtctgtct   2640
gaatttattg agtgaattat cggcctgttg ttcaatttg tgatgaagaa catgaaggtc    2700
ttcctcatgc ttcttaacaa tttctctttg ctcctctctg gccttctcca aaggtgctg    2760 gtatttcttc aatacttctt ccttgtgatt taaccttgcc tgcatgttgg caatagtttg   2820
gtgggcaatt ttcattgtgt gatgagattt cggctccagc tcttttcttt ctagctcagc   2880
tataagtttt tctcgatcag ccgtggcagg caatcgaagc ctcagttcat tgattacttt   2940
gtctcttgac agaatatttt gctctgccaa ccgtaaagca gattctttt cttttagttt    3000 ctcttctagt gacttgcaag ttgcttgtgt tttaagaatt acttgaatat tctccttaat   3060
ttttcttaga gcaatttcaa gttggtttgg aagaggcaag ctggggtctg gcattgatcc   3120
tgtagagtct tcaaactttt gtgctgcact gagtatttca ttttgctgat gatcaaaaat   3180
gtctaactgg cgttccagct caacttctct ttgatcccaa gccatctgtc tttcttcatg   3240
gaacttgctt tgctgaacaa tttcttcctc tagactgttg attgtatgct catattcaga   3300
gatgatatta ttcaaatatt tgattcttc tttacccttg actagttctc tatttagctt    3360
aagttcttgg aggcgaagtt cttctatttt cacatgccaa ttgattacct tctgggctcc   3420
cctggcatcc tttaaagtac tgatcaattc ttctaagcct tttaatttta attccaactc   3480
cagtgttttg ttttccatat ttctgtgttc ctgttgcgaa ttcttcattt cttgcattat   3540
cttaagtttg tcatttttgca actgaatcat cgttttggag aacttttcct gctgtgctaa   3600
gggtagagct ccactgaact gtcttcgaag cgactgaatg gtttggcgca ggtgttttgc   3660
tctgttccta ccttccaaac gagcatagta gagcgcctgc tctttttcat ccagtttctg   3720
ttctaagcgc aaattgtagg cttccatctt ctggagtttg gacgtaactg actctaactt   3780
accgagggca gtggcctcac taatttgaag agagacaaca tgttggtgca atttggcaat   3840
tagagccttt tcgtcagatt gtgcctggaa gtccagcagc tgcgttctga gggattccac   3900
ttccttttcc ctggactgtt gttgcgaatt caaaaaatca acttgtcttt tggcaatatc   3960
tgaaatctct ctcagcttgg acacttcaac tttgagctcc acttcactct tctctagttc   4020
tagaatccgc tgtcggtcag catcacttac tgccttggtc acactatcag ctaattcgtc   4080
tctcaacatc tgctccacct tttgtgcatc caggttgatt ttagtaagct cagtgaactt   4140
ggtttccaat tcaaaattac gttcttccat ttgctttaat gaagtcctta agtgctcata   4200
```

-continued

```
cattttctga cagtgttcag ccctctgcct ttcatttaat tccttcatct ccaacacagt    4260
gattttcttt gaaatagaaa caatgtcact gtttgtcatt gatttcttag ccttatccat    4320
gtttgagtca tttcctaact tcgtttcttg ttcccaggcc tgttcaatgg tatggagttt    4380
ttcctttgta atctccagct ctttactgat agcctccatc tgttctttta gcgatgcatt    4440
ctcacactcc aggtgttcta agttacttgt tctttgaaca agcatattat ctttctgcaa    4500
gatgtccctg tacttagtag tcagctcatt gtactgttta ttggctagtt ctaattcaga    4560
caaagaaaca ctattatcta taaccttctg aagagctgca atcttgaaga tggccatttc    4620
cttgaatctt tgcaaacttc caagtttttc agtgacttcg gcctccatgg ctatgacgtc    4680
attcctgtgt ttcccgtttt cctttctcag gtgccgctcc atctccacta aggtggtgta    4740
ctgccggatg agggacttct cgttcacttg cagaacggtg attttcctac tgtttctga    4800
gagcattttc ttcatctcgt tcgaatccat ctgaagagca ctgagcaaat tgttgtactc    4860
ttttactttc acagcatcct gctcagcttg atcttccagt tttctcttct cctctcttat    4920
catctcagag tctgttttcc aaatatcctt ttcacttagg tattctttat ataataaact    4980
ttgttgatga cgaatcactg caaactttct gttataatct tcaagggaat cttctaaatg    5040
ttttaatttc ttttctttat tgtctagttc ctgcaaaaga tgtattaagt attcattctg    5100
agaattgatg atataggcac tggatggtgc tatcccatcg ggtaagtcta tgcctttgta    5160
tactacattg gagcctgcag actgacgtag aaggtcagtt tccttctcaa ggtggtcaat    5220
ctttaagttt gcttttacca actgctgtga ataatttaca gcctctttcc gagattgcct    5280
gagttcttgc cttaattctt cattccttcc tgtaagttgg tcaacttggg cttttagatg    5340
caagctggca tcgaagattc cttctgcatt ctttgattcc atagcgttaa ccagtctttc    5400
aagactcggg atgattaaag atgtttcacc tcctttcaca tcagaatcct tcggcatgtc    5460
cttaatagct tgcaaaattt ctttcatacc ttcttcaagt tgcttatttt cttcgactaa    5520
ttctttttagt ttactctgga atttagcaat tactgtccta cttcttttcta aatctttttc    5580
cttttcagcc aattctcttg aaagaaactc attctttgat tgtgtttcat tcatattatt    5640
gaggctcata aaatttagtt ttcttccttc tattttattt tcatgagaaa aggtttcaga    5700
taagttcaag tcgtcaatgg ttaatcctga ggctgcgttc cttttgcctc tttcttgagc    5760
catttgacga atctttcttt tcaagtcaag acgtcctcc tctagacttt cgatctcttt    5820
caaaagaacc tggttctcag ctctgtactg ttgctgcttt aaccgtttgc tgtttctaaa    5880
ttcagtcaaa tcaatcattg tcttgggttc aaggccagcc cgctctctaa gggcttcgtt    5940
ttcatcaagg atgtcattga tcttcatctc aagcttattg atctccttgg tcaacacttc    6000
catctctcca tctcttattt taatttgggc tttacaattc tttatttcga taacagcatc    6060
ttctaagcca tatactccag attcataatc ttttaatctc ttcagagcct caaccaattc    6120
tttgtccttc tccctggcat cagcctcagc cagctcagct attctctcgg cctcttttgt    6180
tttctcttct aaaatttgta cttttgagtg aattttcata taatgagtct gctgataaaa    6240
gtttgaagta cctttgtctt tttggagttc attttttcaaa tcttcaataa taaacgtatt    6300
tttttccatt tctttcgtat actgttctac ttgctcagta agcatcttaa tttgactgtc    6360
tcgctcctgg ataccctgtt tcagagccat gatgttactt ttgtctgcat caagttgggc    6420
attttttaagt ttccctctca gactctgtag catttgctga tattcaatga tttcatcatc    6480
tttagaagac aaaattaact tccactcttc cacttttgcg ttaacagcca tcatgactgg    6540
atcgtcctct tcatccttcg ccttcagaag atccgtgagc tctcgaactt gcaggcgata    6600
```

```
gtgctcattc tccttcttga tctggtccat gacagcatcc gactgatgca caagcgcttt    6660
catcctgttg tactcatcag tcatcttctc catctcctgc acagactctt ccaggttttt    6720
cctcatttct tggttctgaa cttcaatctt ctcattagct tctgttaagg tctgtatttc    6780
gtccagatat tgaacaagtt catagttctt tttagacaac tgtgatcggt agtcactgtc    6840
ttctcctctc cttgacagaa gtgattcttt ctgtgaatct atttgtttct ggtagtcaat    6900
aatgtcctgc cgaagctgct cattcttttt ctttagacgt tgttctctc ttcttaattt     6960 gctgttttca ttttctgcct cctcatttcg aagagccaat tgttcattaa ccttctttc    7020 tttatccaat tcttttttcca tatcctctaa ttctctatct ttttgttcca gctgcttctc    7080
aagttggcga atttcgtcac gtaaaaaccg agtgtcacgt ccccctgcag actgctgagc    7140
catctccagt tcattttcca gtttcattac ttttgtcttt aattgatttt caaattttgc    7200
ttgttcttct ccagccttttt caacttcttc caaagcgagc tctacttcct gggctttcat    7260
cttcattaga gactgggtaa ttctgaatag atgtatcatg ttttcttggt cttcattttt    7320
tagttcattt acttccacct tggataaaga tatcaataat ttatctgcta actcttcttg    7380
ccgtggcagg tcatctggat caactttgat taattctttc cactttatat taggtggcat    7440
```

<210> SEQ ID NO 4
<211> LENGTH: 2970
<212> TYPE: DNA
<213> ORGANISM: Mus musculus

<400> SEQUENCE: 4

```
ttggcagagc aaatattct gtcaagagac aaagtaatca atgaactgag gcttcgattg      60
cctgccacgg ctgatcgaga aaacttata gctgagctag aaagaaaaga gctggagccg     120
aaatctcatc acacaatgaa aattgcccac caaactattg ccaacatgca ggcaaggtta    180
aatcacaagg aagaagtatt gaagaaatac cagcaccttc tggagaaggc cagagaggag    240
caaagagaaa ttgttaagaa gcatgaggaa gaccttcatg ttcttcatca caaattagaa    300
caacaggccg ataattcact caataaattc agacagacag ctcaggattt acttaagcag    360
tctcctgctc cagttcccac caacaaacat ttcattcgtc tggccgagat ggagcagaca    420
gtagcagaac aagatgactc tctgtcctca cttttgacca aactaaagaa agtatcaaaa    480
gatttggaaa acaaaaaga aatcactgag ttaaaagtca gagagtttga aaataccaaa    540
ctacggctcc aagaaactca tgccagtgag gtaaagaaag tgaaagcaga ggtagaggac    600
ttaaggcatg ctctagccca agcacacaag gactcccaga gtttaaagtc tgaactccag    660
gctcagaaag aagcaaactc cagagctcca acaaccacaa tgaggaatct tgtagacagg    720
ctaaagagcc aactagcctt gaaagagaag caacaaaagg cacttagtcg agccctgttg    780
gaacttcggt cggaaatgac agcagcagct gaggaacgta taatcgctgt aacttctcaa    840
aaagaggcaa atctcaatgt tcaacaagtt gttgagcgcc atactagaga gctaaagtca    900
caaattgaag atttaaatga aaatctttta aaattgaaag aagctcttaa aacaagtaag    960
aacaaagaaa attcactagc tgatgattta aatgaattaa ataatgaact gcaaaaaaag    1020
caaaaagctt ataataaaat ccttagagag aaagatggaa ttgatcaaga aaatgatgaa    1080
ctgagaagac agattaaaag actgtccagt ggactgcaga gcaaaacttt gatagataac    1140
aagcaaagtt taatcgatga acttcaaaag aaagttaaaa aacttgaaag ccaactggaa    1200
agaaaggtgg atgacgtaga cataaagccg gtgaaggaaa agagtagtaa agaagaatta    1260
```

-continued

```
attaggtggg aagaaggtaa gaaatggcaa accaaagtag agggactacg aaacagacta    1320
aaggagaagg aaggagaagc ccacggcctg gcaaagcagc tgaataccct aaaggaactt    1380
tttgccaaag ctgataaaga gaaacttact ttgcagaaga aactgaaaac aacaggaatg    1440
actgttgacc aggttttagg agtgcgagct ttggaatctg aaaagagagtt ggaagagcta    1500
aaaaagaaaa atctggacct agaaaatgac atattataca tgaggaccca gcaggctctt    1560
ccacgagatt ctgttgtgga agacttacat ttacaaaata ataccttca agaaaaactt     1620
catactttag aaaaaaaact ttcaaaggag aaatattctc agtctttgac ttcagaaata    1680
gagtcagatg atcactgtca aaaagaacaa gaacttcaga aggaaaattt gaagttgtca    1740
tctgaaaaca tcgagctgaa atttcaactt gaacaagcaa ataaagattt gccaagacta    1800
aagaatcaag tgaaagattt gaaggaaatg tgtgaatttc ttaagaaagg aaaactggaa    1860
cttgagcgga agcttggtca ggtcagaggg gctggtagaa gtgggaagac aatcccagaa    1920
ctagaaaaaa ccattgggtt aatgaagaaa gtagttgaaa aagtccaaag agaaaatgaa    1980
caattgaaaa aggcatcagg aatactgact agtgaaaaaa tggctactat tgaggaagaa    2040
aatagaaact taaggctga actagaaaag cttaaagctc actttggacg tcagttgagt    2100
atgcagtttg aatctaagaa caaaggtact gagaaaattt ttgccgaaaa tgaacggctt    2160
cggaaagaac ttaagaaaga aatagaagcc tctgagaaac tgcggatagc taagaacaac    2220
ttagagctgg tgaacgacaa gatggcagct caactcgaag aaactgggaa gagactacag    2280
tttgcagaaa gtagagcccc acagctggaa ggtgctgaca gcaagagctg gaagtcaatt    2340
gtggtctcaa gagtgtatga gaccaagatg aaagagcttg aaagtgacat tgccaaaaag    2400
aatcaaagta tcactgacct taaacagctt gtaagagaag caacagagag agaacagaaa    2460
gctaagaaat acactgaaga ccttgaacaa cagattgaga tcctcaaaaa tgttcctgaa    2520
ggtgccgaga cagagcaaga gcttatacgg gaactccagc ttcttagatt agccaataat    2580
cagatggata aagaaagggc agaattaatc catcagatag aaattaacaa ggaccaaacc    2640
agagctgaca gtagcatacc tgattctgat caactaaagg aaaagataaa tgacctggag    2700
acacaactca gaaagttgga gctagaaaag caacattcga aggaggaagt taaaaagctg    2760
aaaaaagaac tggaaaattt tgatccttca ttttttgaag aaattgaaga cctgaagtat    2820
aattataagg aagaagtgaa aaagaatatc ctattagaag agaagctaaa aaaactgtcg    2880
gaacagtttg gatttgaact gcctagtcct cttgctgctt ctgaacactc ggaagatgga    2940
gaaagtcctc atagtttccc tatttattag                                    2970
```

<210> SEQ ID NO 5
<211> LENGTH: 989
<212> TYPE: PRT
<213> ORGANISM: Mus musculus

<400> SEQUENCE: 5

```
Leu Ala Glu Gln Asn Ile Leu Ser Arg Asp Lys Val Ile Asn Glu Leu
1               5                   10                  15

Arg Leu Arg Leu Pro Ala Thr Ala Asp Arg Glu Lys Leu Ile Ala Glu
            20                  25                  30

Leu Glu Arg Lys Glu Leu Glu Pro Lys Ser His Thr Met Lys Ile
        35                  40                  45

Ala His Gln Thr Ile Ala Asn Met Gln Ala Arg Leu Asn His Lys Glu
    50                  55                  60

Glu Val Leu Lys Lys Tyr Gln His Leu Leu Glu Lys Ala Arg Glu Glu
```

```
            65                  70                  75                  80
Gln Arg Glu Ile Val Lys Lys His Glu Glu Asp Leu His Val Leu His
                85                  90                  95

His Lys Leu Glu Gln Gln Ala Asp Asn Ser Leu Asn Lys Phe Arg Gln
            100                 105                 110

Thr Ala Gln Asp Leu Leu Lys Gln Ser Pro Ala Pro Val Pro Thr Asn
            115                 120                 125

Lys His Phe Ile Arg Leu Ala Glu Met Glu Gln Thr Val Ala Glu Gln
            130                 135                 140

Asp Ser Leu Ser Ser Leu Leu Thr Lys Leu Lys Lys Val Ser Lys
145                 150                 155                 160

Asp Leu Glu Lys Gln Lys Glu Ile Thr Glu Leu Lys Val Arg Glu Phe
                165                 170                 175

Glu Asn Thr Lys Leu Arg Leu Gln Glu Thr His Ala Ser Glu Val Lys
            180                 185                 190

Lys Val Lys Ala Glu Val Glu Asp Leu Arg His Ala Leu Ala Gln Ala
        195                 200                 205

His Lys Asp Ser Gln Ser Leu Lys Ser Glu Leu Gln Ala Gln Lys Glu
    210                 215                 220

Ala Asn Ser Arg Ala Pro Thr Thr Thr Met Arg Asn Leu Val Asp Arg
225                 230                 235                 240

Leu Lys Ser Gln Leu Ala Leu Lys Glu Lys Gln Gln Lys Ala Leu Ser
                245                 250                 255

Arg Ala Leu Leu Glu Leu Arg Ser Glu Met Thr Ala Ala Glu Glu
            260                 265                 270

Arg Ile Ile Ala Val Thr Ser Gln Lys Glu Ala Asn Leu Asn Val Gln
        275                 280                 285

Gln Val Val Glu Arg His Thr Arg Glu Leu Lys Ser Gln Ile Glu Asp
    290                 295                 300

Leu Asn Glu Asn Leu Leu Lys Leu Lys Glu Ala Leu Lys Thr Ser Lys
305                 310                 315                 320

Asn Lys Glu Asn Ser Leu Ala Asp Asp Leu Asn Glu Leu Asn Asn Glu
                325                 330                 335

Leu Gln Lys Lys Gln Lys Ala Tyr Asn Lys Ile Leu Arg Glu Lys Asp
            340                 345                 350

Gly Ile Asp Gln Glu Asn Asp Glu Leu Arg Arg Gln Ile Lys Arg Leu
        355                 360                 365

Ser Ser Gly Leu Gln Ser Lys Thr Leu Ile Asp Asn Lys Gln Ser Leu
    370                 375                 380

Ile Asp Glu Leu Gln Lys Lys Val Lys Lys Leu Glu Ser Gln Leu Glu
385                 390                 395                 400

Arg Lys Val Asp Asp Val Asp Ile Lys Pro Val Lys Glu Lys Ser Ser
                405                 410                 415

Lys Glu Glu Leu Ile Arg Trp Glu Glu Gly Lys Lys Trp Gln Thr Lys
            420                 425                 430

Val Glu Gly Leu Arg Asn Arg Leu Lys Glu Lys Glu Gly Glu Ala His
        435                 440                 445

Gly Leu Ala Lys Gln Leu Asn Thr Leu Lys Glu Leu Phe Ala Lys Ala
    450                 455                 460

Asp Lys Glu Lys Leu Thr Leu Gln Lys Lys Leu Lys Thr Thr Gly Met
465                 470                 475                 480

Thr Val Asp Gln Val Leu Gly Val Arg Ala Leu Glu Ser Glu Lys Glu
                485                 490                 495
```

```
Leu Glu Glu Leu Lys Lys Lys Asn Leu Asp Leu Glu Asn Asp Ile Leu
            500                 505                 510

Tyr Met Arg Thr Gln Gln Ala Leu Pro Arg Asp Ser Val Val Glu Asp
            515                 520                 525

Leu His Leu Gln Asn Lys Tyr Leu Gln Glu Lys Leu His Thr Leu Glu
            530                 535                 540

Lys Lys Leu Ser Lys Glu Lys Tyr Ser Gln Ser Leu Thr Ser Glu Ile
545                 550                 555                 560

Glu Ser Asp Asp His Cys Gln Lys Glu Gln Glu Leu Gln Lys Glu Asn
                565                 570                 575

Leu Lys Leu Ser Ser Glu Asn Ile Glu Leu Lys Phe Gln Leu Glu Gln
            580                 585                 590

Ala Asn Lys Asp Leu Pro Arg Leu Lys Asn Gln Val Lys Asp Leu Lys
            595                 600                 605

Glu Met Cys Glu Phe Leu Lys Lys Gly Lys Leu Glu Leu Glu Arg Lys
            610                 615                 620

Leu Gly Gln Val Arg Gly Ala Gly Arg Ser Gly Lys Thr Ile Pro Glu
625                 630                 635                 640

Leu Glu Lys Thr Ile Gly Leu Met Lys Lys Val Val Glu Lys Val Gln
            645                 650                 655

Arg Glu Asn Glu Gln Leu Lys Lys Ala Ser Gly Ile Leu Thr Ser Glu
            660                 665                 670

Lys Met Ala Thr Ile Glu Glu Asn Arg Asn Leu Lys Ala Glu Leu
675                 680                 685

Glu Lys Leu Lys Ala His Phe Gly Arg Gln Leu Ser Met Gln Phe Glu
            690                 695                 700

Ser Lys Asn Lys Gly Thr Glu Lys Ile Val Ala Glu Asn Glu Arg Leu
705                 710                 715                 720

Arg Lys Glu Leu Lys Lys Glu Ile Glu Ala Ser Glu Lys Leu Arg Ile
            725                 730                 735

Ala Lys Asn Asn Leu Glu Leu Val Asn Asp Lys Met Ala Ala Gln Leu
            740                 745                 750

Glu Glu Thr Gly Lys Arg Leu Gln Phe Ala Glu Ser Arg Ala Pro Gln
            755                 760                 765

Leu Glu Gly Ala Asp Ser Lys Ser Trp Lys Ser Ile Val Val Ser Arg
            770                 775                 780

Val Tyr Glu Thr Lys Met Lys Glu Leu Glu Ser Asp Ile Ala Lys Lys
785                 790                 795                 800

Asn Gln Ser Ile Thr Asp Leu Lys Gln Leu Val Arg Glu Ala Thr Glu
                805                 810                 815

Arg Glu Gln Lys Ala Lys Lys Tyr Thr Glu Asp Leu Glu Gln Gln Ile
            820                 825                 830

Glu Ile Leu Lys Asn Val Pro Glu Gly Ala Glu Thr Glu Gln Glu Leu
            835                 840                 845

Ile Arg Glu Leu Gln Leu Leu Arg Leu Ala Asn Asn Gln Met Asp Lys
            850                 855                 860

Glu Arg Ala Glu Leu Ile His Gln Ile Glu Ile Asn Lys Asp Gln Thr
865                 870                 875                 880

Arg Ala Asp Ser Ser Ile Pro Asp Ser Asp Gln Leu Lys Glu Lys Ile
                885                 890                 895

Asn Asp Leu Glu Thr Gln Leu Arg Lys Leu Glu Leu Glu Lys Gln His
            900                 905                 910
```

```
Ser Lys Glu Glu Val Lys Lys Leu Lys Lys Glu Leu Glu Asn Phe Asp
    915                 920                 925
Pro Ser Phe Phe Glu Glu Ile Glu Asp Leu Lys Tyr Asn Tyr Lys Glu
    930                 935                 940
Glu Val Lys Lys Asn Ile Leu Leu Glu Glu Lys Leu Lys Lys Leu Ser
945                 950                 955                 960
Glu Gln Phe Gly Phe Glu Leu Pro Ser Pro Leu Ala Ala Ser Glu His
                965                 970                 975
Ser Glu Asp Gly Glu Ser Pro His Ser Phe Pro Ile Tyr
                980                 985

<210> SEQ ID NO 6
<211> LENGTH: 2970
<212> TYPE: DNA
<213> ORGANISM: Mus musculus

<400> SEQUENCE: 6
ctaataaata gggaaactat gaggactttc tccatcttcc gagtgttcag aagcagcaag      60
aggactaggc agttcaaatc caaactgttc cgacagtttt tttagcttct cttctaatag     120
gatattcttt ttcacttctt ccttataatt atacttcagg tcttcaattt cttcaaaaaa     180
tgaaggatca aaattttcca gttctttttt cagctttta acttcctcct tcgaatgttg      240
cttttctagc tccaactttc tgagttgtgt ctccaggtca tttatctttt cctttagttg     300
atcagaatca ggtatgctac tgtcagctct ggtttggtcc ttgttaattt ctatctgatg     360
gattaattct gcccttttctt tatccatctg attattggct aatctaagaa gctggagttc    420
ccgtataagc tcttgctctg tctcggcacc ttcaggaaca tttttgagga tctcaatctg     480
ttgttcaagg tcttcagtgt atttcttagc tttctgttct ctctctgttg cttctcttac     540
aagctgttta aggtcagtga tactttgatt cttttttggca atgtcacttt caagctcttt     600
catcttggtc tcatacactc ttgagaccac aattgacttc cagctcttgc tgtcagcacc     660
ttccagctgt ggggctctac tttctgcaaa ctgtagtctc ttcccagttt cttcgagttg     720
agctgccatc ttgtcgttca ccagctctaa gttgttctta gctatccgca gtttctcaga     780
ggcttctatt tcttcttaa gttctttccg aagccgttca ttttcggcaa caattttctc      840
agtacctttg ttcttagatt caaactgcat actcaactga cgtccaaagt gagctttaag     900
cttttctagt tcagcctta agtttctatt ttcttcctca atagtagcca ttttttcact     960
agtcagtatt cctgatgcct tttcaattg ttcatttttct ctttggactt tttcaactac     1020
tttcttcatt aacccaatgg ttttttctag ttctgggatt gtcttcccac ttctaccagc    1080
ccctctgacc tgaccaagct tccgctcaag ttccagtttt cctttcttaa gaaattcaca    1140
catttccttc aaatctttca cttgattctt tagtcttggc aaatctttat ttgcttgttc    1200
aagttgaaat ttcagctcga tgttttcaga tgacaacttc aaattttcct tctgaagttc    1260
ttgttctttt tgacagtgat catctgactc tatttctgaa gtcaaagact gagaatattt    1320
ctcctttgaa agttttttt ctaaagtatg aagttttct tgaaggtatt tattttgtaa      1380
atgtaagtct tccacaacag aatctcgtgg aagagcctgc tgggtcctca tgtataatat    1440
gtcattttct aggtccagat ttttcttttt tagctcttcc aactcttttt cagattccaa    1500
agctcgcact cctaaaacct ggtcaacagt cattcctgtt gttttcagtt tcttctgcaa    1560
agtaagtttc tctttatcag ctttggcaaa aagttccttt aaggtattca gctgctttgc    1620
caggccgtgg gcttctcctt ccttctcctt tagtctgttt cgtagtccct ctactttggt    1680
```

```
ttgccatttc ttaccttctt cccacctaat taattcttct ttactactct tttccttcac    1740
cggctttatg tctacgtcat ccacctttct ttccagttgg ctttcaagtt ttttaacttt    1800
cttttgaagt tcatcgatta aactttgctt gttatctatc aaagttttgc tctgcagtcc    1860
actggacagt cttttaatct gtcttctcag ttcatcattt tcttgatcaa ttccatcttt    1920
ctctctaagg attttattat aagcttttg ctttttttgc agttcattat ttaattcatt    1980
taaatcatca gctagtgaat tttctttgtt cttacttgtt ttaagagctt ctttcaatttt   2040 taaaagattt tcatttaaat cttcaatttg tgactttagc tctctagtat ggcgctcaac    2100
aacttgttga acattgagat ttgcctcttt ttgagaagtt acagcgatta tacgttcctc    2160
agctgctgct gtcatttccg accgaagttc aacagggct cgactaagtg ccttttgttg     2220
cttctctttc aaggctagtt ggctctttag cctgtctaca agattcctca ttgtggttgt    2280
tggagctctg gagtttgctt ctttctgagc ctggagttca gactttaaac tctgggagtc    2340
cttgtgtgct tgggctagag catgccttaa gtcctctacc tctgctttca ctttctttac    2400
ctcactggca tgagtttctt ggagccgtag tttggtattt tcaaactctc tgactttaa     2460 ctcagtgatt tcttttttgtt tttccaaatc ttttgatact ttcttttagtt tggtcaaaag  2520 tgaggacaga gagtcatctt gttctgctac tgtctgctcc atctcggcca gacgaatgaa    2580
atgtttgttg gtgggaactg gagcaggaga ctgcttaagt aaatcctgag ctgtctgtct    2640
gaatttattg agtgaattat cggcctgttg ttctaatttg tgatgaagaa catgaaggtc    2700
ttcctcatgc ttcttaacaa tttctctttg ctcctctctg gccttctcca gaaggtgctg    2760
gtatttcttc aatacttctt ccttgtgatt taaccttgcc tgcatgttgg caatagtttg    2820
gtgggcaatt ttcattgtgt gatgagattt cggctccagc tcttttcttt ctagctcagc    2880 tataagttttt tctcgatcag ccgtggcagg caatcgaagc ctcagttcat tgattacttt   2940
gtctcttgac agaatatttt gctctgccaa                                     2970

<210> SEQ ID NO 7
<211> LENGTH: 7440
<212> TYPE: DNA
<213> ORGANISM: Homo sapiens

<400> SEQUENCE: 7
atgccaccta atataaactg gaaagaaata atgaaagttg acccagatga cctgccccgt      60
caagaagaac tggcagataa tttattgatt tccttatcca aggtggaagt aaatgagcta     120
aaaagtgaaa agcaagaaaa tgtgatacac cttttcagaa ttactcagtc actaatgaag     180
atgaaagctc aagaagtgga gctggctttg aagaagtag aaaaagctgg agaagaacaa      240
gcaaaatttg aaaatcaatt aaaaactaaa gtaatgaaac tggaaaatga actggagatg     300
gctcagcagt ctgcaggtgg acgagatact cggttttac gtaatgaaat ttgccaactt      360
gaaaaacaat tagaacaaaa agatagaaa ttggaggaca tggaaaagga gttggagaaa      420
gagaagaaag ttaatgagca attggctctt cgaaatgagg aggcagaaaa tgaaaacagc     480
aaattaagaa gagagaacaa acgtctaaag aaaagaatg aacaactttg tcaggatatt     540
attgactacc agaaacaaat agattcacag aaagaaacac ttttatcaag aagaggggaa    600
gacagtgact accgatcaca gttgtctaaa aaaactatg agcttatcca atatcttgat    660
gaaattcaga ctttaacaga agctaatgag aaaattgaag ttcagaatca agaaatgaga    720
aaaaatttag aagagtctgt acaggaaatg gagaagatga ctgatgaata taatagaatg     780
aaagctattg tgcatcagac agataatgta atagatcagt taaaaaaaga aaacgatcat    840
```

| | | |
|---|---|---|
| tatcaacttc aagtgcagga gcttacagat cttctgaaat caaaaaatga agaagatgat | 900 |
| ccaattatgg tagctgtcaa tgcaaaagta gaagaatgga agctaatttt gtcttctaaa | 960 |
| gatgatgaaa ttattgagta tcagcaaatg ttacataacc taagggagaa acttaagaat | 1020 |
| gctcagcttg atgctgataa aagtaatgtt atggctctac agcagggtat acaggaacga | 1080 |
| gacagtcaaa ttaagatgct caccgaacaa gtagaacaat atacaaaaga atggaaaag | 1140 |
| aatacttgta ttattgaaga tttgaaaaat gagctccaaa gaaacaaagg tgcttcaacc | 1200 |
| ctttctcaac agactcatat gaaaattcag tcaacgttag acattttaaa agagaaaact | 1260 |
| aaagaggctg agaacagc tgaactggct gaggctgatg ctagggaaaa ggataaagaa | 1320 |
| ttagttgagg ctctgaagag gttaaagat tatgaatcgg gagtatatgg tttagaagat | 1380 |
| gctgtcgttg aaataaagaa ttgtaaaaac caaattaaaa taagagatcg agagattgaa | 1440 |
| atattaacaa aggaaatcaa taaacttgaa ttgaagatca gtgatttcct tgatgaaaat | 1500 |
| gaggcactta gagagcgtgt gggccttgaa ccaaagacaa tgattgattt aactgaattt | 1560 |
| agaaatagca aacacttaaa acagcagcag tacagagctg aaaaccagat tcttttgaaa | 1620 |
| gagattgaaa gtctagagga agaacgactt gatctgaaaa aaaaaattcg tcaaatggct | 1680 |
| caagaaagag gaaaagaag tgcaacttca ggattaacca ctgaggacct gaacctaact | 1740 |
| gaaaacattt ctcaaggaga tagaataagt gaaagaaaat tggatttatt gagcctcaaa | 1800 |
| aatatgagtg aagcacaatc aaagaatgaa tttctttcaa gagaactaat tgaaaagaa | 1860 |
| agagatttag aaaggagtag gacagtgata gccaaatttc agaataaatt aaaagaatta | 1920 |
| gttgaagaaa ataagcaact tgaagaaggt atgaaagaaa tattgcaagc aattaaggaa | 1980 |
| atgcagaaag atcctgatgt taaaggagga gaaacatctc taattatccc tagccttgaa | 2040 |
| agactagtta atgctataga atcaaagaat gcagaaggaa tctttgatgc gagtctgcat | 2100 |
| ttgaaagccc aagttgatca gcttaccgga agaaatgaag aattaagaca ggagctcagg | 2160 |
| gaatctcgga aagaggctat aaattattca cagcagttgg caaaagctaa tttaaagata | 2220 |
| gaccatcttg aaaagaaac tagtcttttta cgacaatcag aaggatcgaa tgttgttttt | 2280 |
| aaaggaattg acttacctga tgggatagca ccatctagtg ccagtatcat taattctcag | 2340 |
| aatgaatatt taatacattt gttacaggaa ctagaaaata aagaaaaaaa gttaaagaat | 2400 |
| ttagaagatt ctcttgaaga ttacaacaga aaatttgctg taattcgtca tcaacaaagt | 2460 |
| ttgttgtata aagaatacct aagtgaaaag gagacctgga aaacagaatc taaaacaata | 2520 |
| aaagaggaaa agagaaaact tgaggatcaa gtccaacaag atgctataaa agtaaaagaa | 2580 |
| tataataatt tgctcaatgc tcttcagatg gattcggatg aaatgaaaaa aatacttgca | 2640 |
| gaaaatagta ggaaaattac tgttttgcaa gtgaatgaaa aatcacttat aaggcaatat | 2700 |
| acaaccttag tagaattgga gcgacaactt agaaagaaa atgagaagca aaagaatgaa | 2760 |
| ttgttgtcaa tggaggctga agtttgtgaa aaaattgggt gtttgcaaag atttaaggaa | 2820 |
| atggccattt tcaagattgc agctctccaa aaagttgtag ataatagtgt ttctttgtct | 2880 |
| gaactagaac tggctaataa acagtacaat gaactgactg ctaagtacag ggacatcttg | 2940 |
| caaaaagata atatgcttgt tcaaagaaca agtaacttgg aacacctgga gtgtgaaaac | 3000 |
| atctccttaa aagaacaagt ggagtctata aataaagaac tggagattac caaggaaaaa | 3060 |
| cttcacacta ttgaacaagc ctgggacag gaaactaaat taggtaatga atctagcatg | 3120 |
| gataaggcaa agaaatcaat aaccaacagt gacattgttt ccatttcaaa aaaataact | 3180 |

-continued

```
atgctggaaa tgaaggaatt aaatgaaagg cagcggggctg aacattgtca aaaatgtat    3240 gaacacttac ggacttcgtt aaagcaaatg gaggaacgta attttgaatt ggaaaccaaa    3300
tttgctgagc ttaccaaaat caatttggat gcacagaagg tggaacagat gttaagagat    3360
gaattagctg atagtgtgag caaggcagta agtgatgctg ataggcaacg gattctagaa    3420
ttagagaaga atgaaatgga actaaaagtt gaagtgtcaa aactgagaga gatttctgat    3480
attgccagaa gacaagttga aattttgaat gcacaacaac aatctaggga caaggaagta    3540
gagtccctca gaatgcaact gctagactat caggcacagt ctgatgaaaa gtcgctcatt    3600
gccaagttgc accaacataa tgtctctctt caactgagtg aggctactgc tcttggtaag    3660
ttggagtcaa ttacatctaa actgcagaag atggaggcct acaacttgcg cttagagcag    3720
aaacttgatg aaaagaaca ggctctctat tatgctcgtt tggagggaag aaacagagca    3780
aaacatctgc gccaaacaat tcagtctcta cgacgacagt ttagtggagc tttacccttg    3840
gcacaacagg aaaagttctc caaaacaatg attcaactac aaaatgacaa acttaagata    3900
atgcaagaaa tgaaaaattc tcaacaagaa catagaaata tggagaacaa aacattggag    3960
atggaattaa aattaaaggg cctggaagag ttaataagca cttttaagga taccaaagga    4020
gcccaaaagg taatcaactg gcatatgaaa atagaagaac ttcgtcttca agaacttaaa    4080
ctaaatcggg aattagtcaa ggataaagaa gaataaaaat atttgaataa cataatttct    4140
gaatatgaac gtacaatcag cagtcttgaa gaagaaattg tgcaacagaa caagtttcat    4200
gaagaaagac aaatggcctg ggatcaaaga gaagttgacc tggaacgcca actagacatt    4260
tttgaccgtc agcaaaatga atactaaat gcggcacaaa agtttgaaga agctacagga    4320
tcaatccctg accctagttt gccccttcca aatcaacttg agatcgctct aaggaaaatt    4380
aaggagaaca ttcgaataat tctagaaaca cgggcaactt gcaaatcact agaagagaaa    4440
ctaaaagaga aagaatctgc tttaaggtta gcagaacaaa atatactgtc aagagacaaa    4500
gtaatcaatg aactgaggct tcgattgcct gccactgcag aaagagaaaa gctcatagct    4560
gagctaggca gaaaagagat ggaaccaaaa tctcaccaca cattgaaaat tgctcatcaa    4620
accattgcaa acatgcaagc aaggttaaat caaaaagaag aagtattaaa gaagtatcaa    4680
cgtcttctag aaaaagccag agaggagcaa agagaaattg tgaagaaaca tgaggaagac    4740
cttcatattc ttcatcacag attagaacta caggctgata gttcactaaa taaattcaaa    4800
caaacggctt gggatttaat gaaacagtct cccactccag ttcctaccaa caagcatttt    4860
attcgtctgg ctgagatgga acagacagta gcagaacaag atgactctct ttcctcactc    4920
ttggtcaaac taagaaaagt atcacaagat ttggagagac aaagagaaat cactgaatta    4980
aaagtaaaag aatttgaaaa tatcaaatta cagcttcaag aaaaccatga agatgaagtg    5040
aaaaaagtaa agcggaagt agaggattta aagtatcttc tggaccagtc acaaaaggag    5100
tcacagtgtt taaatctga acttcaggct caaaaagaag caaattcaag agctccaaca    5160
actacaatga gaaatctagt agaacggcta agagccaat tagccttgaa ggagaaacaa    5220
cagaaagcac ttagtcgggc acttttagaa ctccgggcag aaatgacagc agctgctgaa    5280
gaacgtatta tttctgcaac ttctcaaaaa gaggcccatc tcaatgttca acaaatcgtt    5340
gatcgacata ctagagagct aaagacacaa gttgaagatt aaatgaaaaa tcttttaaaa    5400
ttgaaagaag cacttaaaac aagtaaaaac agagaaaact cactaactga taatttgaat    5460
gacttaaata atgaactgca aaagaaacaa aaagcctata ataaaatact tagagagaaa    5520
gaggaaattg atcaagagaa tgatgaactg aaaaggcaaa ttaaaagact aaccagtgga    5580
```

-continued

```
ttacagggca aacccctgac agataataaa caaagtctaa ttgaagaact ccaaaggaaa    5640
gttaaaaaac tagagaacca attagaggga aggtggagg aagtagacct aaaacctatg    5700
aaagaaaaga atgctaaaga agaattaatt aggtgggaag aaggtaaaaa gtggcaagcc    5760
aaaatagaag gaattcgaaa caagttaaaa gagaaagagg gggaagtctt tactttaaca    5820
aagcagttga atactttgaa ggatctttt gccaaagccg ataaagagaa acttactttg    5880
cagaggaaac taaaaacaac tggcatgact gttgatcagg ttttgggaat acgagctttg    5940
gagtcagaaa agaattgga agaattaaaa aagagaaatc ttgacttaga aaatgatata    6000
ttgtatatga gggcccacca agctcttcct cgagattctg ttgtagaaga tttacattta    6060
caaaatagat acctccaaga aaacttcat gctttagaaa acagttttc aaaggataca    6120 tattctaagc cttcaatttc aggaatagag tcagatgatc attgtcagag agaacaggag    6180
cttcagaagg aaaacttgaa gttgtcatct gaaaatattg aactgaaatt tcagcttgaa    6240
caagcaaata aagatttgcc aagattaaag aatcaagtca gagatttgaa ggaaatgtgt    6300
gaatttctta agaaagaaaa agcagaagtt cagcggaaac ttggccatgt tagagggtct    6360
ggtagaagtg gaaagacaat cccagaactg gaaaaaacca ttggtttaat gaaaaaagta    6420
gttgaaaaag tccagagaga aaatgaacag ttgaaaaaag catcaggaat attgactagt    6480
gaaaaaatgg ctaatattga gcaggaaaat gaaaaattga aggctgaatt agaaaaactt    6540
aaagctcatc ttgggcatca gttgagcatg cactatgaat ccaagaccaa aggcacagaa    6600
aaaattattg ctgaaaatga aaggcttcgt aaagaactta aaaagaaac tgatgctgca    6660 gagaaattac ggatagcaaa gaataattta gagatattaa atgagaagat gacagttcaa    6720
ctagaagaga ctggtaagag attgcagttt gcagaaagca gaggtccaca gcttgaaggt    6780
gctgacagta agagctggaa atccattgtg gttacaagaa tgtatgaaac caagttaaaa    6840
gaattggaaa ctgatattgc caaaaaaaat caaagcatta ctgaccttaa acagcttgta    6900
aaagaagcaa cagagagaga acaaaaagtt aacaaataca tgaagacct tgaacaacag    6960 attaagattc ttaaacatgt tcctgaaggt gctgagacag agcaaggcct taaacgggag    7020
cttcaagttc ttagattagc taatcatcag ctggataaag agaaagcaga attaatccat    7080
cagatagaag ctaacaagga ccaaagtgga gctgaaagca ccatacctga tgctgatcaa    7140
ctaaaggaaa aataaaaga tctagagaca cagctcaaaa tgtcagatct agaaaagcag    7200
catttgaagg aggaaataaa gaagctgaaa aagaactgg aaaatttga tccttcattt    7260 tttgaagaaa ttgaagatct taagtataat tacaaggaag aagtgaagaa gaatattctc    7320
ttagaagaga aggtaaaaaa actttcagaa caattgggag ttgaattaac tagccctgtt    7380
gctgcttctg aagagtttga agatgaagaa gaaagtcctg ttaatttccc catttactaa    7440
```

<210> SEQ ID NO 8
<211> LENGTH: 2479
<212> TYPE: PRT
<213> ORGANISM: Homo sapiens

<400> SEQUENCE: 8

```
Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45
```

```
Ile His Leu Phe Arg Ile Thr Gln Ser Leu Met Lys Met Lys Ala Gln
 50                  55                  60

Glu Val Glu Leu Ala Leu Glu Glu Val Glu Lys Ala Gly Glu Glu Gln
 65                  70                  75                  80

Ala Lys Phe Glu Asn Gln Leu Lys Thr Lys Val Met Lys Leu Glu Asn
                 85                  90                  95

Glu Leu Glu Met Ala Gln Gln Ser Ala Gly Arg Asp Thr Arg Phe
                100                 105                 110

Leu Arg Asn Glu Ile Cys Gln Leu Glu Lys Gln Leu Glu Gln Lys Asp
             115                 120                 125

Arg Glu Leu Glu Asp Met Glu Lys Glu Leu Glu Lys Glu Lys Lys Val
         130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
             180                 185                 190

Thr Leu Leu Ser Arg Arg Gly Glu Asp Ser Asp Tyr Arg Ser Gln Leu
         195                 200                 205

Ser Lys Lys Asn Tyr Glu Leu Ile Gln Tyr Leu Asp Glu Ile Gln Thr
     210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Lys Met Thr Asp Glu
                245                 250                 255

Tyr Asn Arg Met Lys Ala Ile Val His Gln Thr Asp Asn Val Ile Asp
             260                 265                 270

Gln Leu Lys Lys Glu Asn Asp His Tyr Gln Leu Gln Val Gln Glu Leu
         275                 280                 285

Thr Asp Leu Leu Lys Ser Lys Asn Glu Glu Asp Asp Pro Ile Met Val
290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
             340                 345                 350

Leu Gln Gln Gly Ile Gln Glu Arg Asp Ser Gln Ile Lys Met Leu Thr
         355                 360                 365

Glu Gln Val Glu Gln Tyr Thr Lys Glu Met Glu Lys Asn Thr Cys Ile
     370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
             420                 425                 430

Asp Ala Arg Glu Lys Asp Lys Glu Leu Val Glu Ala Leu Lys Arg Leu
         435                 440                 445

Lys Asp Tyr Glu Ser Gly Val Tyr Gly Leu Glu Asp Ala Val Val Glu
     450                 455                 460
```

-continued

```
Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
        485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
                515                 520                 525

Gln Gln Tyr Arg Ala Glu Asn Gln Ile Leu Leu Lys Glu Ile Glu Ser
    530                 535                 540

Leu Glu Glu Arg Leu Asp Leu Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
        595                 600                 605

Asn Glu Phe Leu Ser Arg Glu Leu Ile Glu Lys Glu Arg Asp Leu Glu
610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
                675                 680                 685

Lys Asn Ala Glu Gly Ile Phe Asp Ala Ser Leu His Leu Lys Ala Gln
        690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
        755                 760                 765

Ile Ala Pro Ser Ser Ala Ser Ile Ile Asn Ser Gln Asn Glu Tyr Leu
770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
        835                 840                 845

Asp Gln Val Gln Gln Asp Ala Ile Lys Val Lys Glu Tyr Asn Asn Leu
850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
```

-continued

```
                885                 890                 895
Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
            915                 920                 925

Cys Glu Lys Ile Gly Cys Leu Gln Arg Phe Lys Glu Met Ala Ile Phe
    930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
            980                 985                 990

Leu Glu His Leu Glu Cys Glu Asn Ile Ser Leu Lys Glu Gln Val Glu
            995                 1000                1005

Ser Ile Asn Lys Glu Leu Glu Ile Thr Lys Glu Lys Leu His Thr
    1010                1015                1020

Ile Glu Gln Ala Trp Glu Gln Glu Thr Lys Leu Gly Asn Glu Ser
    1025                1030                1035

Ser Met Asp Lys Ala Lys Lys Ser Ile Thr Asn Ser Asp Ile Val
    1040                1045                1050

Ser Ile Ser Lys Lys Ile Thr Met Leu Glu Met Lys Glu Leu Asn
    1055                1060                1065

Glu Arg Gln Arg Ala Glu His Cys Gln Lys Met Tyr Glu His Leu
    1070                1075                1080

Arg Thr Ser Leu Lys Gln Met Glu Glu Arg Asn Phe Glu Leu Glu
    1085                1090                1095

Thr Lys Phe Ala Glu Leu Thr Lys Ile Asn Leu Asp Ala Gln Lys
    1100                1105                1110

Val Glu Gln Met Leu Arg Asp Glu Leu Ala Asp Ser Val Ser Lys
    1115                1120                1125

Ala Val Ser Asp Ala Asp Arg Gln Arg Ile Leu Glu Leu Glu Lys
    1130                1135                1140

Asn Glu Met Glu Leu Lys Val Glu Val Ser Lys Leu Arg Glu Ile
    1145                1150                1155

Ser Asp Ile Ala Arg Arg Gln Val Glu Ile Leu Asn Ala Gln Gln
    1160                1165                1170

Gln Ser Arg Asp Lys Glu Val Glu Ser Leu Arg Met Gln Leu Leu
    1175                1180                1185

Asp Tyr Gln Ala Gln Ser Asp Glu Lys Ser Leu Ile Ala Lys Leu
    1190                1195                1200

His Gln His Asn Val Ser Leu Gln Leu Ser Glu Ala Thr Ala Leu
    1205                1210                1215

Gly Lys Leu Glu Ser Ile Thr Ser Lys Leu Gln Lys Met Glu Ala
    1220                1225                1230

Tyr Asn Leu Arg Leu Glu Gln Lys Leu Asp Glu Lys Glu Gln Ala
    1235                1240                1245

Leu Tyr Tyr Ala Arg Leu Glu Gly Arg Asn Arg Ala Lys His Leu
    1250                1255                1260

Arg Gln Thr Ile Gln Ser Leu Arg Arg Gln Phe Ser Gly Ala Leu
    1265                1270                1275

Pro Leu Ala Gln Gln Glu Lys Phe Ser Lys Thr Met Ile Gln Leu
    1280                1285                1290
```

```
Gln Asn Asp Lys Leu Lys Ile Met Gln Glu Met Lys Asn Ser Gln
    1295                1300                1305

Gln Glu His Arg Asn Met Glu Asn Lys Thr Leu Glu Met Glu Leu
    1310                1315                1320

Lys Leu Lys Gly Leu Glu Glu Leu Ile Ser Thr Leu Lys Asp Thr
    1325                1330                1335

Lys Gly Ala Gln Lys Val Ile Asn Trp His Met Lys Ile Glu Glu
    1340                1345                1350

Leu Arg Leu Gln Glu Leu Lys Leu Asn Arg Glu Leu Val Lys Asp
    1355                1360                1365

Lys Glu Glu Ile Lys Tyr Leu Asn Asn Ile Ile Ser Glu Tyr Glu
    1370                1375                1380

Arg Thr Ile Ser Ser Leu Glu Glu Glu Ile Val Gln Gln Asn Lys
    1385                1390                1395

Phe His Glu Glu Arg Gln Met Ala Trp Asp Gln Arg Glu Val Asp
    1400                1405                1410

Leu Glu Arg Gln Leu Asp Ile Phe Asp Arg Gln Gln Asn Glu Ile
    1415                1420                1425

Leu Asn Ala Ala Gln Lys Phe Glu Glu Ala Thr Gly Ser Ile Pro
    1430                1435                1440

Asp Pro Ser Leu Pro Leu Pro Asn Gln Leu Glu Ile Ala Leu Arg
    1445                1450                1455

Lys Ile Lys Glu Asn Ile Arg Ile Ile Leu Glu Thr Arg Ala Thr
    1460                1465                1470

Cys Lys Ser Leu Glu Glu Lys Leu Lys Glu Lys Glu Ser Ala Leu
    1475                1480                1485

Arg Leu Ala Glu Gln Asn Ile Leu Ser Arg Asp Lys Val Ile Asn
    1490                1495                1500

Glu Leu Arg Leu Arg Leu Pro Ala Thr Ala Glu Arg Glu Lys Leu
    1505                1510                1515

Ile Ala Glu Leu Gly Arg Lys Glu Met Glu Pro Lys Ser His His
    1520                1525                1530

Thr Leu Lys Ile Ala His Gln Thr Ile Ala Asn Met Gln Ala Arg
    1535                1540                1545

Leu Asn Gln Lys Glu Glu Val Leu Lys Lys Tyr Gln Arg Leu Leu
    1550                1555                1560

Glu Lys Ala Arg Glu Glu Gln Arg Glu Ile Val Lys Lys His Glu
    1565                1570                1575

Glu Asp Leu His Ile Leu His His Arg Leu Glu Leu Gln Ala Asp
    1580                1585                1590

Ser Ser Leu Asn Lys Phe Lys Gln Thr Ala Trp Asp Leu Met Lys
    1595                1600                1605

Gln Ser Pro Thr Pro Val Pro Thr Asn Lys His Phe Ile Arg Leu
    1610                1615                1620

Ala Glu Met Glu Gln Thr Val Ala Glu Gln Asp Asp Ser Leu Ser
    1625                1630                1635

Ser Leu Leu Val Lys Leu Lys Lys Val Ser Gln Asp Leu Glu Arg
    1640                1645                1650

Gln Arg Glu Ile Thr Glu Leu Lys Val Lys Glu Phe Glu Asn Ile
    1655                1660                1665

Lys Leu Gln Leu Gln Glu Asn His Glu Asp Glu Val Lys Lys Val
    1670                1675                1680
```

```
Lys Ala Glu Val Glu Asp Leu Lys Tyr Leu Leu Asp Gln Ser Gln
    1685                1690                1695

Lys Glu Ser Gln Cys Leu Lys Ser Glu Leu Gln Ala Gln Lys Glu
    1700                1705                1710

Ala Asn Ser Arg Ala Pro Thr Thr Thr Met Arg Asn Leu Val Glu
    1715                1720                1725

Arg Leu Lys Ser Gln Leu Ala Leu Lys Glu Lys Gln Gln Lys Ala
    1730                1735                1740

Leu Ser Arg Ala Leu Leu Glu Leu Arg Ala Glu Met Thr Ala Ala
    1745                1750                1755

Ala Glu Glu Arg Ile Ile Ser Ala Thr Ser Gln Lys Glu Ala His
    1760                1765                1770

Leu Asn Val Gln Gln Ile Val Asp Arg His Thr Arg Glu Leu Lys
    1775                1780                1785

Thr Gln Val Glu Asp Leu Asn Glu Asn Leu Leu Lys Leu Lys Glu
    1790                1795                1800

Ala Leu Lys Thr Ser Lys Asn Arg Glu Asn Ser Leu Thr Asp Asn
    1805                1810                1815

Leu Asn Asp Leu Asn Asn Glu Leu Gln Lys Lys Gln Lys Ala Tyr
    1820                1825                1830

Asn Lys Ile Leu Arg Glu Lys Glu Glu Ile Asp Gln Glu Asn Asp
    1835                1840                1845

Glu Leu Lys Arg Gln Ile Lys Arg Leu Thr Ser Gly Leu Gln Gly
    1850                1855                1860

Lys Pro Leu Thr Asp Asn Lys Gln Ser Leu Ile Glu Glu Leu Gln
    1865                1870                1875

Arg Lys Val Lys Lys Leu Glu Asn Gln Leu Glu Gly Lys Val Glu
    1880                1885                1890

Glu Val Asp Leu Lys Pro Met Lys Glu Lys Asn Ala Lys Glu Glu
    1895                1900                1905

Leu Ile Arg Trp Glu Glu Gly Lys Lys Trp Gln Ala Lys Ile Glu
    1910                1915                1920

Gly Ile Arg Asn Lys Leu Lys Glu Lys Glu Gly Glu Val Phe Thr
    1925                1930                1935

Leu Thr Lys Gln Leu Asn Thr Leu Lys Asp Leu Phe Ala Lys Ala
    1940                1945                1950

Asp Lys Glu Lys Leu Thr Leu Gln Arg Lys Leu Lys Thr Thr Gly
    1955                1960                1965

Met Thr Val Asp Gln Val Leu Gly Ile Arg Ala Leu Glu Ser Glu
    1970                1975                1980

Lys Glu Leu Glu Glu Leu Lys Lys Arg Asn Leu Asp Leu Glu Asn
    1985                1990                1995

Asp Ile Leu Tyr Met Arg Ala His Gln Ala Leu Pro Arg Asp Ser
    2000                2005                2010

Val Val Glu Asp Leu His Leu Gln Asn Arg Tyr Leu Gln Glu Lys
    2015                2020                2025

Leu His Ala Leu Glu Lys Gln Phe Ser Lys Asp Thr Tyr Ser Lys
    2030                2035                2040

Pro Ser Ile Ser Gly Ile Glu Ser Asp Asp His Cys Gln Arg Glu
    2045                2050                2055

Gln Glu Leu Gln Lys Glu Asn Leu Lys Leu Ser Ser Glu Asn Ile
    2060                2065                2070

Glu Leu Lys Phe Gln Leu Glu Gln Ala Asn Lys Asp Leu Pro Arg
```

```
                    2075                2080                2085
Leu Lys Asn Gln Val Arg Asp Leu Lys Glu Met Cys Glu Phe Leu
        2090                2095                2100
Lys Lys Glu Lys Ala Glu Val Gln Arg Lys Leu Gly His Val Arg
        2105                2110                2115
Gly Ser Gly Arg Ser Gly Lys Thr Ile Pro Glu Leu Glu Lys Thr
        2120                2125                2130
Ile Gly Leu Met Lys Lys Val Val Glu Lys Val Gln Arg Glu Asn
        2135                2140                2145
Glu Gln Leu Lys Lys Ala Ser Gly Ile Leu Thr Ser Glu Lys Met
        2150                2155                2160
Ala Asn Ile Glu Gln Glu Asn Glu Lys Leu Lys Ala Glu Leu Glu
        2165                2170                2175
Lys Leu Lys Ala His Leu Gly His Gln Leu Ser Met His Tyr Glu
        2180                2185                2190
Ser Lys Thr Lys Gly Thr Glu Lys Ile Ile Ala Glu Asn Glu Arg
        2195                2200                2205
Leu Arg Lys Glu Leu Lys Lys Glu Thr Asp Ala Ala Glu Lys Leu
        2210                2215                2220
Arg Ile Ala Lys Asn Asn Leu Glu Ile Leu Asn Glu Lys Met Thr
        2225                2230                2235
Val Gln Leu Glu Glu Thr Gly Lys Arg Leu Gln Phe Ala Glu Ser
        2240                2245                2250
Arg Gly Pro Gln Leu Glu Gly Ala Asp Ser Lys Ser Trp Lys Ser
        2255                2260                2265
Ile Val Val Thr Arg Met Tyr Glu Thr Lys Leu Lys Glu Leu Glu
        2270                2275                2280
Thr Asp Ile Ala Lys Lys Asn Gln Ser Ile Thr Asp Leu Lys Gln
        2285                2290                2295
Leu Val Lys Glu Ala Thr Glu Arg Glu Gln Lys Val Asn Lys Tyr
        2300                2305                2310
Asn Glu Asp Leu Glu Gln Gln Ile Lys Ile Leu Lys His Val Pro
        2315                2320                2325
Glu Gly Ala Glu Thr Glu Gln Gly Leu Lys Arg Glu Leu Gln Val
        2330                2335                2340
Leu Arg Leu Ala Asn His Gln Leu Asp Lys Glu Lys Ala Glu Leu
        2345                2350                2355
Ile His Gln Ile Glu Ala Asn Lys Asp Gln Ser Gly Ala Glu Ser
        2360                2365                2370
Thr Ile Pro Asp Ala Asp Gln Leu Lys Glu Lys Ile Lys Asp Leu
        2375                2380                2385
Glu Thr Gln Leu Lys Met Ser Asp Leu Glu Lys Gln His Leu Lys
        2390                2395                2400
Glu Glu Ile Lys Lys Leu Lys Lys Glu Leu Glu Asn Phe Asp Pro
        2405                2410                2415
Ser Phe Phe Glu Glu Ile Glu Asp Leu Lys Tyr Asn Tyr Lys Glu
        2420                2425                2430
Glu Val Lys Lys Asn Ile Leu Leu Glu Glu Lys Val Lys Lys Leu
        2435                2440                2445
Ser Glu Gln Leu Gly Val Glu Leu Thr Ser Pro Val Ala Ala Ser
        2450                2455                2460
Glu Glu Phe Glu Asp Glu Glu Glu Ser Pro Val Asn Phe Pro Ile
        2465                2470                2475
```

Tyr

<210> SEQ ID NO 9
<211> LENGTH: 7440
<212> TYPE: DNA
<213> ORGANISM: Homo sapiens

<400> SEQUENCE: 9

| | | | | | |
|---|---|---|---|---|---|
| ttagtaaatg | gggaaattaa | caggactttc | ttcttcatct | tcaaactctt | cagaagcagc | 60 |
| aacagggcta | gttaattcaa | ctcccaattg | ttctgaaagt | tttttacct | tctcttctaa | 120 |
| gagaatattc | ttcttcactt | cttccttgta | attatactta | agatcttcaa | tttcttcaaa | 180 |
| aaatgaagga | tcaaaatttt | ccagttcttt | tttcagcttc | tttatttcct | ccttcaaatg | 240 |
| ctgcttttct | agatctgaca | ttttgagctg | tgtctctaga | tctttttattt | tttcctttag | 300 |
| ttgatcagca | tcaggtatgg | tgctttcagc | tccactttgg | tccttgttag | cttctatctg | 360 |
| atggattaat | tctgctttct | ctttatccag | ctgatgatta | gctaatctaa | gaacttgaag | 420 |
| ctcccgttta | aggccttgct | ctgtctcagc | accttcagga | acatgtttaa | gaatcttaat | 480 |
| ctgttgttca | aggtcttcat | tgtatttgtt | aacttttttgt | tctctctctg | ttgcttcttt | 540 |
| tacaagctgt | ttaaggtcag | taatgctttg | atttttttg | gcaatatcag | tttccaattc | 600 |
| ttttaacttg | gtttcataca | ttcttgtaac | cacaatggat | ttccagctct | tactgtcagc | 660 |
| accttcaagc | tgtggacctc | tgcttctgc | aaactgcaat | ctcttaccag | tctcttctag | 720 |
| ttgaactgtc | atcttctcat | ttaatatctc | taaattattc | tttgctatcc | gtaatttctc | 780 |
| tgcagcatca | gtttcttttt | taagttcttt | acgaagcctt | tcattttcag | caataatttt | 840 |
| ttctgtgcct | ttggtcttgg | attcatagtg | catgctcaac | tgatgcccaa | gatgagcttt | 900 |
| aagttttttct | aattcagcct | tcaattttttc | attttcctgc | tcaatattag | ccattttttc | 960 |
| actagtcaat | attcctgatg | cttttttcaa | ctgttcattt | tctctctgga | cttttttcaac | 1020 |
| tactttttttc | attaaaccaa | tggttttttc | cagttctggg | attgtctttc | cacttctacc | 1080 |
| agaccctcta | acatggccaa | gtttccgctg | aacttctgct | ttttctttct | taagaaattc | 1140 |
| acacatttcc | ttcaaatctc | tgacttgatt | ctttaatctt | ggcaaatctt | tatttgcttg | 1200 |
| ttcaagctga | aatttcagtt | caatatttc | agatgacaac | ttcaagtttt | ccttctgaag | 1260 |
| ctcctgttct | ctctgacaat | gatcatctga | ctctattcct | gaaattgaag | gcttagaata | 1320 |
| tgtatccttt | gaaaactgtt | tttctaaagc | atgaagtttt | tcttggaggt | atctattttg | 1380 |
| taaatgtaaa | tcttctacaa | cagaatctcg | aggaagagct | tggtgggccc | tcatatacaa | 1440 |
| tatatcattt | tctaagtcaa | gatttctctt | ttttaattct | tccaattctt | tttctgactc | 1500 |
| caaagctcgt | attcccaaaa | cctgatcaac | agtcatgcca | gttgttttta | gtttcctctg | 1560 |
| caaagtaagt | ttctctttat | cggctttggc | aaaaagatcc | ttcaaagtat | tcaactgctt | 1620 |
| tgttaaagta | aagacttccc | cctctttctc | ttttaacttg | tttcgaattc | cttctatttt | 1680 |
| ggcttgccac | tttttacctt | cttcccacct | aattaattct | tctttagcat | tcttttctt | 1740 |
| cataggtttt | aggtctactt | cctccacctt | tccctctaat | tggttctcta | gttttttaac | 1800 |
| tttcctttgg | agttcttcaa | ttagactttg | tttattatct | gtcaggggtt | tgccctgtaa | 1860 |
| tccactggtt | agtcttttaa | tttgcctttt | cagttcatca | ttctcttgat | caatttcctc | 1920 |
| tttctctcta | agtattttat | tataggcttt | ttgtttcttt | tgcagttcat | tatttaagtc | 1980 |
| attcaaatta | tcagttagtg | agtttctctct | gttttttactt | gttttaagtg | cttcttttcaa | 2040 |

-continued

```
ttttaaaaga ttttcattta aatcttcaac ttgtgtcttt agctctctag tatgtcgatc    2100
aacgatttgt tgaacattga gatgggcctc ttttttgagaa gttgcagaaa taatacgttc   2160
ttcagcagct gctgtcattt ctgcccggag ttctaaaagt gcccgactaa gtgctttctg   2220
ttgtttctcc ttcaaggcta attggctctt tagccgttct actagatttc tcattgtagt   2280
tgttggagct cttgaatttg cttcttttttg agcctgaagt tcagatttta aacactgtga  2340
ctccttttgt gactggtcca gaagatactt taaatcctct acttccgctt ttacttttttt  2400
cacttcatct tcatggtttt cttgaagctg taatttgata ttttcaaatt cttttacttt   2460
taattcagtg atttctcttt gtctctccaa atcttgtgat actttcttta gtttgaccaa   2520
gagtgaggaa agagagtcat cttgttctgc tactgtctgt tccatctcag ccagacgaat   2580
aaaatgcttg ttggtaggaa ctggagtggg agactgtttc attaaatccc aagccgtttg   2640
tttgaattta tttagtgaac tatcagcctg tagttctaat ctgtgatgaa gaatatgaag   2700
gtcttcctca tgtttcttca caatttctct ttgctcctct ctggcttttt ctagaagacg   2760
ttgatacttc tttaatactt cttctttttg atttaacctt gcttgcatgt ttgcaatggt   2820
ttgatgagca attttcaatg tgtggtgaga ttttggttcc atctcttttc tgcctagctc   2880
agctatgagc ttttctcttt ctgcagtggc aggcaatcga agcctcagtt cattgattac   2940
tttgtctctt gacagtatat tttgttctgc taaccttaaa gcagattctt tctcttttag   3000
tttctcttct agtgatttgc aagttgcccg tgtttctaga attattcgaa tgttctcctt   3060
aattttcctt agagcgatct caagttgatt tggaaggggc aaactagggt cagggattga   3120
tcctgtagct tcttcaaact tttgtgccgc atttagtatt tcattttgct gacggtcaaa   3180
aatgtctagt tggcgttcca ggtcaacttc tctttgatcc caggccattt gtctttcttc   3240
atgaaacttg ttctgttgca caatttcttc ttcaagactg ctgattgtac gttcatattc   3300
agaaattatg ttattcaaat attttatttc ttctttatcc ttgactaatt cccgatttag   3360
tttaagttct tgaagacgaa gttcttctat tttcatatgc cagttgatta ccttttgggc   3420
tcctttggta tcctttaaag tgcttattaa ctcttccagg cccttttaatt ttaattccat  3480
ctccaatgtt ttgttctcca tatttctatg ttccttgttga gaattttttca tttcttgcat 3540
tatcttaagt ttgtcatttt gtagttgaat cattgttttg gagaactttt cctgttgtgc   3600
caagggtaaa gctccactaa actgtcgtcg tagagactga attgtttggc gcagatgttt   3660
tgctctgttt cttccctcca aacgagcata atagagagcc tgttctttttt catcaagttt  3720
ctgctctaag cgcaagttgt aggcctccat cttctgcagt ttagatgtaa ttgactccaa   3780
cttaccaaga gcagtagcct cactcagttg aagagagaca ttatgttggt gcaacttggc   3840
aatgagcgac ttttcatcag actgtgcctg atagtctagc agttgcattc tgagggactc   3900
tacttccttg tccctagatt gttgttgtgc attcaaaatt tcaacttgtc ttctggcaat   3960
atcagaaatc tctctcagtt ttgacacttc aacttttagt tccatttcat tcttctctaa   4020
ttctagaatc cgttgcctat cagcatcact tactgccttg ctcacactat cagctaattc   4080
atctcttaac atctgttcca ccttctgtgc atccaaattg attttggtaa gctcagcaaa   4140
tttggtttcc aattcaaaat tacgttcctc catttgcttt aacgaagtcc gtaagtgttc   4200
atacattttt tgacaatgtt cagcccgctg cctttcattt aattccttca tttccagcat   4260
agttattttt tttgaaatgg aaacaatgtc actgttggtt attgattttct ttgccttatc  4320
catgctagat tcattaccta atttagtttc ctgttcccag gcttgttcaa tagtgtgaag   4380
tttttccttg gtaatctcca gttctttatt tatagactcc acttgttctt taaggagat    4440
```

```
gttttcacac tccaggtgtt ccaagttact tgttctttga acaagcatat tatcttttttg   4500
caagatgtcc ctgtacttag cagtcagttc attgtactgt ttattagcca gttctagttc   4560
agacaaagaa acactattat ctacaacttt ttggagagct gcaatcttga aaatggccat   4620
ttccttaaat ctttgcaaac acccaatttt ttcacaaact tcagcctcca ttgacaacaa   4680
ttcattcttt tgcttctcat tttctttttct aagttgtcgc tccaattcta ctaaggttgt   4740
atattgcctt ataagtgatt tttcattcac ttgcaaaaca gtaattttcc tactattttc   4800
tgcaagtatt tttttcattt catccgaatc catctgaaga gcattgagca aattattata   4860
ttcttttact tttatagcat cttgttggac ttgatcctca agttttctct tttcctcttt   4920
tattgtttta gattctgttt tccaggtctc cttttcactt aggtattctt tatacaacaa   4980
actttgttga tgacgaatta cagcaaattt tctgttgtaa tcttcaagag aatcttctaa   5040
attctttaac tttttttctt tattttctag ttcctgtaac aaatgtatta aatattcatt   5100
ctgagaatta atgatactgg cactagatgg tgctatccca tcaggtaagt caattccttt   5160
aaaaacaaca ttcgatcctt ctgattgtcg taaaagacta gtttcttttt caagatggtc   5220
tatctttaaa ttagcttttg ccaactgctg tgaataattt atagcctctt tccgagattc   5280
cctgagctcc tgtcttaatt cttcatttct tccggtaagc tgatcaactt gggctttcaa   5340
atgcagactc gcatcaaaga ttccttctgc attctttgat tctatagcat taactagtct   5400
ttcaaggcta gggataatta gagatgtttc tcctccttta acatcaggat ctttctgcat   5460
ttccttaatt gcttgcaata tttctttcat accttcttca agttgcttat tttcttcaac   5520
taattctttt aatttattct gaaatttggc tatcactgtc ctactccttt ctaaatctct   5580
ttcttttttca attagttctc ttgaaagaaa ttcattctttt gattgtgctt cactcatatt   5640
tttgaggctc aataaatcca atttttctttc acttattcta tctccttgag aaatgttttc   5700
agttaggttc aggtcctcag tggttaatcc tgaagttgca cttcttttttc ctctttcttg   5760
agccatttga cgaattttttt ttttcagatc aagtcgttct tcctctagac tttcaatctc   5820
tttcaaaaga atctggtttt cagctctgta ctgctgctgt tttaagtgtt tgctatttct   5880
aaattcagtt aaatcaatca ttgtctttgg ttcaaggccc acacgctctc taagtgcctc   5940
attttcatca aggaaatcac tgatcttcaa ttcaagttta ttgatttcct ttgttaatat   6000
ttcaatctct cgatctctta ttttaattttg gttttttacaa ttctttattt caacgacagc   6060
atcttctaaa ccatatactc ccgattcata atcttttaac ctcttcagag cctcaactaa   6120
ttctttatcc ttttcccctag catcagcctc agccagttca gctgttctct cagcctcttt   6180
agttttctct tttaaaatgt ctaacgttga ctgaattttc atatgagtct gttgagaaag   6240
ggttgaagca cctttgtttc tttggagctc atttttcaaa tcttcaataa tacaagtatt   6300
cttttccatt tcttttgtat attgttctac ttgttcggtg agcatcttaa tttgactgtc   6360
tcgttcctgt ataccctgct gtagagccat aacattactt ttatcagcat caagctgagc   6420
attcttaagt ttctccctta ggttatgtaa catttgctga tactcaataa tttcatcatc   6480
tttagaagac aaaattagct tccattcttc tactttttgca ttgacagcta ccataattgg   6540
atcatcttct tcatttttttg atttcagaag atctgtaagc cctgcactt gaagttgata   6600
atgatcgttt tctttttttta actgatctat tacattatct gtctgatgca caatagcttt   6660
cattctatta tattcatcag tcatcttctc catttcctgt acagactctt ctaaattttt   6720
tctcatttct tgattctgaa cttcaatttt ctcattagct tctgttaaag tctgaatttc   6780
```

-continued

| | |
|---|---|
| atcaagatat tggataagct catagttttt tttagacaac tgtgatcggt agtcactgtc | 6840 |
| ttcccctctt cttgataaaa gtgtttcttt ctgtgaatct atttgtttct ggtagtcaat | 6900 |
| aatatcctga caaagttgtt cattcttttt ctttagacgt tgttctctc ttcttaattt | 6960 |
| gctgttttca ttttctgcct cctcatttcg aagagccaat tgctcattaa ctttcttctc | 7020 |
| tttctccaac tccttttcca tgtcctccaa ttctctatct ttttgttcta attgtttttc | 7080 |
| aagttggcaa atttcattac gtaaaaaccg agtatctcgt ccacctgcag actgctgagc | 7140 |
| catctccagt tcattttcca gtttcattac tttagttttt aattgatttt caaattttgc | 7200 |
| ttgttcttct ccagcttttt ctacttcttc caaagccagc tccacttctt gagctttcat | 7260 |
| cttcattagt gactgagtaa ttctgaaaag gtgtatcaca ttttcttgct tttcactttt | 7320 |
| tagctcattt acttccacct tggataagga aatcaataaa ttatctgcca gttcttcttg | 7380 |
| acggggcagg tcatctgggt caactttcat tatttctttc cagtttatat taggtggcat | 7440 |

<210> SEQ ID NO 10
<211> LENGTH: 2973
<212> TYPE: DNA
<213> ORGANISM: Homo sapiens

<400> SEQUENCE: 10

| | |
|---|---|
| ttagcagaac aaaatatact gtcaagagac aaagtaatca atgaactgag gcttcgattg | 60 |
| cctgccactg cagaaagaga aaagctcata gctgagctag gcagaaaaga gatggaacca | 120 |
| aaatctcacc acacattgaa aattgctcat caaccattg caaacatgca agcaaggtta | 180 |
| aatcaaaaag aagaagtatt aaagaagtat caacgtcttc tagaaaaagc cagagaggag | 240 |
| caaagagaaa ttgtgaagaa acatgaggaa gaccttcata ttcttcatca cagattagaa | 300 |
| ctacaggctg atagttcact aaataaattc aaacaaacgg cttgggattt aatgaaacag | 360 |
| tctcccactc cagttcctac caacaagcat tttattcgtc tggctgagat ggaacagaca | 420 |
| gtagcagaac aagatgactc tcttttcctca ctcttggtca aactaaagaa agtatcacaa | 480 |
| gatttggaga gacaaagaga aatcactgaa ttaaaagtaa agaatttga aaatatcaaa | 540 |
| ttacagcttc aagaaaacca tgaagatgaa gtgaaaaag taaagcgga agtagaggat | 600 |
| ttaaagtatc ttctggacca gtcacaaaag gagtcacagt gtttaaaatc tgaacttcag | 660 |
| gctcaaaaag aagcaaattc aagagctcca acaactacaa tgagaaatct agtagaacgg | 720 |
| ctaaagagcc aattagcctt gaaggagaaa caacagaaag cacttagtcg ggcactttta | 780 |
| gaactccggg cagaaatgac agcagctgct gaagaacgta ttatttctgc aacttctcaa | 840 |
| aaagaggccc atctcaatgt tcaacaaatc gttgatcgac atactagaga gctaaagaca | 900 |
| caagttgaag atttaaatga aaatctttta aaattgaaag aagcacttaa aacaagtaaa | 960 |
| aacagagaaa actcactaac tgataaattg aatgacttaa ataatgaact gcaaaagaaa | 1020 |
| caaaaagcct ataataaaat acttagagag aagaggaaa ttgatcaaga gaatgatgaa | 1080 |
| ctgaaaaggc aaattaaaag actaaccagt ggattacagg gcaaacccct gacagataat | 1140 |
| aaacaaagtc taattgaaga actccaaagg aaagttaaaa aactagagaa ccaattagag | 1200 |
| ggaaaggtgg aggaagtaga cctaaaacct atgaaagaaa agaatgctaa agaagaatta | 1260 |
| attaggtggg aagaaggtaa aaagtggcaa gccaaaatag aaggaattcg aaacaagtta | 1320 |
| aaagagaaag aggggaagt ctttacttta acaaagcagt tgaatacttt gaaggatctt | 1380 |
| tttgccaaag ccgataaaga gaacttact ttgcagagga aactaaaaac aactggcatg | 1440 |
| actgttgatc aggttttggg aatacgagct ttggagtcag aaaaagaatt ggaagaatta | 1500 |

```
aaaaagagaa atcttgactt agaaaatgat atattgtata tgagggccca ccaagctctt    1560
cctcgagatt ctgttgtaga agatttacat ttacaaaata gatacctcca agaaaaactt    1620
catgctttag aaaaacagtt ttcaaaggat acatattcta agccttcaat ttcaggaata    1680
gagtcagatg atcattgtca gagagaacag gagcttcaga aggaaaactt gaagttgtca    1740
tctgaaaata ttgaactgaa atttcagctt gaacaagcaa ataaagattt gccaagatta    1800
aagaatcaag tcagagattt gaaggaaatg tgtgaatttc ttaagaaaga aaaagcagaa    1860
gttcagcgga aacttggcca tgttagaggg tctggtagaa gtggaaagac aatcccagaa    1920
ctggaaaaaa ccattggttt aatgaaaaaa gtagttgaaa aagtccagag agaaaatgaa    1980
cagttgaaaa aagcatcagg aatattgact agtgaaaaaa tggctaatat tgagcaggaa    2040
aatgaaaaat tgaaggctga attagaaaaa cttaaagctc atcttgggca tcagttgagc    2100
atgcactatg aatccaagac caaaggcaca gaaaaaatta ttgctgaaaa tgaaaggctt    2160
cgtaaagaac ttaaaaaaga aactgatgct gcagagaaat tacggatagc aaagaataat    2220
ttagagatat aaatgagaa gatgacagtt caactagaag agactggtaa gagattgcag    2280
tttgcagaaa gcagaggtcc acagcttgaa ggtgctgaca gtaagagctg gaaatccatt    2340
gtggttacaa gaatgtatga aaccaagtta aaagaattgg aaactgatat tgccaaaaaa    2400
aatcaaagca ttactgacct taaacagctt gtaaaagaag caacagagag agaacaaaaa    2460
gttaacaaat acaatgaaga ccttgaacaa cagattaaga ttcttaaaca tgttcctgaa    2520
ggtgctgaga cagagcaagg ccttaaacgg gagcttcaag ttcttagatt agctaatcat    2580
cagctggata aagagaaagc agaattaatc catcagatag aagctaacaa ggaccaaagt    2640
ggagctgaaa gcaccatacc tgatgctgat caactaaagg aaaaaataaa agatctagag    2700
acacagctca aaatgtcaga tctagaaaag cagcatttga aggaggaaat aaagaagctg    2760 aaaaagagaac tggaaaattt tgatccttca tttttttgaag aaattgaaga tcttaagtat    2820
aattacaagg aagaagtgaa gaagaatatt ctcttagaag agaaggtaaa aaaactttca    2880
gaacaattgg gagttgaatt aactagcccct gttgctgctt ctgaagagtt tgaagatgaa    2940
gaagaaagtc ctgttaattt ccccatttac taa                                 2973
```

<210> SEQ ID NO 11
<211> LENGTH: 990
<212> TYPE: PRT
<213> ORGANISM: Homo sapiens

<400> SEQUENCE: 11

```
Leu Ala Glu Gln Asn Ile Leu Ser Arg Asp Lys Val Ile Asn Glu Leu
1               5                   10                  15

Arg Leu Arg Leu Pro Ala Thr Ala Glu Arg Glu Lys Leu Ile Ala Glu
            20                  25                  30

Leu Gly Arg Lys Glu Met Glu Pro Lys Ser His His Thr Leu Lys Ile
        35                  40                  45

Ala His Gln Thr Ile Ala Asn Met Gln Ala Arg Leu Asn Gln Lys Glu
    50                  55                  60

Glu Val Leu Lys Lys Tyr Gln Arg Leu Leu Glu Lys Ala Arg Glu Glu
65                  70                  75                  80

Gln Arg Glu Ile Val Lys Lys His Glu Glu Asp Leu His Ile Leu His
                85                  90                  95

His Arg Leu Glu Leu Gln Ala Asp Ser Ser Leu Asn Lys Phe Lys Gln
            100                 105                 110
```

-continued

```
Thr Ala Trp Asp Leu Met Lys Gln Ser Pro Thr Pro Val Pro Thr Asn
        115                 120                 125
Lys His Phe Ile Arg Leu Ala Glu Met Glu Gln Thr Val Ala Glu Gln
        130                 135                 140
Asp Asp Ser Leu Ser Ser Leu Leu Val Lys Leu Lys Lys Val Ser Gln
145                 150                 155                 160
Asp Leu Glu Arg Gln Arg Glu Ile Thr Glu Leu Lys Val Lys Glu Phe
                165                 170                 175
Glu Asn Ile Lys Leu Gln Leu Gln Glu Asn His Glu Asp Glu Val Lys
            180                 185                 190
Lys Val Lys Ala Glu Val Glu Asp Leu Lys Tyr Leu Leu Asp Gln Ser
        195                 200                 205
Gln Lys Glu Ser Gln Cys Leu Lys Ser Glu Leu Gln Ala Gln Lys Glu
    210                 215                 220
Ala Asn Ser Arg Ala Pro Thr Thr Thr Met Arg Asn Leu Val Glu Arg
225                 230                 235                 240
Leu Lys Ser Gln Leu Ala Leu Lys Glu Lys Gln Gln Lys Ala Leu Ser
                245                 250                 255
Arg Ala Leu Leu Glu Leu Arg Ala Glu Met Thr Ala Ala Glu Glu
            260                 265                 270
Arg Ile Ile Ser Ala Thr Ser Gln Lys Glu Ala His Leu Asn Val Gln
        275                 280                 285
Gln Ile Val Asp Arg His Thr Arg Glu Leu Lys Thr Gln Val Glu Asp
    290                 295                 300
Leu Asn Glu Asn Leu Leu Lys Leu Lys Glu Ala Leu Lys Thr Ser Lys
305                 310                 315                 320
Asn Arg Glu Asn Ser Leu Thr Asp Asn Leu Asn Asp Leu Asn Asn Glu
                325                 330                 335
Leu Gln Lys Lys Gln Lys Ala Tyr Asn Lys Ile Leu Arg Glu Lys Glu
            340                 345                 350
Glu Ile Asp Gln Glu Asn Asp Glu Leu Lys Arg Gln Ile Lys Arg Leu
        355                 360                 365
Thr Ser Gly Leu Gln Gly Lys Pro Leu Thr Asp Asn Lys Gln Ser Leu
    370                 375                 380
Ile Glu Glu Leu Gln Arg Lys Val Lys Lys Leu Glu Asn Gln Leu Glu
385                 390                 395                 400
Gly Lys Val Glu Glu Val Asp Leu Lys Pro Met Lys Glu Lys Asn Ala
                405                 410                 415
Lys Glu Glu Leu Ile Arg Trp Glu Glu Gly Lys Lys Trp Gln Ala Lys
            420                 425                 430
Ile Glu Gly Ile Arg Asn Lys Leu Lys Glu Lys Glu Gly Glu Val Phe
        435                 440                 445
Thr Leu Thr Lys Gln Leu Asn Thr Leu Lys Asp Leu Phe Ala Lys Ala
    450                 455                 460
Asp Lys Glu Lys Leu Thr Leu Gln Arg Lys Leu Lys Thr Thr Gly Met
465                 470                 475                 480
Thr Val Asp Gln Val Leu Gly Ile Arg Ala Leu Glu Ser Glu Lys Glu
                485                 490                 495
Leu Glu Glu Leu Lys Lys Arg Asn Leu Asp Leu Glu Asn Asp Ile Leu
            500                 505                 510
Tyr Met Arg Ala His Gln Ala Leu Pro Arg Asp Ser Val Val Glu Asp
        515                 520                 525
```

```
Leu His Leu Gln Asn Arg Tyr Leu Gln Glu Lys Leu His Ala Leu Glu
    530                 535                 540
Lys Gln Phe Ser Lys Asp Thr Tyr Ser Lys Pro Ser Ile Ser Gly Ile
545                 550                 555                 560
Glu Ser Asp Asp His Cys Gln Arg Glu Gln Glu Leu Gln Lys Glu Asn
                565                 570                 575
Leu Lys Leu Ser Ser Glu Asn Ile Glu Leu Lys Phe Gln Leu Glu Gln
            580                 585                 590
Ala Asn Lys Asp Leu Pro Arg Leu Lys Asn Gln Val Arg Asp Leu Lys
        595                 600                 605
Glu Met Cys Glu Phe Leu Lys Lys Glu Lys Ala Glu Val Gln Arg Lys
    610                 615                 620
Leu Gly His Val Arg Gly Ser Gly Arg Ser Gly Lys Thr Ile Pro Glu
625                 630                 635                 640
Leu Glu Lys Thr Ile Gly Leu Met Lys Lys Val Glu Lys Val Gln
                645                 650                 655
Arg Glu Asn Glu Gln Leu Lys Lys Ala Ser Gly Ile Leu Thr Ser Glu
                660                 665                 670
Lys Met Ala Asn Ile Glu Gln Glu Asn Glu Lys Leu Lys Ala Glu Leu
    675                 680                 685
Glu Lys Leu Lys Ala His Leu Gly His Gln Leu Ser Met His Tyr Glu
    690                 695                 700
Ser Lys Thr Lys Gly Thr Glu Lys Ile Ile Ala Glu Asn Glu Arg Leu
705                 710                 715                 720
Arg Lys Glu Leu Lys Lys Glu Thr Asp Ala Ala Glu Lys Leu Arg Ile
                725                 730                 735
Ala Lys Asn Asn Leu Glu Ile Leu Asn Glu Lys Met Thr Val Gln Leu
            740                 745                 750
Glu Glu Thr Gly Lys Arg Leu Gln Phe Ala Glu Ser Arg Gly Pro Gln
        755                 760                 765
Leu Glu Gly Ala Asp Ser Lys Ser Trp Lys Ser Ile Val Val Thr Arg
    770                 775                 780
Met Tyr Glu Thr Lys Leu Lys Glu Leu Glu Thr Asp Ile Ala Lys Lys
785                 790                 795                 800
Asn Gln Ser Ile Thr Asp Leu Lys Gln Leu Val Lys Glu Ala Thr Glu
                805                 810                 815
Arg Glu Gln Lys Val Asn Lys Tyr Asn Glu Asp Leu Glu Gln Gln Ile
            820                 825                 830
Lys Ile Leu Lys His Val Pro Glu Gly Ala Glu Thr Glu Gln Gly Leu
        835                 840                 845
Lys Arg Glu Leu Gln Val Leu Arg Leu Ala Asn His Gln Leu Asp Lys
    850                 855                 860
Glu Lys Ala Glu Leu Ile His Gln Ile Glu Ala Asn Lys Asp Gln Ser
865                 870                 875                 880
Gly Ala Glu Ser Thr Ile Pro Asp Ala Asp Gln Leu Lys Glu Lys Ile
                885                 890                 895
Lys Asp Leu Glu Thr Gln Leu Lys Met Ser Asp Leu Glu Lys Gln His
            900                 905                 910
Leu Lys Glu Glu Ile Lys Lys Leu Lys Lys Glu Leu Glu Asn Phe Asp
        915                 920                 925
Pro Ser Phe Phe Glu Glu Ile Glu Asp Leu Lys Tyr Asn Tyr Lys Glu
    930                 935                 940
Glu Val Lys Lys Asn Ile Leu Leu Glu Glu Lys Val Lys Lys Leu Ser
```

Glu Gln Leu Gly Val Glu Leu Thr Ser Pro Val Ala Ala Ser Glu Glu
945                 950                 955                 960
                965                 970                 975

Phe Glu Asp Glu Glu Glu Ser Pro Val Asn Phe Pro Ile Tyr
                980                 985                 990

<210> SEQ ID NO 12
<211> LENGTH: 2973
<212> TYPE: DNA
<213> ORGANISM: Homo sapiens

<400> SEQUENCE: 12

| | | | | | |
|---|---|---|---|---|---|
| ttagtaaatg | gggaaattaa | caggactttc | ttcttcatct | tcaaactctt | cagaagcagc | 60 |
| aacagggcta | gttaattcaa | ctcccaattg | ttctgaaagt | ttttttacct | tctcttctaa | 120 |
| gagaatattc | ttcttcactt | cttccttgta | attatactta | agatcttcaa | tttcttcaaa | 180 |
| aaatgaagga | tcaaaatttt | ccagttcttt | tttcagcttc | tttatttcct | ccttcaaatg | 240 |
| ctgcttttct | agatctgaca | ttttgagctg | tgtctctaga | tcttttattt | tttcctttag | 300 |
| ttgatcagca | tcaggtatgg | tgctttcagc | tccactttgg | tccttgttag | cttctatctg | 360 |
| atggattaat | tctgctttct | ctttatccag | ctgatgatta | gctaatctaa | gaacttgaag | 420 |
| ctcccgttta | aggccttgct | ctgtctcagc | accttcagga | acatgtttaa | gaatcttaat | 480 |
| ctgttgttca | aggtcttcat | tgtatttgtt | aacttttttgt | tctctctctg | ttgcttcttt | 540 |
| tacaagctgt | ttaaggtcag | taatgctttg | atttttttg | gcaatatcag | tttccaattc | 600 |
| ttttaacttg | gttcataca | ttcttgtaac | cacaatggat | ttccagctct | tactgtcagc | 660 |
| accttcaagc | tgtggacctc | tgcttttctgc | aaactgcaat | ctcttaccag | tctcttctag | 720 |
| ttgaactgtc | atcttctcat | ttaatatctc | taaattattc | tttgctatcc | gtaatttctc | 780 |
| tgcagcatca | gtttctttttt | taagttcttt | acgaagcctt | tcattttcag | caataatttt | 840 |
| ttctgtgcct | ttggtcttgg | attcatagtg | catgctcaac | tgatgcccaa | gatgagcttt | 900 |
| aagttttttct | aattcagcct | tcaattttc | attttcctgc | tcaatattag | ccattttttc | 960 |
| actagtcaat | attcctgatg | cttttttcaa | ctgttcattt | tctctctgga | cttttcaac | 1020 |
| tactttttc | attaaaccaa | tggttttttc | cagttctggg | attgtctttc | cacttctacc | 1080 |
| agaccctcta | acatggccaa | gtttccgctg | aacttctgct | ttttctttct | taagaaattc | 1140 |
| acacatttcc | ttcaaatctc | tgacttgatt | ctttaatctt | ggcaaatctt | tatttgcttg | 1200 |
| ttcaagctga | aatttcagtt | caatattttc | agatgacaac | ttcaagtttt | ccttctgaag | 1260 |
| ctcctgttct | ctctgacaat | gatcatctga | ctctattcct | gaaattgaag | gcttagaata | 1320 |
| tgtatccttt | gaaaactgtt | tttctaaagc | atgaagtttt | tcttggaggt | atctatttg | 1380 |
| taaatgtaaa | tcttctacaa | cagaatctcg | aggaagagct | tggtgggccc | tcatatacaa | 1440 |
| tatatcattt | tctaagtcaa | gatttctctt | ttttaattct | tccaattctt | tttctgactc | 1500 |
| caaagctcgt | attcccaaaa | cctgatcaac | agtcatgcca | gttgttttta | gtttcctctg | 1560 |
| caaagtaagt | ttctctttat | cggctttggc | aaaaagatcc | ttcaaagtat | tcaactgctt | 1620 |
| tgttaaagta | aagacttccc | cctctttctc | ttttaacttg | tttcgaattc | cttctatttt | 1680 |
| ggcttgccac | ttttttacctt | cttcccacct | aattaattct | tctttagcat | tcttttcttt | 1740 |
| cataggtttt | aggtctactt | cctccaccct | tccctctaat | tggttctcta | gtttttaac | 1800 |
| tttcctttgg | agttcttcaa | ttagactttg | tttattatct | gtcaggggtt | tgccctgtaa | 1860 |
| tccactggtt | agtcttttaa | tttgcctttt | cagttcatca | ttctcttgat | caatttcctc | 1920 |

```
tttctctcta agtattttat tataggcttt ttgtttcttt tgcagttcat tatttaagtc    1980
attcaaatta tcagttagtg agttttctct gttttttactt gttttaagtg cttcttttcaa   2040 tttaaaaga ttttcattta aatcttcaac ttgtgtcttt agctctctag tatgtcgatc    2100
aacgatttgt tgaacattga gatgggcctc ttttttgagaa gttgcagaaa taatacgttc    2160
ttcagcagct gctgtcattt ctgcccggag ttctaaaagt gcccgactaa gtgctttctg    2220
ttgtttctcc ttcaaggcta attggctctt tagccgttct actagatttc tcattgtagt    2280
tgttggagct cttgaatttg cttcttttttg agcctgaagt tcagatttta aacactgtga    2340
ctccttttgt gactggtcca gaagatactt taaatcctct acttccgctt ttactttttt    2400
cacttcatct tcatggtttt cttgaagctg taatttgata ttttcaaatt cttttacttt    2460
taattcagtg atttctcttt gtctctccaa atcttgtgat actttctta gtttgaccaa    2520 gagtgaggaa agagagtcat cttgttctgc tactgtctgt tccatctcag ccagacgaat    2580
aaaatgcttg ttggtaggaa ctggagtggg agactgtttc attaaatccc aagccgtttg    2640
tttgaattta tttagtgaac tatcagcctg tagttctaat ctgtgatgaa gaatatgaag    2700
gtcttcctca tgtttcttca caatttctct ttgctcctct ctggcttttt ctagaagacg    2760
ttgatacttc tttaatactt cttcttttttg atttaacctt gcttgcatgt ttgcaatggt    2820
ttgatgagca atttttcaatg tgtggtgaga ttttggttcc atctcttttc tgcctagctc    2880
agctatgagc ttttctcttt ctgcagtggc aggcaatcga agcctcagtt cattgattac    2940
tttgtctctt gacagtatat tttgttctgc taa                                  2973

<210> SEQ ID NO 13
<211> LENGTH: 130
<212> TYPE: DNA
<213> ORGANISM: adeno-associated virus 2

<400> SEQUENCE: 13
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact    120
aggggttcct                                                            130

<210> SEQ ID NO 14
<211> LENGTH: 130
<212> TYPE: DNA
<213> ORGANISM: adeno-associated virus 2

<400> SEQUENCE: 14
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120 gagcgcgcag                                                            130

<210> SEQ ID NO 15
<211> LENGTH: 6
<212> TYPE: DNA
<213> ORGANISM: adeno-associated virus 2

<400> SEQUENCE: 15 agttgg                                                                 6

<210> SEQ ID NO 16
<211> LENGTH: 16
<212> TYPE: DNA
```

<213> ORGANISM: adeno-associated virus 2

<400> SEQUENCE: 16
gcgcgctcgc tcgctc                                                16

<210> SEQ ID NO 17
<211> LENGTH: 294
<212> TYPE: DNA
<213> ORGANISM: Homo sapiens

<400> SEQUENCE: 17
gggccccaga agcctggtgg ttgtttgtcc ttctcagggg aaaagtgagg cggccccttg    60
gaggaagggg ccgggcagaa tgatctaatc ggattccaag cagctcaggg gattgtcttt   120
ttctagcacc ttcttgccac tcctaagcgt cctccgtgac cccggctggg atttagcctg   180
gtgctgtgtc agccccgggc tcccaggggc ttcccagtgg tccccaggaa ccctcgacag   240
ggccagggcg tctctctcgt ccagcaaggg cagggacggg ccacaggcca aggg          294

<210> SEQ ID NO 18
<211> LENGTH: 660
<212> TYPE: DNA
<213> ORGANISM: Cytomegalovirus

<400> SEQUENCE: 18
cgcgtggagc tagttattaa tagtaatcaa ttacggggtc attagttcat agcccatata    60
tggagttccg cgttacataa cttacggtaa atggcccgcc tggctgaccg cccaacgacc   120
cccgcccatt gacgtcaata atgacgtatg ttcccatagt aacgtcaata gggactttcc   180
attgacgtca atgggtggag tatttacggt aaactgccca cttggcagta catcaagtgt   240
atcatatgcc aagtacgccc cctattgacg tcaatgacgg taaatggccc gcctggcatt   300
atgcccagta catgacctta tgggactttc ctacttggca gtacatctac gtattagtca   360
tcgctattac catggtgatg cggttttggc agtacatcaa tgggcgtgga tagcggtttg   420
actcacgggg atttccaagt ctccacccca ttgacgtcaa tgggagtttg ttttgcacca   480
aaatcaacgg gactttccaa aatgtcgtaa caactccgcc ccattgacgc aaatgggcgg   540
taggcgtgta cggtgggagg tctatataag cagagctcgt ttagtgaacc gtcagatcgc   600
ctggagacgc catccacgct gttttgacct ccatagaaga caccgggacc gatccagcct   660

<210> SEQ ID NO 19
<211> LENGTH: 2217
<212> TYPE: DNA
<213> ORGANISM: Adeno-associated virus type 8

<400> SEQUENCE: 19
atggctgccg atggttatct tccagattgg ctcgaggaca acctctctga gggcattcgc    60
gagtggtggg cgctgaaacc tggagccccg aagcccaaag ccaaccagca aaagcaggac   120
gacggccggg gtctggtgct tcctggctac aagtacctcg gacccttcaa cggactcgac   180
aaggggagc cgtcaacgc ggcggacgca gcggccctcg agcacgacaa ggcctacgac   240
cagcagctgc aggcgggtga caatccgtac ctgcggtata accacgccga cgccgagttt   300
caggagcgtc tgcaagaaga tacgtctttt gggggcaacc tcgggcgagc agtcttccag   360
gccaagaagc gggttctcga acctctcggt ctggttgagg aaggcgctaa gacggctcct   420
ggaaagaaga gaccggtaga gccatcaccc cagcgttctc cagactcctc tacgggcatc   480
ggcaagaaag gccaacagcc cgccagaaaa agactcaatt ttggtcagac tggcgactca   540

-continued

```
gagtcagttc cagaccctca acctctcgga gaacctccag cagcgccctc tggtgtggga      600
cctaatacaa tggctgcagg cggtggcgca ccaatggcag acaataacga aggcgccgac      660
ggagtgggta gttcctcggg aaattggcat tgcgattcca catggctggg cgacagagtc      720
atcaccacca gcacccgaac ctgggccctg cccacctaca caaccacct ctacaagcaa       780
atctccaacg ggacatcggg aggagccacc aacgacaaca cctacttcgg ctacagcacc      840
ccctgggggt attttgactt taacagattc cactgccact tttcaccacg tgactggcag      900
cgactcatca acaacaactg gggattccgg cccaagagac tcagcttcaa gctcttcaac      960
atccaggtca aggaggtcac gcagaatgaa ggcaccaaga ccatcgccaa taacctcacc     1020
agcaccatcc aggtgtttac ggactcggag taccagctgc cgtacgttct cggctctgcc     1080
caccagggct gcctgcctcc gttcccggcg gacgtgttca tgattcccca gtacggctac     1140
ctaacactca acaacggtag tcaggccgtg gacgctcct ccttctactg cctggaatac      1200
tttccttcgc agatgctgag aaccggcaac aacttccagt ttacttacac cttcgaggac     1260
gtgcctttcc acagcagcta cgcccacagc cagagcttgg accggctgat gaatcctctg     1320
attgaccagt acctgtacta cttgtctcgg actcaaacaa caggaggcac ggcaaatacg     1380
cagactctgg gcttcagcca aggtgggcct aatacaatgg ccaatcaggc aaagaactgg     1440
ctgccaggac cctgttaccg ccaacaacgc gtctcaacga caaccgggca aaacaacaat     1500
agcaactttg cctggactgc tgggaccaaa taccatctga atggaagaaa ttcattggct     1560
aatcctggca tcgctatggc aacacacaaa gacgacgagg agcgtttttt tcccagtaac     1620
gggatcctga ttttttggcaa acaaaatgct gccagagaca atgcggatta cagcgatgtc     1680
atgctcacca gcgaggaaga aatcaaaacc actaaccctg tggctacaga ggaatacggt     1740
atcgtggcag ataacttgca gcagcaaaac acggctcctc aaattggaac tgtcaacagc     1800
caggggggcct acccggtat ggtctggcag aaccgggacg tgtacctgca gggtcccatc      1860
tgggccaaga ttcctcacac ggacggcaac ttccaccccgt ctccgctgat gggcggcttt    1920
ggcctgaaac atcctccgcc tcagatcctg atcaagaaca cgcctgtacc tgcggatcct     1980
ccgaccacct tcaaccagtc aaagctgaac tctttcatca cgcaatacag caccggacag     2040
gtcagcgtgg aaattgaatg ggagctgcag aaggaaaaca gcaagcgctg gaaccccgag     2100
atccagtaca cctccaacta ctacaaatct acaagtgtgg actttgctgt taatacagaa     2160
ggcgtgtact ctgaaccccg ccccattggc acccgttacc tcacccgtaa tctgtaa       2217
```

<210> SEQ ID NO 20
<211> LENGTH: 738
<212> TYPE: PRT
<213> ORGANISM: Adeno-associated virus type 8

<400> SEQUENCE: 20

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

```
Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495
```

| | | | | | | | | | | | |
|---|---|---|---|---|---|---|---|---|---|---|---|
|Gln|Asn|Asn|Asn|Ser|Asn|Phe|Ala|Trp|Thr|Ala|Gly|Thr|Lys|Tyr|His|
| | | |500| | | | |505| | | |510| | | |
|Leu|Asn|Gly|Arg|Asn|Ser|Leu|Ala|Asn|Pro|Gly|Ile|Ala|Met|Ala|Thr|
| | | |515| | | | |520| | | |525| | | |
|His|Lys|Asp|Asp|Glu|Glu|Arg|Phe|Phe|Pro|Ser|Asn|Gly|Ile|Leu|Ile|
| | | |530| | | | |535| | | |540| | | |
|Phe|Gly|Lys|Gln|Asn|Ala|Ala|Arg|Asp|Asn|Ala|Asp|Tyr|Ser|Asp|Val|
|545| | | | |550| | | | |555| | | | |560|
|Met|Leu|Thr|Ser|Glu|Glu|Ile|Lys|Thr|Thr|Asn|Pro|Val|Ala|Thr|
| | | | |565| | | | |570| | | | |575|
|Glu|Glu|Tyr|Gly|Ile|Val|Ala|Asp|Asn|Leu|Gln|Gln|Gln|Asn|Thr|Ala|
| | | | |580| | | | |585| | | | |590| |
|Pro|Gln|Ile|Gly|Thr|Val|Asn|Ser|Gln|Gly|Ala|Leu|Pro|Gly|Met|Val|
| | | | |595| | | | |600| | | | |605| |
|Trp|Gln|Asn|Arg|Asp|Val|Tyr|Leu|Gln|Gly|Pro|Ile|Trp|Ala|Lys|Ile|
| | | |610| | | | |615| | | | |620| | |
|Pro|His|Thr|Asp|Gly|Asn|Phe|His|Pro|Ser|Pro|Leu|Met|Gly|Gly|Phe|
|625| | | | |630| | | | |635| | | | |640|
|Gly|Leu|Lys|His|Pro|Pro|Gln|Ile|Leu|Ile|Lys|Asn|Thr|Pro|Val|
| | | |645| | | | |650| | | | |655| |
|Pro|Ala|Asp|Pro|Pro|Thr|Thr|Phe|Asn|Gln|Ser|Lys|Leu|Asn|Ser|Phe|
| | | |660| | | | |665| | | | |670| | |
|Ile|Thr|Gln|Tyr|Ser|Thr|Gly|Gln|Val|Ser|Val|Glu|Ile|Glu|Trp|Glu|
| | | | |675| | | | |680| | | | |685| |
|Leu|Gln|Lys|Glu|Asn|Ser|Lys|Arg|Trp|Asn|Pro|Glu|Ile|Gln|Tyr|Thr|
| | | |690| | | | |695| | | | |700| | |
|Ser|Asn|Tyr|Tyr|Lys|Ser|Thr|Ser|Val|Asp|Phe|Ala|Val|Asn|Thr|Glu|
|705| | | | |710| | | | |715| | | | |720|
|Gly|Val|Tyr|Ser|Glu|Pro|Arg|Pro|Ile|Gly|Thr|Arg|Tyr|Leu|Thr|Arg|
| | | | |725| | | | |730| | | | |735| |

Asn Leu

<210> SEQ ID NO 21
<211> LENGTH: 294
<212> TYPE: DNA
<213> ORGANISM: Adeno-associated virus type 8

<400> SEQUENCE: 21

```
cccttggcct gtggcccgtc cctgcccttg ctggacgaga gagacgccct ggccctgtcg    60
agggttcctg gggaccactg ggaagcccct gggagcccgg ggctgacaca gcaccaggct   120
aaatcccagc cggggtcacg gaggacgctt aggagtggca agaaggtgct agaaaaagac   180
aatcccctga ctgcttgga atccgattag atcattctgc ccggcccctt cctccaaggg   240
gccgcctcac tttccccctg agaaggacaa acaaccacca ggcttctggg gcc          294
```

<210> SEQ ID NO 22
<211> LENGTH: 897
<212> TYPE: DNA
<213> ORGANISM: Mus musculus

<400> SEQUENCE: 22

```
gatttactta agcagtctcc tgctccagtt cccaccaaca acatttcat tcgtctggcc      60
gagatggagc agacagtagc agaacaagat gactctctgt cctcactttt gaccaaacta   120
aagaaagtat caaagatttt ggaaaaacaa aagaaatca ctgagttaaa agtcagagag   180
```

```
tttgaaaata ccaaactacg gctccaagaa actcatgcca gtgaggtaaa gaaagtgaaa    240
gcagaggtag aggacttaag gcatgctcta gcccaagcac acaaggactc ccagagttta    300
aagtctgaac tccaggctca gaaagaagca aactccagag ctccaacaac cacaatgagg    360
aatcttgtag acaggctaaa gagccaacta gccttgaaag agaagcaaca aaaggcactt    420
agtcgagccc tgttggaact tcggtcggaa atgacagcag cagctgagga acgtataatc    480
gctgtaactt ctcaaaaaga ggcaaatctc aatgttcaac aagttgttga gcgccatact    540
agagagctaa agtcacaaat tgaagattta aatgaaaatc ttttaaaatt gaaagaagct    600
cttaaaacaa gtaagaacaa agaaaattca ctagctgatg atttaaatga attaaataat    660
gaactgcaaa aaaagcaaaa agcttataat aaaatcctta gagagaaaga tggaattgat    720
caagaaaatg atgaactgag aagacagatt aaaagactgt ccagtggact gcagagcaaa    780
actttgatag ataacaagca aagtttaatc gatgaacttc aaaagaaagt taaaaaactt    840
gaaagccaac tggaaagaaa ggtggatgac gtagacataa agccggtgaa ggaaaag      897
```

<210> SEQ ID NO 23
<211> LENGTH: 299
<212> TYPE: PRT
<213> ORGANISM: Mus musculus

<400> SEQUENCE: 23

Asp Leu Leu Lys Gln Ser Pro Ala Pro Val Pro Thr Asn Lys His Phe
1               5                   10                  15

Ile Arg Leu Ala Glu Met Glu Gln Thr Val Ala Glu Gln Asp Asp Ser
            20                  25                  30

Leu Ser Ser Leu Leu Thr Lys Leu Lys Val Ser Lys Asp Leu Glu
        35                  40                  45

Lys Gln Lys Glu Ile Thr Glu Leu Lys Val Arg Glu Phe Glu Asn Thr
50                  55                  60

Lys Leu Arg Leu Gln Glu Thr His Ala Ser Glu Val Lys Lys Val Lys
65                  70                  75                  80

Ala Glu Val Glu Asp Leu Arg His Ala Leu Ala Gln Ala His Lys Asp
                85                  90                  95

Ser Gln Ser Leu Lys Ser Glu Leu Gln Ala Gln Lys Glu Ala Asn Ser
            100                 105                 110

Arg Ala Pro Thr Thr Thr Met Arg Asn Leu Val Asp Arg Leu Lys Ser
        115                 120                 125

Gln Leu Ala Leu Lys Glu Lys Gln Gln Lys Ala Leu Ser Arg Ala Leu
130                 135                 140

Leu Glu Leu Arg Ser Glu Met Thr Ala Ala Glu Glu Arg Ile Ile
145                 150                 155                 160

Ala Val Thr Ser Gln Lys Glu Ala Asn Leu Asn Val Gln Gln Val Val
                165                 170                 175

Glu Arg His Thr Arg Glu Leu Lys Ser Gln Ile Glu Asp Leu Asn Glu
            180                 185                 190

Asn Leu Leu Lys Leu Lys Glu Ala Leu Lys Thr Ser Lys Asn Lys Glu
        195                 200                 205

Asn Ser Leu Ala Asp Asp Leu Asn Glu Leu Asn Asn Glu Leu Gln Lys
210                 215                 220

Lys Gln Lys Ala Tyr Asn Lys Ile Leu Arg Glu Lys Asp Gly Ile Asp
225                 230                 235                 240

Gln Glu Asn Asp Glu Leu Arg Arg Gln Ile Lys Arg Leu Ser Ser Gly
                245                 250                 255

```
Leu Gln Ser Lys Thr Leu Ile Asp Asn Lys Gln Ser Leu Ile Asp Glu
        260                 265                 270

Leu Gln Lys Lys Val Lys Lys Leu Glu Ser Gln Leu Glu Arg Lys Val
        275                 280                 285

Asp Asp Val Asp Ile Lys Pro Val Lys Glu Lys
        290                 295
```

<210> SEQ ID NO 24
<211> LENGTH: 897
<212> TYPE: DNA
<213> ORGANISM: Mus musculus

<400> SEQUENCE: 24

| | | | | | | |
|---|---|---|---|---|---|---|
| cttttccttc | accggcttta | tgtctacgtc | atccaccttt | ctttccagtt | ggctttcaag | 60 |
| ttttttaact | ttcttttgaa | gttcatcgat | taaactttgc | ttgttatcta | tcaaagtttt | 120 |
| gctctgcagt | ccactggaca | gtctttaat | ctgtcttctc | agttcatcat | tttcttgatc | 180 |
| aattccatct | ttctctctaa | ggattttatt | ataagctttt | tgctttttt | gcagttcatt | 240 |
| atttaattca | tttaaatcat | cagctagtga | attttctttg | ttcttacttg | ttttaagagc | 300 |
| ttctttcaat | tttaaaagat | tttcatttaa | atcttcaatt | tgtgactta | gctctctagt | 360 |
| atggcgctca | acaacttgtt | gaacattgag | atttgcctct | ttttgagaag | ttacagcgat | 420 |
| tatacgttcc | tcagctgctg | ctgtcatttc | cgaccgaagt | tccaacaggg | ctcgactaag | 480 |
| tgccttttgt | tgcttctctt | tcaaggctag | ttggctcttt | agcctgtcta | caagattcct | 540 |
| cattgtggtt | gttggagctc | tggagtttgc | ttctttctga | gcctggagtt | cagactttaa | 600 |
| actctgggag | tccttgtgtg | cttgggctag | agcatgcctt | aagtcctcta | cctctgcttt | 660 |
| cactttcttt | acctcactgg | catgagtttc | ttggagccgt | agtttggtat | tttcaaactc | 720 |
| tctgactttt | aactcagtga | tttcttttg | tttttccaaa | tcttttgata | cttttctttag | 780 |
| tttggtcaaa | agtgaggaca | gagagtcatc | ttgttctgct | actgtctgct | ccatctcggc | 840 |
| cagacgaatg | aaatgtttgt | tggtgggaac | tggagcagga | gactgcttaa | gtaaatc | 897 |

<210> SEQ ID NO 25
<211> LENGTH: 897
<212> TYPE: DNA
<213> ORGANISM: Homo sapiens

<400> SEQUENCE: 25

| | | | | | | |
|---|---|---|---|---|---|---|
| gatttaatga | aacagtctcc | cactccagtt | cctaccaaca | agcattttat | tcgtctggct | 60 |
| gagatggaac | agacagtagc | agaacaagat | gactctcttt | cctcactctt | ggtcaaacta | 120 |
| aagaaagtat | cacaagattt | ggagagacaa | agagaaatca | ctgaattaaa | agtaaaagaa | 180 |
| tttgaaaata | tcaaattaca | gcttcaagaa | aaccatgaag | atgaagtgaa | aaaagtaaaa | 240 |
| gcggaagtag | aggatttaaa | gtatcttctg | gaccagtcac | aaaaggagtc | acagtgttta | 300 |
| aaatctgaac | ttcaggctca | aaaagaagca | aattcaagag | ctccaacaac | tacaatgaga | 360 |
| aatctagtag | aacggctaaa | gagccaatta | gccttgaagg | agaaacaaca | gaaagcactt | 420 |
| agtcgggcac | ttttagaact | ccgggcagaa | atgacagcag | ctgctgaaga | acgtattatt | 480 |
| tctgcaactt | ctcaaaaaga | ggcccatctc | aatgttcaac | aaatcgttga | tcgacatact | 540 |
| agagagctaa | agacacaagt | tgaagattta | aatgaaaatc | ttttaaaatt | gaaagaagca | 600 |
| cttaaaacag | gtaaaacag | agaaaactca | ctaactgata | atttgaatga | cttaaataat | 660 |
| gaactgcaaa | agaaacaaaa | agcctataat | aaaatactta | gagagaaaga | ggaaattgat | 720 |

```
caagagaatg atgaactgaa aaggcaaatt aaaagactaa ccagtggatt acagggcaaa    780
cccctgacag ataataaaca aagtctaatt gaagaactcc aaaggaaagt taaaaaacta    840
gagaaccaat tagagggaaa ggtggaggaa gtagacctaa aacctatgaa agaaaag      897
```

<210> SEQ ID NO 26
<211> LENGTH: 299
<212> TYPE: PRT
<213> ORGANISM: Homo sapiens

<400> SEQUENCE: 26

```
Asp Leu Met Lys Gln Ser Pro Thr Pro Val Pro Thr Asn Lys His Phe
1               5                   10                  15

Ile Arg Leu Ala Glu Met Glu Gln Thr Val Ala Glu Gln Asp Asp Ser
            20                  25                  30

Leu Ser Ser Leu Leu Val Lys Leu Lys Val Ser Gln Asp Leu Glu
        35                  40                  45

Arg Gln Arg Glu Ile Thr Glu Leu Lys Val Lys Glu Phe Glu Asn Ile
    50                  55                  60

Lys Leu Gln Leu Gln Glu Asn His Glu Asp Glu Val Lys Lys Val Lys
65                  70                  75                  80

Ala Glu Val Glu Asp Leu Lys Tyr Leu Leu Asp Gln Ser Gln Lys Glu
                85                  90                  95

Ser Gln Cys Leu Lys Ser Glu Leu Gln Ala Gln Lys Glu Ala Asn Ser
            100                 105                 110

Arg Ala Pro Thr Thr Thr Met Arg Asn Leu Val Glu Arg Leu Lys Ser
        115                 120                 125

Gln Leu Ala Leu Lys Glu Lys Gln Gln Lys Ala Leu Ser Arg Ala Leu
    130                 135                 140

Leu Glu Leu Arg Ala Glu Met Thr Ala Ala Glu Glu Arg Ile Ile
145                 150                 155                 160

Ser Ala Thr Ser Gln Lys Glu Ala His Leu Asn Val Gln Gln Ile Val
                165                 170                 175

Asp Arg His Thr Arg Glu Leu Lys Thr Gln Val Glu Asp Leu Asn Glu
            180                 185                 190

Asn Leu Leu Lys Leu Lys Glu Ala Leu Lys Thr Ser Lys Asn Arg Glu
        195                 200                 205

Asn Ser Leu Thr Asp Asn Leu Asn Asp Leu Asn Asn Glu Leu Gln Lys
    210                 215                 220

Lys Gln Lys Ala Tyr Asn Lys Ile Leu Arg Glu Lys Glu Glu Ile Asp
225                 230                 235                 240

Gln Glu Asn Asp Glu Leu Lys Arg Gln Ile Lys Arg Leu Thr Ser Gly
                245                 250                 255

Leu Gln Gly Lys Pro Leu Thr Asp Asn Lys Gln Ser Leu Ile Glu Glu
            260                 265                 270

Leu Gln Arg Lys Val Lys Leu Glu Asn Gln Leu Glu Gly Lys Val
        275                 280                 285

Glu Glu Val Asp Leu Lys Pro Met Lys Glu Lys
    290                 295
```

<210> SEQ ID NO 27
<211> LENGTH: 897
<212> TYPE: DNA
<213> ORGANISM: Homo sapiens

<400> SEQUENCE: 27

```
cttttctttc ataggtttta ggtctacttc ctccacctttt ccctctaatt ggttctctag        60 tttttaact ttcctttgga gttcttcaat tagactttgt ttattatctg tcagggtttt        120
gccctgtaat ccactggtta gtctttaat ttgccttttc agttcatcat tctcttgatc        180
aatttcctct ttctctctaa gtattttatt ataggctttt tgtttctttt gcagttcatt        240
atttaagtca ttcaaattat cagttagtga gttttctctg tttttacttg ttttaagtgc        300
ttctttcaat tttaaaagat tttcatttaa atcttcaact tgtgtcttta gctctctagt        360
atgtcgatca acgatttgtt gaacattgag atgggcctct ttttgagaag ttgcagaaat        420
aatacgttct tcagcagctg ctgtcatttc tgcccggagt tctaaaagtg cccgactaag        480
tgctttctgt tgtttctcct tcaaggctaa ttggctcttt agccgttcta ctagatttct        540
cattgtagtt gttggagctc ttgaatttgc ttcttttga gcctgaagtt cagattttaa         600
acactgtgac tccttttgtg actggtccag aagatacttt aaatcctcta cttccgcttt        660 tactttttc acttcatctt catggttttc ttgaagctgt aatttgatat tttcaaattc        720 ttttacttt aattcagtga tttctctttg tctctccaaa tcttgtgata cttcttag         780 tttgaccaag agtgaggaaa gagagtcatc ttgttctgct actgtctgtt ccatctcagc        840
cagacgaata aaatgcttgt tggtaggaac tggagtggga gactgtttca ttaaatc            897
```

<210> SEQ ID NO 28
<211> LENGTH: 3924
<212> TYPE: DNA
<213> ORGANISM: Mus musculus

<400> SEQUENCE: 28

```
caacaacagt ccagggaaaa ggaagtggaa tccctcagaa cgcagctgct ggacttccag         60
gcacaatctg acgaaaaggc tctaattgcc aaattgcacc aacatgttgt ctctcttcaa        120
attagtgagg ccactgccct cggtaagtta gagtcagtta cgtccaaact ccagaagatg        180
gaagcctaca atttgcgctt agaacagaaa ctggatgaaa aagagcaggc gctctactat        240
gctcgtttgg aagtagaaaa cagagcaaaa cacctgcgcc aaaccattca gtcgcttcga        300
agacagttca gtggagctct acccttagca cagcaggaaa agttctccaa aacgatgatt        360
cagttgcaaa atgacaaact taagataatg caagaaatga agaattcgca acaggaacac        420
agaaatatgg aaaacaaaac actggagttg gaattaaaat taaaaggctt agaagaattg        480
atcagtactt taaggatgc caggggagcc cagaaggtaa tcaattggca tgtgaaaata        540
gaagaacttc gcctccaaga acttaagcta aatagagaac tagtcaaggg taagaagaa         600 atcaaatatt tgaataatat catctctgaa tatgagcata caatcaacag tctagaggaa        660
gaaattgttc agcaaagcaa gttccatgaa gaaagacaga tggcttggga tcaaagagaa        720
gttgagctgg aacgccagtt agacattttt gatcatcagc aaaatgaaat actcagtgca        780
gcacaaaagt ttgaagactc tacaggatca atgccagacc ccagcttgcc tcttccaaac        840
caacttgaaa ttgctctaag aaaaattaag gagaatattc aagtaattct taaaacacaa        900
gcaacttgca agtcactaga agagaaacta aagaaaaag aatctgcttt acggttggca        960
gagcaaaata ttctgtcaag agacaaagta atcaatgaac tgaggcttcg attgcctgcc       1020
acggctgatc gagaaaaact tatagctgag ctagaaagaa aagagctgga gccgaaatct       1080
catcacacaa tgaaaattgc ccaccaaact attgccaaca tgcaggcaag gttaaatcac       1140
aaggaagaag tattgaagaa ataccagcac cttctggaga aggccagaga ggagcaaaga       1200
```

```
gaaattgtta agaagcatga ggaagacctt catgttcttc atcacaaatt agaacaacag    1260
gccgataatt cactcaataa attcagacag acagctcagg atttacttaa gcagtctcct    1320
gctccagttc ccaccaacaa acatttcatt cgtctggccg agatggagca gacagtagca    1380
gaacaagatg actctctgtc ctcacttttg accaaactaa agaaagtatc aaagatttg     1440 gaaaaacaaa aagaaatcac tgagttaaaa gtcagagagt ttgaaaatac caaactacgg    1500
ctccaagaaa ctcatgccag tgaggtaaag aaagtgaaag cagaggtaga ggacttaagg    1560
catgctctag cccaagcaca caaggactcc cagagtttaa agtctgaact ccaggctcag    1620
aaagaagcaa actccagagc tccaacaacc acaatgagga atcttgtaga caggctaaag    1680
agccaactag ccttgaaaga gaagcaacaa aaggcactta gtcgagccct gttggaactt    1740
cggtcggaaa tgacagcagc agctgaggaa cgtataatcg ctgtaacttc tcaaaaagag    1800
gcaaatctca atgttcaaca agttgttgag cgccatacta gagagctaaa gtcacaaatt    1860
gaagatttaa atgaaaatct tttaaaattg aaagaagctc ttaaaacaag taagaacaaa    1920
gaaaattcac tagctgatga tttaaatgaa ttaaataatg aactgcaaaa aaagcaaaaa    1980
gcttataata aaatccttag agagaaagat ggaattgatc aagaaaatga tgaactgaga    2040
agacagatta aaagactgtc cagtggactg cagagcaaaa ctttgataga taacaagcaa    2100
agtttaatcg atgaacttca aaagaaagtt aaaaaacttg aaagccaact ggaaagaaag    2160
gtggatgacg tagacataaa gccggtgaag gaaaagagta gtaaagaaga attaattagg    2220
tgggaagaag gtaagaaatg gcaaaccaaa gtagagggac tacgaaacag actaaaggag    2280
aaggaaggag aagcccacgg cctggcaaag cagctgaata ccttaaagga acttttttgcc   2340 aaagctgata agagaaact tactttgcag aagaaactga aacaacagg aatgactgtt      2400 gaccaggttt taggagtgcg agctttggaa tctgaaaaag agttggaaga gctaaaaaag    2460
aaaaatctgg acctagaaaa tgacatatta tacatgagga cccagcaggc tcttccacga    2520
gattctgttg tggaagactt acatttacaa aataaatacc ttcaagaaaa acttcatact    2580
ttagaaaaaa aactttcaaa ggagaaatat tctcagtctt tgacttcaga aatagagtca    2640
gatgatcact gtcaaaaaga acaagaactt cagaaggaaa atttgaagtt gtcatctgaa    2700
aacatcgagc tgaaatttca acttgaacaa gcaaataaag atttgccaag actaaagaat    2760
caagtgaaag atttgaagga aatgtgtgaa tttcttaaga aaggaaaact ggaacttgag    2820
cggaagcttg gtcaggtcag aggggctggt agaagtggga agacaatccc agaactagaa    2880
aaaaccattg ggttaatgaa gaaagtagtt gaaaaagtcc aaagagaaaa tgaacaattg    2940
aaaaaggcat caggaatact gactagtgaa aaaatggcta ctattgagga agaaaataga    3000
aacttaaagg ctgaactaga aaagcttaaa gctcactttg acgtcagtt gagtatgcag      3060 tttgaatcta agaacaaagg tactgagaaa attgttgccg aaaatgaacg gcttcggaaa    3120
gaacttaaga agaaaataga agcctctgag aaactgcgga tagctaagaa caacttagag    3180
ctggtgaacg acaagatggc agctcaactc gaagaaactg ggaagagact acagtttgca    3240
gaaagtagag ccccacagct ggaaggtgct gacagcaaga gctggaagtc aattgtggtc    3300
tcaagagtgt atgagaccaa gatgaaagag cttgaaagtg acattgccaa aaagaatcaa    3360
agtatcactg accttaaaca gcttgtaaga gaagcaacag agagagaaca gaaagctaag    3420
aaatacactg aagaccttga caacagatt gagatcctca aaaatgttcc tgaaggtgcc     3480
gagacagagc aagagcttat acgggaactc cagcttctta gattagccaa taatcagatg    3540
gataaagaaa gggcagaatt aatccatcag atagaaatta acaaggacca aaccagagct    3600
```

```
gacagtagca tacctgattc tgatcaacta aaggaaaaga taaatgacct ggagacacaa  3660
ctcagaaagt tggagctaga aaagcaacat tcgaaggagg aagttaaaaa gctgaaaaaa  3720
gaactggaaa attttgatcc ttcatttttt gaagaaattg aagacctgaa gtataattat  3780
aaggaagaag tgaaaaagaa tatcctatta gaagagaagc taaaaaaact gtcggaacag  3840
tttggatttg aactgcctag tcctcttgct gcttctgaac actcggaaga tggagaaagt  3900
cctcatagtt tccctattta ttag                                         3924
```

<210> SEQ ID NO 29
<211> LENGTH: 1307
<212> TYPE: PRT
<213> ORGANISM: Mus musculus

<400> SEQUENCE: 29

```
Gln Gln Gln Ser Arg Glu Lys Glu Val Glu Ser Leu Arg Thr Gln Leu
1               5                   10                  15

Leu Asp Phe Gln Ala Gln Ser Asp Glu Lys Ala Leu Ile Ala Lys Leu
            20                  25                  30

His Gln His Val Val Ser Leu Gln Ile Ser Glu Ala Thr Ala Leu Gly
        35                  40                  45

Lys Leu Glu Ser Val Thr Ser Lys Leu Gln Lys Met Glu Ala Tyr Asn
    50                  55                  60

Leu Arg Leu Glu Gln Lys Leu Asp Glu Lys Glu Gln Ala Leu Tyr Tyr
65                  70                  75                  80

Ala Arg Leu Glu Gly Arg Asn Arg Ala Lys His Leu Arg Gln Thr Ile
                85                  90                  95

Gln Ser Leu Arg Arg Gln Phe Ser Gly Ala Leu Pro Leu Ala Gln Gln
            100                 105                 110

Glu Lys Phe Ser Lys Thr Met Ile Gln Leu Gln Asn Asp Lys Leu Lys
        115                 120                 125

Ile Met Gln Glu Met Lys Asn Ser Gln Gln Glu His Arg Asn Met Glu
    130                 135                 140

Asn Lys Thr Leu Glu Leu Glu Leu Lys Leu Lys Gly Leu Glu Glu Leu
145                 150                 155                 160

Ile Ser Thr Leu Lys Asp Ala Arg Gly Ala Gln Lys Val Ile Asn Trp
                165                 170                 175

His Val Lys Ile Glu Glu Leu Arg Leu Gln Glu Leu Lys Leu Asn Arg
            180                 185                 190

Glu Leu Val Lys Gly Lys Glu Glu Ile Lys Tyr Leu Asn Asn Ile Ile
        195                 200                 205

Ser Glu Tyr Glu His Thr Ile Asn Ser Leu Glu Glu Glu Ile Val Gln
    210                 215                 220

Gln Ser Lys Phe His Glu Glu Arg Gln Met Ala Trp Asp Gln Arg Glu
225                 230                 235                 240

Val Glu Leu Glu Arg Gln Leu Asp Ile Phe Asp His Gln Gln Asn Glu
                245                 250                 255

Ile Leu Ser Ala Ala Gln Lys Phe Glu Asp Ser Thr Gly Ser Met Pro
            260                 265                 270

Asp Pro Ser Leu Pro Leu Pro Asn Gln Leu Glu Ile Ala Leu Arg Lys
        275                 280                 285

Ile Lys Glu Asn Ile Gln Val Ile Leu Lys Thr Gln Ala Thr Cys Lys
    290                 295                 300

Ser Leu Glu Glu Lys Leu Lys Glu Lys Glu Ser Ala Leu Arg Leu Ala
```

```
            305                 310                 315                 320
Glu Gln Asn Ile Leu Ser Arg Asp Lys Val Ile Asn Glu Leu Arg Leu
                325                 330                 335

Arg Leu Pro Ala Thr Ala Asp Arg Glu Lys Leu Ile Ala Glu Leu Glu
                340                 345                 350

Arg Lys Glu Leu Glu Pro Lys Ser His His Thr Met Lys Ile Ala His
                355                 360                 365

Gln Thr Ile Ala Asn Met Gln Ala Arg Leu Asn His Lys Glu Glu Val
            370                 375                 380

Leu Lys Lys Tyr Gln His Leu Leu Glu Lys Ala Arg Glu Glu Gln Arg
385                 390                 395                 400

Glu Ile Val Lys Lys His Glu Asp Leu His Val Leu His His Lys
                405                 410                 415

Leu Glu Gln Gln Ala Asp Asn Ser Leu Asn Lys Phe Arg Gln Thr Ala
                420                 425                 430

Gln Asp Leu Leu Lys Gln Ser Pro Ala Pro Val Pro Thr Asn Lys His
            435                 440                 445

Phe Ile Arg Leu Ala Glu Met Glu Gln Thr Val Ala Glu Gln Asp Asp
450                 455                 460

Ser Leu Ser Ser Leu Leu Thr Lys Leu Lys Val Ser Lys Asp Leu
465                 470                 475                 480

Glu Lys Gln Lys Glu Ile Thr Glu Leu Lys Val Arg Glu Phe Glu Asn
                485                 490                 495

Thr Lys Leu Arg Leu Gln Glu Thr His Ala Ser Glu Val Lys Lys Val
            500                 505                 510

Lys Ala Glu Val Glu Asp Leu Arg His Ala Leu Ala Gln Ala His Lys
            515                 520                 525

Asp Ser Gln Ser Leu Lys Ser Glu Leu Gln Ala Gln Lys Glu Ala Asn
            530                 535                 540

Ser Arg Ala Pro Thr Thr Thr Met Arg Asn Leu Val Asp Arg Leu Lys
545                 550                 555                 560

Ser Gln Leu Ala Leu Lys Glu Lys Gln Gln Lys Ala Leu Ser Arg Ala
                565                 570                 575

Leu Leu Glu Leu Arg Ser Glu Met Thr Ala Ala Ala Glu Glu Arg Ile
            580                 585                 590

Ile Ala Val Thr Ser Gln Lys Glu Ala Asn Leu Asn Val Gln Gln Val
            595                 600                 605

Val Glu Arg His Thr Arg Glu Leu Lys Ser Gln Ile Glu Asp Leu Asn
            610                 615                 620

Glu Asn Leu Leu Lys Leu Lys Glu Ala Leu Lys Thr Ser Lys Asn Lys
625                 630                 635                 640

Glu Asn Ser Leu Ala Asp Asp Leu Asn Glu Leu Asn Asn Glu Leu Gln
                645                 650                 655

Lys Lys Gln Lys Ala Tyr Asn Lys Ile Leu Arg Glu Lys Asp Gly Ile
                660                 665                 670

Asp Gln Glu Asn Asp Glu Leu Arg Arg Gln Ile Lys Arg Leu Ser Ser
            675                 680                 685

Gly Leu Gln Ser Lys Thr Leu Ile Asp Asn Lys Gln Ser Leu Ile Asp
            690                 695                 700

Glu Leu Gln Lys Lys Val Lys Lys Leu Glu Ser Gln Leu Glu Arg Lys
705                 710                 715                 720

Val Asp Asp Val Asp Ile Lys Pro Val Lys Glu Lys Ser Ser Lys Glu
                725                 730                 735
```

```
-continued

Glu Leu Ile Arg Trp Glu Gly Lys Lys Trp Gln Thr Lys Val Glu
            740                 745                 750

Gly Leu Arg Asn Arg Leu Lys Glu Lys Glu Gly Glu Ala His Gly Leu
            755                 760                 765

Ala Lys Gln Leu Asn Thr Leu Lys Glu Leu Phe Ala Lys Ala Asp Lys
770                 775                 780

Glu Lys Leu Thr Leu Gln Lys Lys Leu Lys Thr Thr Gly Met Thr Val
785                 790                 795                 800

Asp Gln Val Leu Gly Val Arg Ala Leu Glu Ser Glu Lys Glu Leu Glu
            805                 810                 815

Glu Leu Lys Lys Lys Asn Leu Asp Leu Glu Asn Asp Ile Leu Tyr Met
            820                 825                 830

Arg Thr Gln Gln Ala Leu Pro Arg Asp Ser Val Val Glu Asp Leu His
            835                 840                 845

Leu Gln Asn Lys Tyr Leu Gln Glu Lys Leu His Thr Leu Glu Lys Lys
850                 855                 860

Leu Ser Lys Glu Lys Tyr Ser Gln Ser Leu Thr Ser Glu Ile Glu Ser
865                 870                 875                 880

Asp Asp His Cys Gln Lys Glu Glu Leu Gln Lys Glu Asn Leu Lys
            885                 890                 895

Leu Ser Ser Glu Asn Ile Glu Leu Lys Phe Gln Leu Glu Gln Ala Asn
            900                 905                 910

Lys Asp Leu Pro Arg Leu Lys Asn Gln Val Lys Asp Leu Lys Glu Met
            915                 920                 925

Cys Glu Phe Leu Lys Lys Gly Lys Leu Glu Leu Glu Arg Lys Leu Gly
            930                 935                 940

Gln Val Arg Gly Ala Gly Arg Ser Gly Lys Thr Ile Pro Glu Leu Glu
945                 950                 955                 960

Lys Thr Ile Gly Leu Met Lys Lys Val Val Glu Lys Val Gln Arg Glu
                965                 970                 975

Asn Glu Gln Leu Lys Lys Ala Ser Gly Ile Leu Thr Ser Glu Lys Met
            980                 985                 990

Ala Thr Ile Glu Glu Glu Asn Arg Asn Leu Lys Ala Glu Leu Glu Lys
            995                 1000                1005

Leu Lys Ala His Phe Gly Arg Gln Leu Ser Met Gln Phe Glu Ser
    1010                1015                1020

Lys Asn Lys Gly Thr Glu Lys Ile Val Ala Glu Asn Glu Arg Leu
    1025                1030                1035

Arg Lys Glu Leu Lys Lys Glu Ile Glu Ala Ser Glu Lys Leu Arg
    1040                1045                1050

Ile Ala Lys Asn Asn Leu Glu Leu Val Asn Asp Lys Met Ala Ala
    1055                1060                1065

Gln Leu Glu Glu Thr Gly Lys Arg Leu Gln Phe Ala Glu Ser Arg
    1070                1075                1080

Ala Pro Gln Leu Glu Gly Ala Asp Ser Lys Ser Trp Lys Ser Ile
    1085                1090                1095

Val Val Ser Arg Val Tyr Glu Thr Lys Met Lys Glu Leu Glu Ser
    1100                1105                1110

Asp Ile Ala Lys Lys Asn Gln Ser Ile Thr Asp Leu Lys Gln Leu
    1115                1120                1125

Val Arg Glu Ala Thr Glu Arg Glu Gln Lys Ala Lys Lys Tyr Thr
    1130                1135                1140
```

| | | | | | | | | | | |
|---|---|---|---|---|---|---|---|---|---|---|
|Glu|Asp|Leu|Glu|Gln|Gln|Ile|Glu|Ile|Leu|Lys|Asn|Val|Pro|Glu|
| |1145| | | |1150| | | |1155| |

Gly Ala Glu Thr Glu Gln Glu Leu Ile Arg Glu Leu Gln Leu Leu
    1160            1165                1170

Arg Leu Ala Asn Asn Gln Met Asp Lys Glu Arg Ala Glu Leu Ile
    1175            1180                1185

His Gln Ile Glu Ile Asn Lys Asp Gln Thr Arg Ala Asp Ser Ser
    1190            1195                1200

Ile Pro Asp Ser Asp Gln Leu Lys Glu Lys Ile Asn Asp Leu Glu
    1205            1210                1215

Thr Gln Leu Arg Lys Leu Glu Leu Glu Lys Gln His Ser Lys Glu
    1220            1225                1230

Glu Val Lys Lys Leu Lys Lys Glu Leu Glu Asn Phe Asp Pro Ser
    1235            1240                1245

Phe Phe Glu Glu Ile Glu Asp Leu Lys Tyr Asn Tyr Lys Glu Glu
    1250            1255                1260

Val Lys Lys Asn Ile Leu Leu Glu Glu Lys Leu Lys Lys Leu Ser
    1265            1270                1275

Glu Gln Phe Gly Phe Glu Leu Pro Ser Pro Leu Ala Ala Ser Glu
    1280            1285                1290

His Ser Glu Asp Gly Glu Ser Pro His Ser Phe Pro Ile Tyr
    1295            1300                1305

<210> SEQ ID NO 30
<211> LENGTH: 3924
<212> TYPE: DNA
<213> ORGANISM: Mus musculus

<400> SEQUENCE: 30

```
ctaataaata gggaaactat gaggactttc tccatcttcc gagtgttcag aagcagcaag      60
aggactaggc agttcaaatc caaactgttc cgacagtttt tttagcttct cttctaatag     120
gatattcttt ttcacttctt ccttataatt atacttcagg tcttcaattt cttcaaaaaa     180
tgaaggatca aaattttcca gttctttttt cagctttta acttcctcct tcgaatgttg     240 ctttttctagc tccaactttc tgagttgtgt ctccaggtca tttatctttt cctttagttg     300
atcagaatca ggtatgctac tgtcagctct ggtttggtcc ttgttaattt ctatctgatg     360
gattaattct gcccttctt tatccatctg attattggct aatctaagaa gctggagttc       420
ccgtataagc tcttgctctg tctcggcacc ttcaggaaca ttttgagga tctcaatctg      480 ttgttcaagg tcttcagtgt atttcttagc tttctgttct ctctctgttg cttctcttac     540
aagctgttta aggtcagtga actttgatt ctttttggca atgtcacttt caagctcttt      600
catcttggtc tcatacactc ttgagaccac aattgacttc cagctcttgc tgtcagcacc     660
ttccagctgt ggggctctac tttctgcaaa ctgtagtctc ttcccagttt cttcgagttg     720
agctgccatc ttgtcgttca ccagctctaa gttgttctta gctatccgca gtttctcaga     780
ggcttctatt tctttcttaa gttctttccg aagccgttca ttttcggcaa caattttctc     840
agtacctttg ttcttagatt caaactgcat actcaactga cgtccaaagt gagctttaag     900
cttttctagt tcagccttta agtttctatt ttcttcctca atagtagcca ttttttcact     960
agtcagtatt cctgatgcct ttttcaattg ttcattttct ctttggactt tttcaactac    1020
tttcttcatt aacccaatgg ttttttctag ttctgggatt gtcttcccac ttctaccagc    1080
ccctctgacc tgaccaagct tccgctcaag ttccagtttt cctttcttaa gaaattcaca    1140
```

```
catttccttc aaatctttca cttgattctt tagtcttggc aaatctttat ttgcttgttc    1200
aagttgaaat ttcagctcga tgttttcaga tgacaacttc aaattttcct tctgaagttc    1260
ttgttctttt tgacagtgat catctgactc tatttctgaa gtcaaagact gagaatattt    1320
ctcctttgaa agtttttttt ctaaagtatg aagttttct tgaaggtatt tattttgtaa     1380
atgtaagtct tccacaacag aatctcgtgg aagagcctgc tgggtcctca tgtataatat    1440
gtcattttct aggtccagat ttttcttttt tagctcttcc aactcttttt cagattccaa    1500
agctcgcact cctaaaacct ggtcaacagt cattcctgtt gttttcagtt tcttctgcaa    1560
agtaagtttc tctttatcag ctttggcaaa aagttccttt aaggtattca gctgctttgc    1620
caggccgtgg gcttctcctt ccttctcctt tagtctgttt cgtagtccct ctactttggt    1680
ttgccatttc ttaccttctt cccacctaat taattcttct ttactactct tttccttcac    1740
cggctttatg tctacgtcat ccacctttct ttccagttgg ctttcaagtt ttttaacttt    1800
cttttgaagt tcatcgatta aactttgctt gttatctatc aaagttttgc tctgcagtcc    1860
actggacagt cttttaatct gtcttctcag ttcatcattt tcttgatcaa ttccatcttt    1920
ctctctaagg attttattat aagcttttg ctttttttgc agttcattat ttaattcatt      1980
taaatcatca gctagtgaat tttctttgtt cttacttgtt ttaagagctt ctttcaattt    2040
taaaagattt tcatttaaat cttcaatttg tgactttagc tctctagtat ggcgctcaac    2100
aacttgttga acattgagat ttgcctcttt ttgagaagtt acagcgatta tacgttcctc    2160
agctgctgct gtcatttccg accgaagttc aacagggct cgactaagtg ccttttgttg      2220
cttctctttc aaggctagtt ggctcttag cctgtctaca agattcctca ttgtggttgt      2280
tggagctctg gagtttgctt ctttctgagc ctggagttca gactttaaac tctgggagtc    2340
cttgtgtgct tgggctagag catgccttaa gtcctctacc tctgctttca ctttctttac    2400
ctcactggca tgagtttctt ggagccgtag tttggtattt tcaaactctc tgactttaa     2460
ctcagtgatt tcttttttgtt tttccaaatc ttttgatact ttctttagtt tggtcaaaag    2520
tgaggacaga gagtcatctt gttctgctac tgtctgctcc atctcggcca gacgaatgaa    2580
atgtttgttg gtgggaactg gagcaggaga ctgcttaagt aaatcctgag ctgtctgtct    2640
gaatttattg agtgaattat cggcctgttg ttctaatttg tgatgaagaa catgaaggtc    2700
ttcctcatgc ttcttaacaa tttctctttg ctcctctctg gccttctcca gaaggtgctg    2760
gtatttcttc aatacttctt ccttgtgatt taaccttgcc tgcatgttgg caatagtttg    2820
gtgggcaatt ttcattgtgt gatgagattt cggctccagc tcttttcttt ctagctcagc    2880
tataagtttt tctcgatcag ccgtggcagg caatcgaagc ctcagttcat tgattacttt    2940
gtctcttgac agaatatttt gctctgccaa ccgtaaagca gattcttttt cttttagttt    3000
ctcttctagt gacttgcaag ttgcttgtgt tttaagaatt acttgaatat tctccttaat    3060
ttttcttaga gcaatttcaa gttggtttgg aagaggcaag ctggggtctg gcattgatcc    3120
tgtagagtct tcaaactttt gtgctgcact gagtatttca ttttgctgat gatcaaaaat    3180
gtctaactgg cgttccagct caacttctct ttgatcccaa gccatctgtc tttcttcatg    3240
gaacttgctt tgctgaacaa tttcttcctc tagactgttg attgtatgct catattcaga    3300
gatgatatta ttcaaatatt tgatttcttc tttacccttg actagttctc tatttagctt    3360
aagttcttgg aggcgaagtt cttctatttt cacatgccaa ttgattacct tctgggctcc    3420
cctggcatcc tttaaagtac tgatcaattc ttctaagcct tttaattta attccaactc      3480
cagtgttttg ttttccatat ttctgtgttc ctgttgcgaa ttcttcattt cttgcattat    3540
```

| | |
|---|---|
| cttaagtttg tcattttgca actgaatcat cgttttggag aacttttcct gctgtgctaa | 3600 |
| gggtagagct ccactgaact gtcttcgaag cgactgaatg gtttggcgca ggtgttttgc | 3660 |
| tctgtttcta ccttccaaac gagcatagta gagcgcctgc tcttttcat ccagtttctg | 3720 |
| ttctaagcgc aaattgtagg cttccatctt ctggagtttg gacgtaactg actctaactt | 3780 |
| accgagggca gtggcctcac taatttgaag agagacaaca tgttggtgca atttggcaat | 3840 |
| tagagccttt tcgtcagatt gtgcctggaa gtccagcagc tgcgttctga gggattccac | 3900 |
| ttccttttcc ctggactgtt gttg | 3924 |

<210> SEQ ID NO 31
<211> LENGTH: 3924
<212> TYPE: DNA
<213> ORGANISM: Homo sapiens

<400> SEQUENCE: 31

| | |
|---|---|
| caacaatcta gggacaagga agtagagtcc ctcagaatgc aactgctaga ctatcaggca | 60 |
| cagtctgatg aaaagtcgct cattgccaag ttgcaccaac ataatgtctc tcttcaactg | 120 |
| agtgaggcta ctgctcttgg taagttggag tcaattacat ctaaactgca aagatggag | 180 |
| gcctacaact tgcgcttaga gcagaaactt gatgaaaaag aacaggctct ctattatgct | 240 |
| cgtttggagg aagaaacag agcaaaacat ctgcgccaaa caattcagtc tctacgacga | 300 |
| cagtttagtg gagctttacc cttggcacaa caggaaaagt tctccaaaac aatgattcaa | 360 |
| ctacaaaatg acaaacttaa gataatgcaa gaaatgaaaa attctcaaca gaacataga | 420 |
| aatatggaga acaaaacatt ggagatggaa ttaaaattaa agggcctgga agagttaata | 480 |
| agcactttaa aggataccaa aggagcccaa aaggtaatca actggcatat gaaaatagaa | 540 |
| gaacttcgtc ttcaagaact taaactaaat cgggaattag tcaaggataa agaagaaata | 600 |
| aaatatttga ataacataat ttctgaatat gaacgtacaa tcagcagtct tgaagaagaa | 660 |
| attgtgcaac agaacaagtt tcatgaagaa agacaaatgg cctgggatca aagagaagtt | 720 |
| gacctggaac gccaactaga catttttgac cgtcagcaaa atgaaatact aaatgcggca | 780 |
| caaaagtttg aagaagctac aggatcaatc cctgaccta gttgccccct tccaaatcaa | 840 |
| cttgagatcg ctctaaggaa aattaaggag aacattcgaa taattctaga aacacgggca | 900 |
| acttgcaaat cactagaaga gaaactaaaa gagaaagaat ctgctttaag gttagcagaa | 960 |
| caaaatatac tgtcaagaga caaagtaatc aatgaactga ggcttcgatt gcctgccact | 1020 |
| gcagaaagag aaaagctcat agctgagcta ggcagaaaag gatggaacc aaaatctcac | 1080 |
| cacacattga aaattgctca tcaaaccatt gcaaacatgc aagcaaggtt aaatcaaaaa | 1140 |
| gaagaagtat taagaagta tcaacgtctt ctagaaaag ccagagagga gcaaagagaa | 1200 |
| attgtgaaga acatgagga agaccttcat attcttcatc acagattaga actacaggct | 1260 |
| gatagttcac taaataaatt caaacaaacg gcttgggatt taatgaaaca gtctcccact | 1320 |
| ccagttccta ccaacaagca ttttattcgt ctggctgaga tggaacagac agtagcagaa | 1380 |
| caagatgact ctcttccctc actcttggtc aaactaaaga agtatcaca agatttggag | 1440 |
| agacaaagag aaatcactga attaaaagta aaagaatttg aaaatatcaa attacagctt | 1500 |
| caagaaaacc atgaagatga agtgaaaaaa gtaaagcgg aagtagagga tttaaagtat | 1560 |
| cttctggacc agtcacaaaa ggagtcacag tgtttaaaat ctgaacttca ggctcaaaaa | 1620 |
| gaagcaaatt caagagctcc aacaactaca atgagaaatc tagtagaacg gctaaagagc | 1680 |

| | |
|---|---|
| caattagcct tgaaggagaa acaacagaaa gcacttagtc gggcactttt agaactccgg | 1740 |
| gcagaaatga cagcagctgc tgaagaacgt attatttctg caacttctca aaaagaggcc | 1800 |
| catctcaatg ttcaacaaat cgttgatcga catactagag agctaaagac acaagttgaa | 1860 |
| gatttaaatg aaaatctttt aaaattgaaa gaagcactta aacaagtaa aaacagagaa | 1920 |
| aactcactaa ctgataattt gaatgactta aataatgaac tgcaaaagaa acaaaaagcc | 1980 |
| tataataaaa tacttagaga gaaagaggaa attgatcaag agaatgatga actgaaaagg | 2040 |
| caaattaaaa gactaaccag tggattacag ggcaaacccc tgacagataa taaacaaagt | 2100 |
| ctaattgaag aactccaaag gaaagttaaa aaactagaga accaattaga gggaaaggtg | 2160 |
| gaggaagtag acctaaaacc tatgaaagaa aagaatgcta agaagaatt aattaggtgg | 2220 |
| gaagaaggta aaaagtggca agccaaaata gaaggaattc gaaacaagtt aaaagagaaa | 2280 |
| gaggggggaag tctttacttt aacaaagcag ttgaatactt tgaaggatct ttttgccaaa | 2340 |
| gccgataaag agaaacttac tttcagagg aaactaaaaa caactggcat gactgttgat | 2400 |
| caggttttgg gaatacgagc tttggagtca gaaaaagaat tggaagaatt aaaaaagaga | 2460 |
| aatcttgact tagaaaatga tatattgtat atgagggccc accaagctct tcctcgagat | 2520 |
| tctgttgtag aagatttaca tttacaaaat agatacctcc aagaaaaact tcatgcttta | 2580 |
| gaaaaacagt tttcaaagga tacatattct aagccttcaa tttcaggaat agagtcagat | 2640 |
| gatcattgtc agagagaaca ggagcttcag aaggaaaact tgaagttgtc atctgaaaat | 2700 |
| attgaactga aatttcagct tgaacaagca aataaagatt tgccaagatt aaagaatcaa | 2760 |
| gtcagagatt tgaaggaaat gtgtgaattt cttaagaaag aaaaagcaga agttcagcgg | 2820 |
| aaacttggcc atgttagagg gtctggtaga agtggaaaga caatcccaga actggaaaaa | 2880 |
| accattggtt taatgaaaaa agtagttgaa aaagtccaga gagaaaatga acagttgaaa | 2940 |
| aaagcatcag gaatattgac tagtgaaaaa atggctaata ttgagcagga aaatgaaaaa | 3000 |
| ttgaaggctg aattagaaaa acttaaagct catcttgggc atcagttgag catgcactat | 3060 |
| gaatccaaga ccaaaggcac agaaaaaatt attgctgaaa atgaaaggct tcgtaaagaa | 3120 |
| cttaaaaaag aaactgatgc tgcagagaaa ttacggatag caaagaataa tttagagata | 3180 |
| ttaaatgaga agatgacagt tcaactagaa gagactggta agagattgca gtttgcagaa | 3240 |
| agcagaggtc cacagcttga aggtgctgac agtaagagct ggaaatccat tgtggttaca | 3300 |
| agaatgtatg aaaccaagtt aaaagaattg gaaactgata ttgccaaaaa aaatcaaagc | 3360 |
| attactgacc ttaaacagct tgtaaaagaa gcaacagaga gagaacaaaa agttaacaaa | 3420 |
| tacaatgaag accttgaaca acagattaag attcttaaac atgttcctga aggtgctgag | 3480 |
| acagagcaag gccttaaacg ggagcttcaa gttcttagat tagctaatca tcagctggat | 3540 |
| aaagagaaag cagaattaat ccatcagata gaagctaaca aggaccaaag tggagctgaa | 3600 |
| agcaccatac ctgatgctga tcaactaaag gaaaaaataa aagatctaga gacacagctc | 3660 |
| aaaatgtcag atctagaaaa gcagcatttg aaggaggaaa taagaagct gaaaaaagaa | 3720 |
| ctggaaaatt ttgatccttc atttttttgaa gaaattgaag atcttaagta taattacaag | 3780 |
| gaagaagtga agaagaatat tctcttagaa gagaaggtaa aaaaactttc agaacaattg | 3840 |
| ggagttgaat taactagccc tgttgctgct tctgaagagt ttgaagatga agaagaaagt | 3900 |
| cctgttaatt tcccccattta ctaa | 3924 |

<210> SEQ ID NO 32
<211> LENGTH: 1307

```
<212> TYPE: PRT
<213> ORGANISM: Homo sapiens

<400> SEQUENCE: 32

Gln Gln Ser Arg Asp Lys Glu Val Glu Ser Leu Arg Met Gln Leu Leu
1               5                   10                  15

Asp Tyr Gln Ala Gln Ser Asp Glu Lys Ser Leu Ile Ala Lys Leu His
            20                  25                  30

Gln His Asn Val Ser Leu Gln Leu Ser Glu Ala Thr Ala Leu Gly Lys
        35                  40                  45

Leu Glu Ser Ile Thr Ser Lys Leu Gln Lys Met Glu Ala Tyr Asn Leu
50                  55                  60

Arg Leu Glu Gln Lys Leu Asp Glu Lys Glu Gln Ala Leu Tyr Tyr Ala
65                  70                  75                  80

Arg Leu Glu Gly Arg Asn Arg Ala Lys His Leu Arg Gln Thr Ile Gln
            85                  90                  95

Ser Leu Arg Arg Gln Phe Ser Gly Ala Leu Pro Leu Ala Gln Gln Glu
        100                 105                 110

Lys Phe Ser Lys Thr Met Ile Gln Leu Gln Asn Asp Lys Leu Lys Ile
    115                 120                 125

Met Gln Glu Met Lys Asn Ser Gln Glu His Arg Asn Met Glu Asn
130                 135                 140

Lys Thr Leu Glu Met Glu Leu Lys Leu Lys Gly Leu Glu Glu Leu Ile
145                 150                 155                 160

Ser Thr Leu Lys Asp Thr Lys Gly Ala Gln Lys Val Ile Asn Trp His
            165                 170                 175

Met Lys Ile Glu Glu Leu Arg Leu Gln Glu Leu Lys Leu Asn Arg Glu
        180                 185                 190

Leu Val Lys Asp Lys Glu Ile Lys Tyr Leu Asn Asn Ile Ile Ser
    195                 200                 205

Glu Tyr Glu Arg Thr Ile Ser Ser Leu Glu Glu Glu Ile Val Gln Gln
210                 215                 220

Asn Lys Phe His Glu Glu Arg Gln Met Ala Trp Asp Gln Arg Glu Val
225                 230                 235                 240

Asp Leu Glu Arg Gln Leu Asp Ile Phe Asp Arg Gln Asn Glu Ile
            245                 250                 255

Leu Asn Ala Ala Gln Lys Phe Glu Glu Ala Thr Gly Ser Ile Pro Asp
        260                 265                 270

Pro Ser Leu Pro Leu Pro Asn Gln Leu Glu Ile Ala Leu Arg Lys Ile
    275                 280                 285

Lys Glu Asn Ile Arg Ile Ile Leu Glu Thr Arg Ala Thr Cys Lys Ser
290                 295                 300

Leu Glu Glu Lys Leu Lys Glu Lys Glu Ser Ala Leu Arg Leu Ala Glu
305                 310                 315                 320

Gln Asn Ile Leu Ser Arg Asp Lys Val Ile Asn Glu Leu Arg Leu Arg
            325                 330                 335

Leu Pro Ala Thr Ala Glu Arg Glu Lys Leu Ile Ala Glu Leu Gly Arg
        340                 345                 350

Lys Glu Met Glu Pro Lys Ser His His Thr Leu Lys Ile Ala His Gln
    355                 360                 365

Thr Ile Ala Asn Met Gln Ala Arg Leu Asn Gln Lys Glu Glu Val Leu
370                 375                 380

Lys Lys Tyr Gln Arg Leu Leu Glu Lys Ala Arg Glu Glu Gln Arg Glu
385                 390                 395                 400
```

-continued

Ile Val Lys Lys His Glu Glu Asp Leu His Ile Leu His His Arg Leu
            405                 410                 415

Glu Leu Gln Ala Asp Ser Ser Leu Asn Lys Phe Lys Gln Thr Ala Trp
            420                 425                 430

Asp Leu Met Lys Gln Ser Pro Thr Pro Val Pro Thr Asn Lys His Phe
            435                 440                 445

Ile Arg Leu Ala Glu Met Glu Gln Thr Val Ala Glu Gln Asp Asp Ser
450                 455                 460

Leu Ser Ser Leu Leu Val Lys Leu Lys Lys Val Ser Gln Asp Leu Glu
465                 470                 475                 480

Arg Gln Arg Glu Ile Thr Glu Leu Lys Val Lys Glu Phe Glu Asn Ile
            485                 490                 495

Lys Leu Gln Leu Gln Glu Asn His Glu Asp Glu Val Lys Lys Val Lys
            500                 505                 510

Ala Glu Val Glu Asp Leu Lys Tyr Leu Leu Asp Gln Ser Gln Lys Glu
            515                 520                 525

Ser Gln Cys Leu Lys Ser Glu Leu Gln Ala Gln Lys Glu Ala Asn Ser
            530                 535                 540

Arg Ala Pro Thr Thr Thr Met Arg Asn Leu Val Glu Arg Leu Lys Ser
545                 550                 555                 560

Gln Leu Ala Leu Lys Glu Lys Gln Gln Lys Ala Leu Ser Arg Ala Leu
            565                 570                 575

Leu Glu Leu Arg Ala Glu Met Thr Ala Ala Ala Glu Glu Arg Ile Ile
            580                 585                 590

Ser Ala Thr Ser Gln Lys Glu Ala His Leu Asn Val Gln Gln Ile Val
            595                 600                 605

Asp Arg His Thr Arg Glu Leu Lys Thr Gln Val Glu Asp Leu Asn Glu
            610                 615                 620

Asn Leu Leu Lys Leu Lys Glu Ala Leu Lys Thr Ser Lys Asn Arg Glu
625                 630                 635                 640

Asn Ser Leu Thr Asp Asn Leu Asn Asp Leu Asn Asn Glu Leu Gln Lys
                    645                 650                 655

Lys Gln Lys Ala Tyr Asn Lys Ile Leu Arg Glu Lys Glu Glu Ile Asp
            660                 665                 670

Gln Glu Asn Asp Glu Leu Lys Arg Gln Ile Lys Arg Leu Thr Ser Gly
            675                 680                 685

Leu Gln Gly Lys Pro Leu Thr Asp Asn Lys Gln Ser Leu Ile Glu Glu
            690                 695                 700

Leu Gln Arg Lys Val Lys Lys Leu Glu Asn Gln Leu Glu Gly Lys Val
705                 710                 715                 720

Glu Glu Val Asp Leu Lys Pro Met Lys Glu Lys Asn Ala Lys Glu Glu
                    725                 730                 735

Leu Ile Arg Trp Glu Glu Gly Lys Lys Trp Gln Ala Lys Ile Glu Gly
            740                 745                 750

Ile Arg Asn Lys Leu Lys Glu Lys Glu Gly Glu Val Phe Thr Leu Thr
            755                 760                 765

Lys Gln Leu Asn Thr Leu Lys Asp Leu Phe Ala Lys Ala Asp Lys Glu
            770                 775                 780

Lys Leu Thr Leu Gln Arg Lys Leu Lys Thr Thr Gly Met Thr Val Asp
785                 790                 795                 800

Gln Val Leu Gly Ile Arg Ala Leu Glu Ser Glu Lys Glu Leu Glu Glu
                    805                 810                 815

```
Leu Lys Lys Arg Asn Leu Asp Leu Glu Asn Asp Ile Leu Tyr Met Arg
            820                 825                 830

Ala His Gln Ala Leu Pro Arg Asp Ser Val Val Glu Asp Leu His Leu
        835                 840                 845

Gln Asn Arg Tyr Leu Gln Glu Lys Leu His Ala Leu Glu Lys Gln Phe
    850                 855                 860

Ser Lys Asp Thr Tyr Ser Lys Pro Ser Ile Ser Gly Ile Glu Ser Asp
865                 870                 875                 880

Asp His Cys Gln Arg Glu Gln Glu Leu Gln Lys Glu Asn Leu Lys Leu
            885                 890                 895

Ser Ser Glu Asn Ile Glu Leu Lys Phe Gln Leu Glu Gln Ala Asn Lys
        900                 905                 910

Asp Leu Pro Arg Leu Lys Asn Gln Val Arg Asp Leu Lys Glu Met Cys
    915                 920                 925

Glu Phe Leu Lys Lys Glu Lys Ala Glu Val Gln Arg Lys Leu Gly His
        930                 935                 940

Val Arg Gly Ser Gly Arg Ser Gly Lys Thr Ile Pro Glu Leu Glu Lys
945                 950                 955                 960

Thr Ile Gly Leu Met Lys Lys Val Val Glu Lys Val Gln Arg Glu Asn
            965                 970                 975

Glu Gln Leu Lys Lys Ala Ser Gly Ile Leu Thr Ser Glu Lys Met Ala
        980                 985                 990

Asn Ile Glu Gln Glu Asn Glu Lys  Leu Lys Ala Glu Leu  Glu Lys Leu
    995                 1000                 1005

Lys Ala  His Leu Gly His Gln  Leu Ser Met His Tyr  Glu Ser Lys
    1010                 1015                 1020

Thr Lys  Gly Thr Glu Lys Ile  Ile Ala Glu Asn Glu  Arg Leu Arg
    1025                 1030                 1035

Lys Glu  Leu Lys Lys Glu Thr  Asp Ala Ala Glu Lys  Leu Arg Ile
    1040                 1045                 1050

Ala Lys  Asn Asn Leu Glu Ile  Leu Asn Glu Lys Met  Thr Val Gln
    1055                 1060                 1065

Leu Glu  Glu Thr Gly Lys Arg  Leu Gln Phe Ala Glu  Ser Arg Gly
    1070                 1075                 1080

Pro Gln  Leu Glu Gly Ala Asp  Ser Lys Ser Trp Lys  Ser Ile Val
    1085                 1090                 1095

Val Thr  Arg Met Tyr Glu Thr  Lys Leu Lys Glu Leu  Glu Thr Asp
    1100                 1105                 1110

Ile Ala  Lys Lys Asn Gln Ser  Ile Thr Asp Leu Lys  Gln Leu Val
    1115                 1120                 1125

Lys Glu  Ala Thr Glu Arg Glu  Gln Lys Val Asn Lys  Tyr Asn Glu
    1130                 1135                 1140

Asp Leu  Glu Gln Gln Ile Lys  Ile Leu Lys His Val  Pro Glu Gly
    1145                 1150                 1155

Ala Glu  Thr Glu Gln Gly Leu  Lys Arg Glu Leu Gln  Val Leu Arg
    1160                 1165                 1170

Leu Ala  Asn His Gln Leu Asp  Lys Glu Lys Ala Glu  Leu Ile His
    1175                 1180                 1185

Gln Ile  Glu Ala Asn Lys Asp  Gln Ser Gly Ala Glu  Ser Thr Ile
    1190                 1195                 1200

Pro Asp  Ala Asp Gln Leu Lys  Glu Lys Ile Lys Asp  Leu Glu Thr
    1205                 1210                 1215

Gln Leu  Lys Met Ser Asp Leu  Glu Lys Gln His Leu  Lys Glu Glu
```

|  | 1220 |  | 1225 |  | 1230 |  |

Ile Lys Lys Leu Lys Lys Glu Leu Glu Asn Phe Asp Pro Ser Phe
1235                1240                1245

Phe Glu Glu Ile Glu Asp Leu Lys Tyr Asn Tyr Lys Glu Glu Val
1250                1255                1260

Lys Lys Asn Ile Leu Leu Glu Glu Lys Val Lys Lys Leu Ser Glu
1265                1270                1275

Gln Leu Gly Val Glu Leu Thr Ser Pro Val Ala Ala Ser Glu Glu
1280                1285                1290

Phe Glu Asp Glu Glu Glu Ser Pro Val Asn Phe Pro Ile Tyr
1295                1300                1305

<210> SEQ ID NO 33
<211> LENGTH: 3924
<212> TYPE: DNA
<213> ORGANISM: Homo sapiens

<400> SEQUENCE: 33

```
ttagtaaatg gggaaattaa caggactttc ttcttcatct tcaaactctt cagaagcagc      60
aacagggcta gttaattcaa ctcccaattg ttctgaaagt ttttttacct tctcttctaa     120
gagaatattc ttcttcactt cttccttgta attatactta agatcttcaa tttcttcaaa     180
aaatgaagga tcaaaatttt ccagttcttt tttcagcttc tttatttcct ccttcaaatg     240
ctgcttttct agatctgaca ttttgagctg tgtctctaga tcttttattt tttcctttag     300
ttgatcagca tcaggtatgg tgcttcagc tccactttgg tccttgttag cttctatctg      360
atggattaat tctgctttct ctttatccag ctgatgatta gctaatctaa gaacttgaag     420
ctcccgttta aggccttgct ctgtctcagc accttcagga acatgtttaa gaatcttaat     480
ctgttgttca aggtcttcat tgtatttgtt aacttttgt tctctctctg ttgcttcttt      540
tacaagctgt ttaaggtcag taatgctttg atttttttg gcaatatcag tttccaattc      600
ttttaacttg gtttcataca ttcttgtaac cacaatggat ttccagctct tactgtcagc     660
accttcaagc tgtggacctc tgcttctgc aaactgcaat ctcttaccag tctcttctag      720
ttgaactgtc atcttctcat ttaatatctc taaattattc tttgctatcc gtaatttctc     780
tgcagcatca gtttctttt taagttcttt acgaagcctt tcattttcag caataatttt      840
ttctgtgcct ttggtcttgg attcatagtg catgctcaac tgatgcccaa gatgagcttt     900 aagttttct aattcagcct tcaattttc attttcctgc tcaatattag ccatttttc       960 actagtcaat attcctgatg ctttttcaa ctgttcattt tctctctgga cttttcaac     1020 tactttttc attaaaccaa tggttttttc cagttctggg attgtctttc cacttctacc     1080
agaccctcta acatggccaa gtttccgctg aacttctgct ttttctttct taagaaattc     1140
acacatttcc ttcaaatctc tgacttgatt ctttaatctt ggcaaatctt tatttgcttg     1200
ttcaagctga aatttcagtt caatatttc agatgacaac ttcaagtttt ccttctgaag     1260
ctcctgttct ctctgacaat gatcatctga ctctattcct gaaattgaag gcttagaata     1320
tgtatccttt gaaaactgtt tttctaaagc atgaagtttt tcttggaggt atctattttg     1380
taaatgtaaa tcttctacaa cagaatctcg aggaagagct tggtgggccc tcatatacaa     1440
tatatcattt tctaagtcaa gatttctctt ttttaattct tccaattctt tttctgactc     1500
caaagctcgt attcccaaaa cctgatcaac agtcatgcca gttgttttta gtttcctctg     1560
caaagtaagt ttctctttat cggctttggc aaaaagatcc ttcaaagtat tcaactgctt     1620
```

```
tgttaaagta aagacttccc cctctttctc ttttaacttg tttcgaattc cttctatttt   1680
ggcttgccac ttttaccctt cttcccacct aattaattct tctttagcat tcttttcttt   1740
cataggtttt aggtctactt cctccacctt tccctctaat tggttctcta gttttttaac   1800
tttcctttgg agttcttcaa ttagactttg tttattatct gtcaggggtt tgccctgtaa   1860
tccactggtt agtcttttaa tttgcctttt cagttcatca ttctcttgat caatttcctc   1920
tttctctcta agtattttat tataggcttt tgtttctttt tgcagttcat tatttaagtc   1980
attcaaatta tcagttagtg agttttctct gttttactt gttttaagtg cttctttcaa    2040
ttttaaaga ttttcattta aatcttcaac ttgtgtcttt agctctctag tatgtcgatc     2100
aacgatttgt tgaacattga gatgggcctc tttttgagaa gttgcagaaa taatacgttc   2160
ttcagcagct gctgtcattt ctgcccggag ttctaaaagt gcccgactaa gtgctttctg   2220
ttgtttctcc ttcaaggcta attggctctt tagccgttct actagatttc tcattgtagt   2280
tgttggagct cttgaatttg cttcttttg agcctgaagt tcagatttta aacactgtga    2340
ctccttttgt gactggtcca gaagatactt taaatcctct acttccgctt ttactttttt   2400
cacttcatct tcatggtttt cttgaagctg taatttgata ttttcaaatt cttttacttt   2460
taattcagtg atttctcttt gtctctccaa atcttgtgat actttcttta gtttgaccaa   2520
gagtgaggaa agagagtcat cttgttctgc tactgtctgt tccatctcag ccagacgaat   2580
aaaatgcttg ttggtaggaa ctggagtggg agactgtttc attaaatccc aagccgtttg   2640
tttgaattta tttagtgaac tatcagcctg tagttctaat ctgtgatgaa gaatatgaag   2700
gtcttcctca tgtttcttca caatttctct ttgctcctct ctggcttttt ctagaagacg   2760
ttgatacttc tttaatactt cttcttttg atttaacctt gcttgcatgt ttgcaatggt    2820
ttgatgagca attttcaatg tgtggtgaga ttttggttcc atctcttttc tgcctagctc   2880
agctatgagc ttttctcttt ctgcagtggc aggcaatcga agcctcagtt cattgattac   2940
tttgtctctt gacagtatat tttgttctgc taaccttaaa gcagattctt tctcttttag   3000
tttctcttct agtgatttgc aagttgcccg tgtttctaga attattcgaa tgttctcctt   3060
aattttcctt agagcgatct caagttgatt tggaaggggc aaactagggt cagggattga   3120
tcctgtagct tcttcaaact tttgtgccgc atttagtatt tcattttgct gacggtcaaa   3180
aatgtctagt tggcgttcca ggtcaacttc tctttgatcc caggccattt gtctttcttc   3240
atgaaacttg ttctgttgca caatttcttc ttcaagactg ctgattgtac gttcatattc   3300
agaaattatg ttattcaaat attttatttc ttctttatcc ttgactaatt cccgatttag   3360
tttaagttct tgaagacgaa gttcttctat tttcatatgc cagttgatta ccttttgggc   3420
tcctttggta tccttaaag tgcttattaa ctcttccagg ccctttaatt ttaattccat    3480
ctccaatgtt ttgttctcca tatttctatg tccttgttga gaattttttca tttcttgcat  3540
tatcttaagt ttgtcatttt gtagttgaat cattgttttg gagaactttt cctgttgtgc   3600
caagggtaaa gctccactaa actgtcgtcg tagagactga attgtttggc gcagatgttt   3660
tgctctgttt cttccctcca aacgagcata atagagagcc tgttctttt catcaagttt    3720
ctgctctaag cgcaagttgt aggcctccat cttctgcagt ttagatgtaa ttgactccaa   3780
cttaccaaga gcagtagcct cactcagttg aagagagaca ttatgttggt gcaacttggc   3840
aatgagcgac ttttcatcag actgtgcctg atagtctagc agttgcattc tgagggactc   3900
tacttccttg tccctagatt gttg                                          3924
```

```
<210> SEQ ID NO 34
<211> LENGTH: 3888
<212> TYPE: DNA
<213> ORGANISM: Artificial sequence
<220> FEATURE:
<223> OTHER INFORMATION: Sequence of expression cassette-CMV-mouse Myo
      tail-polyA

<400> SEQUENCE: 34
acgcgtggag ctagttatta atagtaatca attacggggt cattagttca tagcccatat      60
atggagttcc gcgttacata acttacggta atggcccgc  ctggctgacc gcccaacgac     120
ccccgcccat tgacgtcaat aatgacgtat gttcccatag taacgtcaat agggactttc     180
cattgacgtc aatgggtgga gtatttacgg taaactgccc acttggcagt acatcaagtg     240
tatcatatgc caagtacgcc ccctattgac gtcaatgacg taaatggccc gcctggcat     300
tatgcccagt acatgacctt atgggacttt cctacttggc agtacatcta cgtattagtc     360
atcgctatta ccatggtgat gcggttttgg cagtacatca atgggcgtgg atagcggttt     420
gactcacggg gatttccaag tctccacccc attgacgtca atgggagttt gttttgcacc     480
aaaatcaacg ggactttcca aatgtcgta acaactccgc cccattgacg caaatgggcg     540
gtaggcgtgt acggtgggag gtctatataa gcagagctcg tttagtgaac cgtcagatcg     600
cctggagacg ccatccacgc tgttttgacc tccatagaag acaccgggac cgatccagcc     660
tccgcggcca ccatgttggc agagcaaaat attctgtcaa gagacaaagt aatcaatgaa     720
ctgaggcttc gattgcctgc cacggctgat cgagaaaaac ttatagctga gctagaaaga     780
aaagagctgg agccgaaatc tcatcacaca atgaaaattg cccaccaaac tattgccaac     840
atgcaggcaa ggttaaatca caggaagaa gtattgaaga ataccagca ccttctggag      900
aaggccagag aggagcaaag agaaattgtt aagaagcatg aggaagacct tcatgttctt     960
catcacaaat tagaacaaca ggccgataat tcactcaata aattcagaca gacagctcag    1020
gatttactta agcagtctcc tgctccagtt cccaccaaca acatttcat cgtctggcc    1080
gagatggagc agacagtagc agaacaagat gactctctgt cctcactttt gaccaaacta    1140
aagaaagtat caaagatttt ggaaaaacaa aagaaatca ctgagttaaa agtcagagag     1200
tttgaaaata ccaaactacg gctccaagaa actcatgcca gtgaggtaaa gaaagtgaaa    1260
gcagaggtag aggacttaag gcatgctcta gcccaagcac acaaggactc ccagagttta    1320
aagtctgaac tccaggctca gaaagaagca aactccagag ctccaacaac cacaatgagg    1380
aatcttgtag acaggctaaa gagccaacta gccttgaaag agaagcaaca aaaggcactt    1440
agtcgagccc tgttggaact tcggtcggaa atgacagcag cagctgagga acgtataatc    1500
gctgtaactt ctcaaaaaga ggcaaatctc aatgttcaac aagttgttga gcgccatact    1560
agagagctaa agtcacaaat tgaagattta aatgaaaatc ttttaaaatt gaagaagct    1620
cttaaaacaa gtaagaacaa agaaaattca ctagctgatg atttaaatga attaaataat    1680
gaactgcaaa aaaagcaaaa agcttataat aaaatcctta gagagaaaga tggaattgat    1740
caagaaaatg atgaactgag aagacagatt aaaagactgt ccagtggact gcagagcaaa    1800
actttgatag ataacaagca aagtttaatc gatgaacttc aaaagaaagt taaaaaactt    1860
gaaagccaac tggaaagaaa ggtggatgac gtagacataa agccggtgaa ggaaagagt     1920
agtaaagaag aattaattag gtgggaagaa ggtaagaaat ggcaaaccaa gtgagggga    1980
ctacgaaaca gactaaagga gaaggaagga gaagcccacg gcctggcaaa gcagctgaat    2040
accttaaagg aacttttgc caaagctgat aaagagaaac ttacttgca gaagaactg     2100
```

```
aaaacaacag gaatgactgt tgaccaggtt ttaggagtgc gagctttgga atctgaaaaa      2160
gagttggaag agctaaaaaa gaaaaatctg gacctagaaa atgacatatt atacatgagg      2220
acccagcagg ctcttccacg agattctgtt gtggaagact tacatttaca aaataaatac      2280
cttcaagaaa aacttcatac tttagaaaaa aaactttcaa aggagaaata ttctcagtct      2340
ttgacttcag aaatagagtc agatgatcac tgtcaaaaag aacaagaact tcagaaggaa      2400
aatttgaagt tgtcatctga aaacatcgag ctgaaatttc aacttgaaca agcaaataaa      2460
gatttgccaa gactaaagaa tcaagtgaaa gatttgaagg aaatgtgtga atttcttaag      2520
aaaggaaaac tggaacttga gcggaagctt ggtcaggtca gaggggctgg tagaagtggg      2580
aagacaatcc cagaactaga aaaaaccatt gggttaatga agaaagtagt tgaaaaagtc      2640
caaagagaaa atgaacaatt gaaaaaggca tcaggaatac tgactagtga aaaaatggct      2700
actattgagg aagaaaatag aaacttaaag gctgaactag aaaagcttaa agctcacttt      2760
ggacgtcagt tgagtatgca gtttgaatct aagaacaaag gtactgagaa aattgttgcc      2820
gaaaatgaac ggcttcggaa agaacttaag aaagaaatag aagcctctga gaaactgcgg      2880
atagctaaga caacttaga gctggtgaac gacaagatgg cagctcaact cgaagaaact      2940
gggaagagac tacagtttgc agaaagtaga gccccacagc tggaaggtgc tgacagcaag      3000
agctggaagt caattgtggt ctcaagagtg tatgagacca agatgaaaga gcttgaaagt      3060
gacattgcca aaagaatca agtatcact gaccttaaac agcttgtaag agaagcaaca      3120
gagagagaac agaaagctaa gaaatacact gaagaccttg aacaacagat tgagatcctc      3180
aaaaatgttc ctgaaggtgc cgagacagag caagagctta tacgggaact ccagcttctt      3240
agattagcca ataatcagat ggataaagaa agggcagaat taatccatca gatagaaatt      3300
aacaaggacc aaaccagagc tgacagtagc atacctgatt ctgatcaact aaaggaaaag      3360
ataaatgacc tggagacaca actcagaaag ttggagctag aaaagcaaca ttcgaaggag      3420
gaagttaaaa agctgaaaaa agaactggaa aattttgatc cttcattttt tgaagaaatt      3480
gaagacctga gtataatta aaggaagaa gtgaaaaaga atatcctatt agaagagaag      3540
ctaaaaaaac tgtcggaaca gtttggattt gaactgccta gtcctcttgc tgcttctgaa      3600
cactcggaag atggagaaag tcctcatagt ttccctattt attagagatc tacatctcgc      3660
tttcttgctg tccaatttct attaaaggtt cctttgttcc ctaagtccaa ctactaaact      3720
gggggatatt atgaagggcc ttgagcatct ggattctgcc taataaaaaa catttatttt      3780
cattgcaatg atgtatttaa attatttctg aatattttac taaaagggaa atgtgggagg      3840
tcagtgcatt taaaacataa agaaagtagg taaccacgtg cggaccga                  3888
```

<210> SEQ ID NO 35
<211> LENGTH: 3891
<212> TYPE: DNA
<213> ORGANISM: Artificial sequence
<220> FEATURE:
<223> OTHER INFORMATION: Sequence of expression cassette-CMV-human Myo
      tail-polyA

<400> SEQUENCE: 35

```
acgcgtggag ctagttatta atagtaatca attacggggt cattagttca tagcccatat       60
atggagttcc gcgttacata acttacggta aatggcccgc ctggctgacc gcccaacgac      120
ccccgcccat tgacgtcaat aatgacgtat gttcccatag taacgtcaat agggactttc      180
cattgacgtc aatgggtgga gtatttacgg taaactgccc acttggcagt acatcaagtg      240
```

```
tatcatatgc caagtacgcc ccctattgac gtcaatgacg gtaaatggcc cgcctggcat    300
tatgcccagt acatgacctt atgggacttt cctacttggc agtacatcta cgtattagtc    360
atcgctatta ccatggtgat gcggttttgg cagtacatca atgggcgtgg atagcggttt    420
gactcacggg gatttccaag tctccacccc attgacgtca atgggagttt gttttgcacc    480
aaaatcaacg ggactttcca aaatgtcgta caactccgc cccattgacg caaatgggcg    540
gtaggcgtgt acggtgggag gtctatataa gcagagctcg tttagtgaac cgtcagatcg    600
cctggagacg ccatccacgc tgttttgacc tccatagaag acaccgggac cgatccagcc    660
tccgcggcca ccatgttagc agaacaaaat atactgtcaa gagacaaagt aatcaatgaa    720
ctgaggcttc gattgcctgc cactgcagaa agagaaaagc tcatagctga gctaggcaga    780
aaagagatgg aaccaaaatc tcaccacaca ttgaaaattg ctcatcaaac cattgcaaac    840
atgcaagcaa ggttaaatca aaaagaagaa gtattaaaga agtatcaacg tcttctagaa    900
aaagccagag aggagcaaag agaaattgtg aagaaacatg aggaagacct tcatattctt    960
catcacagat tagaactaca ggctgatagt tcactaaata aattcaaaca aacggcttgg   1020
gatttaatga acagtctcc cactccagtt cctaccaaca agcattttat tcgtctggct    1080
gagatggaac agacagtagc agaacaagat gactctcttt cctcactctt ggtcaaacta   1140
aagaaagtat cacaagattt ggagagacaa agagaaatca ctgaattaaa agtaaaagaa   1200
tttgaaaata tcaaattaca gcttcaagaa aaccatgaag atgaagtgaa aaaagtaaaa   1260
gcggaagtag aggatttaaa gtatcttctg gaccagtcac aaaaggagtc acagtgttta   1320
aaatctgaac ttcaggctca aaaagaagca aattcaagag ctccaacaac tacaatgaga   1380
aatctagtag aacggctaaa gagccaatta gccttgaagg agaaacaaca gaaagcactt   1440
agtcgggcac ttttagaact ccgggcagaa atgacagcag ctgctgaaga acgtattatt   1500
tctgcaactt ctcaaaaaga ggcccatctc aatgttcaac aaatcgttga tcgacatact   1560
agagagctaa agacacaagt tgaagattta aatgaaaatc ttttaaaatt gaaagaagca   1620
cttaaaacaa gtaaaaacag agaaaactca ctaactgata atttgaatga cttaaataat   1680
gaactgcaaa agaaacaaaa agcctataat aaaatactta gagagaaaga ggaaattgat   1740
caagagaatg atgaactgaa aaggcaaatt aaaagactaa ccagtggatt acagggcaaa   1800
cccctgacag ataataaaca aagtctaatt gaagaactcc aaaggaaagt taaaaaacta   1860
gagaaccaat tagagggaaa ggtggaggaa gtagacctaa aacctatgaa agaaaagaat   1920
gctaaagaag aattaattag gtgggaagaa ggtaaaagt ggcaagccaa aatagaagga   1980
attcgaaaca gttaaaaga gaaagagggg gaagtctta ctttaacaaa gcagttgaat    2040
actttgaagg atcttttgc caaagccgat aaagagaaac ttactttgca gaggaaacta   2100
aaaacaactg gcatgactgt tgatcaggtt ttgggaatac gagctttgga gtcagaaaaa   2160
gaattggaag aattaaaaaa gagaaatctt gacttagaaa atgatatatt gtatatgagg   2220
gcccaccaag ctcttcctcg agattctgtt gtagaagatt tacatttaca aaatagatac   2280
ctccaagaaa aacttcatgc tttagaaaaa cagttttcaa aggatacata ttctaagcct   2340
tcaatttcag gaatagagtc agatgatcat tgtcagagag aacaggagct tcagaaggaa   2400
aacttgaagt tgtcatctga aaatattgaa ctgaaatttc agcttgaaca agcaaataaa   2460
gatttgccaa gattaaagaa tcaagtcaga gatttgaagg aaatgtgtga atttcttaag   2520
aaagaaaaag cagaagttca gcggaaactt ggccatgtta gagggtctgg tagaagtgga   2580
```

```
aagacaatcc cagaactgga aaaaaccatt ggtttaatga aaaagtagt tgaaaaagtc      2640 cagagagaaa atgaacagtt gaaaaaagca tcaggaatat tgactagtga aaaaatggct    2700
aatattgagc aggaaaatga aaaattgaag gctgaattag aaaaacttaa agctcatctt    2760
gggcatcagt tgagcatgca ctatgaatcc aagaccaaag gcacagaaaa aattattgct    2820
gaaaatgaaa ggcttcgtaa agaacttaaa aaagaaactg atgctgcaga gaaattacgg    2880
atagcaaaga ataatttaga gatattaaat gagaagatga cagttcaact agaagagact    2940
ggtaagagat tgcagtttgc agaaagcaga ggtccacagc ttgaaggtgc tgacagtaag    3000
agctggaaat ccattgtggt tacaagaatg tatgaaacca agttaaaaga attggaaact    3060
gatattgcca aaaaaaatca aagcattact gaccttaaac agcttgtaaa agaagcaaca    3120
gagagagaac aaaaagttaa caaatacaat gaagaccttg aacaacagat taagattctt    3180
aaacatgttc ctgaaggtgc tgagacagag caaggcctta acgggagct tcaagttctt     3240 agattagcta atcatcagct ggataaagag aaagcagaat taatccatca gatagaagct    3300
aacaaggacc aaagtggagc tgaaagcacc ataccctgatg ctgatcaact aaaggaaaaa   3360
ataaaagatc tagagacaca gctcaaaatg tcagatctag aaaagcagca tttgaaggag    3420
gaaataaaga agctgaaaaa agaactggaa aattttgatc cttcattttt tgaagaaatt    3480
gaagatctta gtataatta caaggaagaa gtgaagaaga atattctctt agaagagaag     3540
gtaaaaaaac tttcagaaca attgggagtt gaattaacta gccctgttgc tgcttctgaa    3600
gagtttgaag atgaagaaga aagtcctgtt aatttcccca tttactaaag atctacatct    3660 cgcttcttg ctgtccaatt tctattaaag gttcctttgt tccctaagtc caactactaa    3720
actgggggat attatgaagg gccttgagca tctggattct gcctaataaa aaacatttat   3780
tttcattgca atgatgtatt taaattattt ctgaatattt tactaaaaag ggaatgtggg    3840
aggtcagtgc atttaaaaca taagaaagt aggtaaccac gtgcggaccg a             3891
```

<210> SEQ ID NO 36  
<211> LENGTH: 1818  
<212> TYPE: DNA  
<213> ORGANISM: Artificial sequence  
<220> FEATURE:  
<223> OTHER INFORMATION: Sequence of expression cassette-CMV-mouse DSD-polyA

<400> SEQUENCE: 36

```
acgcgtggag ctagttatta atagtaatca attacggggt cattagttca tagcccatat      60
atggagttcc gcgttacata acttacggta aatggcccgc ctggctgacc gcccaacgac    120
ccccgcccat tgacgtcaat aatgacgtat gttcccatag taacgtcaat agggactttc    180
cattgacgtc aatgggtgga gtatttacgg taaactgccc acttggcagt acatcaagtg    240
tatcatatgc caagtacgcc ccctattgac gtcaatgacg gtaaatggcc cgcctggcat    300
tatgcccagt acatgacctt atgggacttt cctacttggc agtacatcta cgtattagtc    360
atcgctatta ccatggtgat gcggttttgg cagtacatca atgggcgtgg atagcggttt    420
gactcacggg gatttccaag tctccacccc attgacgtca atgggagttt gttttgcacc    480
aaaatcaacg ggactttcca aaatgtcgta caactccgc cccattgacg caaatgggcg     540
gtaggcgtgt acggtgggag gtctatataa gcagagctcg tttagtgaac cgtcagatcg    600
cctggagacg ccatccacgc tgttttgacc tccatagaag acaccgggac cgatccagcc    660
tccgcggcca ccatggattt acttaagcag tctcctgctc cagttcccac caacaaacat    720
```

```
ttcattcgtc tggccgagat ggagcagaca gtagcagaac aagatgactc tctgtcctca    780
cttttgacca aactaaagaa agtatcaaaa gatttggaaa aacaaaaaga aatcactgag    840
ttaaaagtca gagagtttga aaataccaaa ctacggctcc aagaaactca tgccagtgag    900
gtaaagaaag tgaaagcaga ggtagaggac ttaaggcatg ctctagccca agcacacaag    960
gactcccaga gtttaaagtc tgaactccag gctcagaaag aagcaaactc cagagctcca   1020
acaaccacaa tgaggaatct tgtagacagg ctaaagagcc aactagcctt gaaagagaag   1080
caacaaaagg cacttagtcg agccctgttg gaacttcggt cggaaatgac agcagcagct   1140
gaggaacgta taatcgctgt aacttctcaa aaagaggcaa atctcaatgt tcaacaagtt   1200
gttgagcgcc atactagaga gctaaagtca caaattgaag atttaaatga aaatctttta   1260
aaattgaaag aagctcttaa aacaagtaag aacaaagaaa attcactagc tgatgattta   1320
aatgaattaa ataatgaact gcaaaaaaag caaaaagctt ataataaaat ccttagagag   1380
aaagatggaa ttgatcaaga aaatgatgaa ctgagaagac agattaaaag actgtccagt   1440
ggactgcaga gcaaaacttt gatagataac aagcaaagtt taatcgatga acttcaaaag   1500
aaagttaaaa aacttgaaag ccaactggaa agaaaggtgg atgacgtaga cataaagccg   1560
gtgaaggaaa agtagagatc tacatctcgc tttcttgctg tccaatttct attaaaggtt   1620
cctttgttcc ctaagtccaa ctactaaact gggggatatt atgaagggcc ttgagcatct   1680
ggattctgcc taataaaaaa catttatttt cattgcaatg atgtatttaa attatttctg   1740
aatatttttac taaaaaggga atgtgggagg tcagtgcatt taaaacataa agaaagtagg   1800
taaccacgtg cggaccga                                                  1818

<210> SEQ ID NO 37
<211> LENGTH: 1818
<212> TYPE: DNA
<213> ORGANISM: Artificial sequence
<220> FEATURE:
<223> OTHER INFORMATION: Sequence of expression cassette-CMV-human
      DSD-polyA

<400> SEQUENCE: 37
acgcgtggag ctagttatta atagtaatca attacggggt cattagttca tagcccatat     60
atggagttcc gcgttacata acttacggta aatggcccgc ctggctgacc gcccaacgac    120
ccccgcccat tgacgtcaat aatgacgtat gttcccatag taacgtcaat agggactttc    180
cattgacgtc aatgggtgga gtatttacgg taaactgccc acttggcagt acatcaagtg    240
tatcatatgc caagtacgcc ccctattgac gtcaatgacg gtaaatggcc cgcctggcat    300
tatgcccagt acatgacctt atgggacttt cctacttggc agtacatcta cgtattagtc    360
atcgctatta ccatggtgat gcggttttgg cagtacatca atgggcgtgg atagcggttt    420
gactcacggg gatttccaag tctccacccc attgacgtca atgggagttt gttttgcacc    480
aaaatcaacg ggactttcca aaatgtcgta acaactccgc cccattgacg caaatgggcg    540
gtaggcgtgt acggtgggag gtctatataa gcagagctcg tttagtgaac cgtcagatcg    600
cctggagacg ccatccacgc tgttttgacc tccatagaag acaccgggac cgatccagcc    660
tccgcggcca ccatggattt aatgaaacag tctcccactc cagttcctac caacaagcat    720
tttattcgtc tggctgagat ggaacagaca gtagcagaac aagatgactc tctttcctca    780
ctcttggtca aactaaagaa agtatcacaa gatttggaga gacaaagaga aatcactgaa    840
ttaaaagtaa aagaatttga aaatatcaaa ttacagcttc aagaaaacca tgaagatgaa    900
```

```
gtgaaaaaag taaaagcgga agtagaggat ttaaagtatc ttctggacca gtcacaaaag    960
gagtcacagt gtttaaaatc tgaacttcag gctcaaaaag aagcaaattc aagagctcca   1020
acaactacaa tgagaaatct agtagaacgg ctaaagagcc aattagcctt gaaggagaaa   1080
caacagaaag cacttagtcg ggcactttta gaactccggg cagaaatgac agcagctgct   1140
gaagaacgta ttatttctgc aacttctcaa aaagaggccc atctcaatgt tcaacaaatc   1200
gttgatcgac atactagaga gctaaagaca caagttgaag attttaaatga aaatctttta   1260
aaattgaaag aagcacttaa aacaagtaaa aacagagaaa actcactaac tgataaatttg  1320
aatgacttaa ataatgaact gcaaaagaaa caaaaagcct ataataaaat acttagagag   1380
aaagaggaaa ttgatcaaga gaatgatgaa ctgaaaaggc aaattaaaag actaaccagt   1440
ggattacagg gcaaacccct gacagataat aaacaaagtc taattgaaga actccaaagg   1500
aaagttaaaa aactagagaa ccaattagag ggaaaggtgg aggaagtaga cctaaaacct   1560
atgaaagaaa agtagagatc tacatctcgc tttcttgctg tccaatttct attaaaggtt   1620
cctttgttcc ctaagtccaa ctactaaact ggggatatt atgaagggcc ttgagcatct    1680
ggattctgcc taataaaaaa catttatttt cattgcaatg atgtatttaa attatttctg   1740
aatatttac taaaaggga atgtgggagg tcagtgcatt taaaacataa agaaagtagg     1800
taaccacgtg cggaccga                                                 1818

<210> SEQ ID NO 38
<211> LENGTH: 4842
<212> TYPE: DNA
<213> ORGANISM: Artificial sequence
<220> FEATURE:
<223> OTHER INFORMATION: Sequence of expression cassette-CMV-mouse
      C-terminal-polyA

<400> SEQUENCE: 38
acgcgtggag ctagttatta atagtaatca attacggggt cattagttca tagcccatat     60
atggagttcc gcgttacata acttacggta aatggcccgc ctggctgacc gcccaacgac    120
ccccgcccat tgacgtcaat aatgacgtat gttcccatag taacgtcaat agggactttc    180
cattgacgtc aatgggtgga gtatttacgg taaactgccc acttggcagt acatcaagtg    240
tatcatatgc caagtacgcc ccctattgac gtcaatgacg gtaaatggcc cgcctggcat    300
tatgcccagt acatgacctt atgggacttt cctacttggc agtacatcta cgtattagtc    360
atcgctatta ccatggtgat gcggttttgg cagtacatca atgggcgtgg atagcggttt    420
gactcacggg gatttccaag tctccacccc attgacgtca atgggagttt gttttgcacc    480
aaaatcaacg ggactttcca aaatgtcgta acaactccgc cccattgacg caaatgggcg    540
gtaggcgtgt acggtgggag gtctatataa gcagagctcg tttagtgaac cgtcagatcg    600
cctggagacg ccatccacgc tgttttgacc tccatagaag acaccgggac cgatccagcc    660
tccgcggcca ccatgcaaca acagtccagg gaaaaggaag tggaatccct cagaacgcag    720
ctgctggact ccaggcaca atctgacgaa aaggctctaa ttgccaaatt gcaccaacat    780
gttgtctctc ttcaaattag tgaggccact gccctcggta agttagagtc agttacgtcc    840
aaactccaga gatggaagc ctacaatttg cgcttagaac agaaactgga tgaaaaagag    900
caggcgctct actatgctcg tttggaaggt agaaacagag caaaacacct gcgccaaacc    960
attcagtcgc ttcgaagaca gttcagtgga gctctacccct tagcacagca ggaaaagttc   1020
tccaaaacga tgattcagtt gcaaaatgac aaacttaaga taatgcaaga aatgaagaat   1080
```

```
tcgcaacagg aacacagaaa tatggaaaac aaaacactgg agttggaatt aaaattaaaa    1140
ggcttagaag aattgatcag tactttaaag gatgccaggg gagcccagaa ggtaatcaat    1200
tggcatgtga aaatagaaga acttcgcctc caagaactta agctaaatag agaactagtc    1260
aagggtaaag aagaaatcaa atatttgaat aatatcatct ctgaatatga gcatacaatc    1320
aacagtctag aggaagaaat tgttcagcaa agcaagttcc atgaagaaag acagatggct    1380
tgggatcaaa gagaagttga gctggaacgc cagttagaca tttttgatca tcagcaaaat    1440
gaaatactca gtgcagcaca aaagtttgaa gactctacag gatcaatgcc agaccccagc    1500
ttgcctcttc caaaccaact tgaaattgct ctaagaaaaa ttaaggagaa tattcaagta    1560
attcttaaaa cacaagcaac ttgcaagtca ctagaagaga aactaaaaga aaaagaatct    1620
gctttacggt tggcagagca aaatattctg tcaagagaca aagtaatcaa tgaactgagg    1680
cttcgattgc ctgccacggc tgatcgagaa aaacttatag ctgagctaga agaaaagag    1740 ctggagccga aatctcatca cacaatgaaa attgcccacc aaactattgc caacatgcag    1800
gcaaggttaa atcacaagga gaagtattg aagaaatacc agcaccttct ggagaaggcc    1860
agagaggagc aaagagaaat tgttaagaag catgaggaag accttcatgt tcttcatcac    1920
aaattagaac aacaggccga taattcactc aataaattca gacagacagc tcaggattta    1980
cttaagcagt ctcctgctcc agttcccacc aacaaacatt tcattcgtct ggccgagatg    2040
gagcagacag tagcagaaca agatgactct ctgtcctcac ttttgaccaa actaaagaaa    2100
gtatcaaaag atttggaaaa acaaaaagaa atcactgagt taaaagtcag agagtttgaa    2160
aataccaaac tacggctcca agaaactcat gccagtgagg taaagaaagt gaaagcagag    2220
gtagaggact taaggcatgc tctagcccaa gcacacaagg actcccagag tttaaagtct    2280
gaactccagg ctcagaaaga agcaaactcc agagctccaa caaccacaat gaggaatctt    2340
gtagacaggc taaagagcca actagccttg aaagagaagc aacaaaaggc acttagtcga    2400
gccctgttgg aacttcggtc ggaaatgaca gcagcagctg aggaacgtat aatcgctgta    2460
acttctcaaa aagaggcaaa tctcaatgtt caacaagttg ttgagcgcca tactagagag    2520
ctaaagtcac aaattgaaga tttaaatgaa aatcttttaa aattgaaaga agctcttaaa    2580
acaagtaaga acaaagaaaa ttcactagct gatgatttaa atgaattaaa taatgaactg    2640
caaaaaaagc aaaaagctta taataaaatc cttagagaga aagatggaat tgatcaagaa    2700
aatgatgaac tgaagagaca gattaaaaga ctgtccagtg gactgcagag caaaactttg    2760
atagataaca agcaaagttt aatcgatgaa cttcaaaaga agttaaaaaa acttgaaagc    2820
caactggaaa gaaaggtgga tgacgtagac ataaagccgg tgaaggaaaa gagtagtaaa    2880
gaagaattaa ttaggtggga agaaggtaag aaatggcaaa ccaaagtaga gggactacga    2940
aacagactaa aggagaagga aggagaagcc cacggcctgg caaagcagct gaataccta    3000 aaggaacttt ttgccaaagc tgataaagag aaacttactt tgcagaagaa actgaaaaca    3060
acaggaatga ctgttgacca ggttttagga gtgcgagctt ggaatctgaa aaagagttg    3120 gaagagctaa aaagaaaaa tctggaccta gaaaatgaca tattatacat gaggacccag    3180
caggctcttc cacgagattc tgttgtggaa gacttacatt tacaaaataa atacattcaa    3240
gaaaaacttc atactttaga aaaaaaactt caaggagaa atattctca gtctttgact    3300 tcagaaatag agtcagatga tcactgtcaa aagaacaag aacttcagaa ggaaaatttg    3360
aagttgtcat ctgaaaacat cgagctgaaa tttcaacttg aacaagcaaa taagattttg    3420
ccaagactaa agaatcaagt gaaagatttg aaggaaatgt gtgaatttct taagaaagga    3480
```

```
aaactggaac ttgagcggaa gcttggtcag gtcagagggg ctggtagaag tgggaagaca   3540
atcccagaac tagaaaaaac cattgggtta atgaagaaag tagttgaaaa agtccaaaga   3600
gaaaatgaac aattgaaaaa ggcatcagga atactgacta gtgaaaaaat ggctactatt   3660
gaggaagaaa atagaaactt aaaggctgaa ctagaaaagc ttaaagctca ctttggacgt   3720
cagttgagta tgcagtttga atctaagaac aaaggtactg agaaaattgt tgccgaaaat   3780
gaacggcttc ggaaagaact taagaaagaa atagaagcct ctgagaaact gcggatagct   3840
aagaacaact tagagctggt gaacgacaag atggcagctc aactcgaaga aactgggaag   3900
agactacagt ttgcagaaag tagagcccca cagctggaag tgctgacag  caagagctgg   3960 aagtcaattg tggtctcaag agtgtatgag accaagatga aagagcttga aagtgacatt   4020
gccaaaaaga atcaaagtat cactgacctt aaacagcttg taagagaagc aacagagaga   4080
gaacagaaag ctaagaaata cactgaagac cttgaacaac agattgagat cctcaaaaat   4140
gttcctgaag gtgccgagac agagcaagag cttatacggg aactccagct tcttagatta   4200
gccaataatc agatggataa agaaagggca gaattaatcc atcagataga aattaacaag   4260
gaccaaacca gagctgacag tagcatacct gattctgatc aactaaagga aaagataaat   4320
gacctggaga cacaactcag aaagttggag ctagaaaagc aacattcgaa ggaggaagtt   4380
aaaaagctga aaaagaact ggaaaatttt gatccttcat tttttgaaga aattgaagac   4440
ctgaagtata attataagga agaagtgaaa agaatatcc tattagaaga gaagctaaaa   4500
aaactgtcgg aacagtttgg atttgaactg cctagtcctc ttgctgcttc tgaacactcg   4560
gaagatggag aaagtcctca tagtttccct atttattaga gatctacatc tcgctttctt   4620
gctgtccaat ttctattaaa ggttcctttg ttccctaagt ccaactacta aactggggga   4680
tattatgaag ggccttgagc atctggattc tgcctaataa aaaacattta ttttcattgc   4740
aatgatgtat ttaaattatt tctgaatatt ttactaaaaa gggaatgtgg gaggtcagtg   4800
catttaaaac ataagaaag taggtaacca cgtgcggacc ga                       4842
```

<210> SEQ ID NO 39
<211> LENGTH: 4842
<212> TYPE: DNA
<213> ORGANISM: Artificial sequence
<220> FEATURE:
<223> OTHER INFORMATION: Sequence of expression cassette-CMV-human
      C-terminal-polyA

<400> SEQUENCE: 39

```
acgcgtggag ctagttatta atagtaatca attacggggt cattagttca tagcccatat     60
atggagttcc gcgttacata acttacggta aatggcccgc ctggctgacc gcccaacgac    120
ccccgcccat tgacgtcaat aatgacgtat gttcccatag taacgtcaat agggactttc    180
cattgacgtc aatgggtgga gtatttacgg taaactgccc acttggcagt acatcaagtg    240
tatcatatgc caagtacgcc ccctattgac gtcaatgacg gtaaatggcc cgcctggcat    300
tatgcccagt acatgacctt atgggacttt cctacttggc agtacatcta cgtattagtc    360
atcgctatta ccatggtgat gcggttttgg cagtacatca atgggcgtgg atagcggttt    420
gactcacggg gatttccaag tctccacccc attgacgtca atgggagttt gttttgcacc    480
aaaatcaacg ggactttcca aaatgtcgta caactccgc  cccattgacg caaatgggcg    540
gtaggcgtgt acggtgggag gtctatataa gcagagctcg tttagtgaac cgtcagatcg    600
cctggagacg ccatccacgc tgttttgacc tccatagaag acaccgggac cgatccagcc    660
```

```
tccgcggcca ccatgcaaca atctagggac aaggaagtag agtccctcag aatgcaactg    720
ctagactatc aggcacagtc tgatgaaaag tcgctcattg ccaagttgca ccaacataat    780
gtctctcttc aactgagtga ggctactgct cttggtaagt tggagtcaat tacatctaaa    840
ctgcagaaga tggaggccta caacttgcgc ttagagcaga aacttgatga aaaagaacag    900
gctctctatt atgctcgttt ggagggaaga aacagagcaa acatctgcg ccaaacaatt    960 cagtctctac gacgacagtt tagtggagct ttacccttgg cacaacagga aaagttctcc   1020
aaaacaatga ttcaactaca aaatgacaaa cttaagataa tgcaagaaat gaaaaattct   1080
caacaagaac atagaaatat ggagaacaaa acattggaga tggaattaaa attaaagggc   1140
ctggaagagt taataagcac tttaaaggat accaaggag cccaaaaggt aatcaactgg    1200
catatgaaaa tagaagaact tcgtcttcaa gaacttaaac taaatcggga attagtcaag   1260
gataaagaag aaataaaata tttgaataac ataatttctg aatatgaacg tacaatcagc   1320
agtcttgaag aagaaattgt gcaacagaac aagtttcatg aagaaagaca aatggcctgg   1380
gatcaaagag aagttgacct ggaacgccaa ctagacattt ttgaccgtca gcaaaatgaa   1440
atactaaatg cggcacaaaa gtttgaagaa gctacaggat caatccctga ccctagtttg   1500
cccccttcca atcaacttga gatcgctcta aggaaaatta aggagaacat tcgaataatt   1560
ctagaaacac gggcaacttg caaatcacta gaagagaaac taaagagaa agaatctgct   1620 ttaaggttag cagaacaaaa tatactgtca agagacaaag taatcaatga actgaggctt   1680
cgattgcctg ccactgcaga aagagaaaag ctcatagctg agctaggcag aaaagagatg   1740
gaaccaaaat ctcaccacac attgaaaatt gctcatcaaa ccattgcaaa catgcaagca   1800
aggttaaatc aaaagaaga agtattaaag aagtatcaac gtcttctaga aaaagccaga   1860
gaggagcaaa gagaaattgt gaagaaacat gaggaagacc ttcatattct tcatcacaga   1920
ttagaactac aggctgatag ttcactaaat aaattcaaac aaacggcttg ggatttaatg   1980
aaacagtctc ccactccagt tcctaccaac aagcatttta ttcgtctggc tgagatggaa   2040
cagacagtag cagaacaaga tgactctctt tcctcactct tggtcaaact aaagaaagta   2100
tcacaagatt tggagagaca aagagaaatc actgaattaa agtaaaaga atttgaaaat   2160 atcaaattac agcttcaaga aaaccatgaa gatgaagtga aaaagtaaa agcggaagta   2220 gaggatttaa agtatcttct ggaccagtca caaaaggagt cacagtgttt aaaatctgaa   2280
cttcaggctc aaaagaagc aaattcaaga gctccaacaa ctacaatgag aaatctagta   2340
gaacggctaa agagccaatt agccttgaag gagaaacaac agaaagcact tagtcgggca   2400
cttttagaac tccgggcaga aatgacagca gctgctgaag aacgtattat ttctgcaact   2460
tctcaaaaag aggcccatct caatgttcaa caaatcgttg atcgacatac tagagagcta   2520
aagacacaag ttgaagattt aaatgaaaat cttttaaaat tgaaagaagc acttaaaaca   2580
agtaaaaaca gagaaaactc actaactgat aatttgaatg acttaaataa tgaactgcaa   2640
aagaaacaaa aagcctataa taaatactt agagagaaag aggaaattga tcaagagaat   2700
gatgaactga aaaggcaaat taaaagacta accagtggat tacagggcaa acccctgaca   2760
gataataaac aaagtctaat tgaagaactc caaaggaaag ttaaaaaact agagaaccaa   2820
ttagagggaa aggtggagga agtagaccta aaacctatga agaaaagaa tgctaaagaa   2880 gaattaatta ggtgggaaga aggtaaaaag tggcaagcca aaatagaagg aattcgaaac   2940
aagttaaaag agaagagggg ggaagtcttt actttaacaa agcagttgaa tactttgaag   3000
```

-continued

| | |
|---|---|
| gatcttttg ccaaagccga taaagagaaa cttactttgc agaggaaact aaaaacaact | 3060 |
| ggcatgactg ttgatcaggt tttgggaata cgagctttgg agtcagaaaa agaattggaa | 3120 |
| gaattaaaaa agagaaatct tgacttagaa aatgatatat tgtatatgag ggcccaccaa | 3180 |
| gctcttcctc gagattctgt tgtagaagat ttacatttac aaaatagata cctccaagaa | 3240 |
| aaacttcatg ctttagaaaa acagttttca aaggatacat attctaagcc ttcaatttca | 3300 |
| ggaatagagt cagatgatca ttgtcagaga aacaggagc ttcagaagga aaacttgaag | 3360 |
| ttgtcatctg aaaatattga actgaaattt cagcttgaac aagcaaataa agatttgcca | 3420 |
| agattaaaga atcaagtcag agatttgaag gaaatgtgtg aatttcttaa gaaagaaaaa | 3480 |
| gcagaagttc agcggaaact tggccatgtt agagggtctg gtagaagtgg aaagacaatc | 3540 |
| ccagaactgg aaaaaaccat tggtttaatg aaaaaagtag ttgaaaaagt ccagagagaa | 3600 |
| aatgaacagt tgaaaaaagc atcaggaata ttgactagtg aaaaaatggc taatattgag | 3660 |
| caggaaaatg aaaaattgaa ggctgaatta gaaaaactta agctcatct tgggcatcag | 3720 |
| ttgagcatgc actatgaatc caagaccaaa ggcacagaaa aaattattgc tgaaaatgaa | 3780 |
| aggcttcgta aagaacttaa aaagaaact gatgctgcag agaaattacg gatagcaaag | 3840 |
| aataatttag agatattaaa tgagaagatg acagttcaac tagaagagac tggtaagaga | 3900 |
| ttgcagtttg cagaaagcag aggtccacag cttgaaggtg ctgacagtaa gagctggaaa | 3960 |
| tccattgtgg ttacaagaat gtatgaaacc aagttaaaag aattggaaac tgatattgcc | 4020 |
| aaaaaaaatc aaagcattac tgaccttaaa cagcttgtaa agaagcaac agagagagaa | 4080 |
| caaaaagtta acaaatacaa tgaagacctt gaacaacaga ttaagattct taaacatgtt | 4140 |
| cctgaaggtg ctgagacaga gcaaggcctt aaacgggagc ttcaagttct tagattagct | 4200 |
| aatcatcagc tggataaaga gaaagcagaa ttaatccatc agatagaagc taacaaggac | 4260 |
| caaagtggag ctgaaagcac catacctgat gctgatcaac taaggaaaa aataaaagat | 4320 |
| ctagagacac agctcaaaat gtcagatcta gaaaagcagc attttgaagga ggaaataaag | 4380 |
| aagctgaaaa aagaactgga aaattttgat ccttcatttt ttgaagaaat tgaagatctt | 4440 |
| aagtataatt acaaggaaga agtgaagaag aatattctct tagaagagaa ggtaaaaaaa | 4500 |
| cttttcagaac aattgggagt tgaattaact agccctgttg ctgcttctga agagtttgaa | 4560 |
| gatgaagaag aaagtcctgt taatttcccc atttactaaa gatctacatc tcgctttctt | 4620 |
| gctgtccaat ttctattaaa ggttccttg ttccctaagt ccaactacta aactggggga | 4680 |
| tattatgaag ggccttgagc atctggattc tgcctaataa aaaacattta ttttcattgc | 4740 |
| aatgatgtat ttaaattatt tctgaatatt ttactaaaaa gggaatgtgg gaggtcagtg | 4800 |
| catttaaaac ataagaaag taggtaacca cgtgcggacc ga | 4842 |

<210> SEQ ID NO 40
<211> LENGTH: 4178
<212> TYPE: DNA
<213> ORGANISM: Artificial sequence
<220> FEATURE:
<223> OTHER INFORMATION: Sequence of mouse Myo tail expression vector

<400> SEQUENCE: 40

| | |
|---|---|
| ggcagctgcg cgctcgctcg ctcactgagg ccgcccgggc aaagcccggg cgtcgggcga | 60 |
| cctttggtcg cccggcctca gtgagcgagc gagcgcgcag agagggagtg gccaactcca | 120 |
| tcactagggg ttcctgcggc cgcacgcgtg gagctagtta ttaatagtaa tcaattacgg | 180 |
| ggtcattagt tcatagccca tatatggagt tccgcgttac ataacttacg gtaaatggcc | 240 |

```
cgcctggctg accgcccaac gacccccgcc cattgacgtc aataatgacg tatgttccca    300
tagtaacgtc aatagggact ttccattgac gtcaatgggt ggagtattta cggtaaactg    360
cccacttggc agtacatcaa gtgtatcata tgccaagtac gccccctatt gacgtcaatg    420
acggtaaatg gcccgcctgg cattatgccc agtacatgac cttatgggac tttcctactt    480
ggcagtacat ctacgtatta gtcatcgcta ttaccatggt gatgcggttt tggcagtaca    540
tcaatgggcg tggatagcgg tttgactcac ggggatttcc aagtctccac cccattgacg    600
tcaatgggag tttgttttgc accaaaatca acgggacttt ccaaaatgtc gtaacaactc    660
cgccccattg acgcaaatgg gcggtaggcg tgtacggtgg gaggtctata taagcagagc    720
tcgtttagtg aaccgtcaga tcgcctggag acgccatcca cgctgttttg acctccatag    780
aagacaccgg gaccgatcca gcctccgcgg ccaccatgtt ggcagagcaa atattctgt    840 caagagacaa agtaatcaat gaactgaggc ttcgattgcc tgccacggct gatcgagaaa    900
aacttatagc tgagctagaa agaaaagagc tggagccgaa atctcatcac acaatgaaaa    960
ttgcccacca aactattgcc aacatgcagg caaggttaaa tcacaaggaa gaagtattga   1020
agaaatacca gcaccttctg gagaaggcca gagaggagca aagagaaatt gttaagaagc   1080
atgaggaaga ccttcatgtt cttcatcaca aattagaaca acaggccgat aattcactca   1140
ataaattcag acagacagct caggatttac ttaagcagtc tcctgctcca gttcccacca   1200
acaaacattt cattcgtctg gccgagatgg agcagacagt agcagaacaa gatgactctc   1260
tgtcctcact tttgaccaaa ctaaagaaag tatcaaaaga tttggaaaaa caaaagaaa    1320 tcactgagtt aaaagtcaga gagtttgaaa ataccaaact acggctccaa gaaactcatg   1380
ccagtgaggt aaagaaagtg aaagcagagg tagaggactt aaggcatgct ctagcccaag   1440
cacacaagga ctcccagagt ttaaagtctg aactccaggc tcagaaagaa gcaaactcca   1500
gagctccaac aaccacaatg aggaatcttg tagacaggct aaagagccaa ctagccttga   1560
aagagaagca acaaaaggca cttagtcgag ccctgttgga acttcggtcg aaatgacag    1620 cagcagctga ggaacgtata atcgctgtaa cttctcaaaa agaggcaaat ctcaatgttc   1680
aacaagttgt tgagcgccat actagagagc taaagtcaca aattgaagat ttaaatgaaa   1740
atcttttaaa attgaaagaa gctcttaaaa caagtaagaa caaagaaaat tcactagctg   1800
atgatttaaa tgaattaaat aatgaactgc aaaaaaagca aaaagcttat aataaaatcc   1860
ttagagagaa agatggaatt gatcaagaaa atgatgaact gagaagacag attaaaagac   1920
tgtccagtgg actgcagagc aaaactttga tagataacaa gcaaagttta atcgatgaac   1980
ttcaaaagaa agttaaaaaa cttgaaagcc aactggaaag aaaggtggat gacgtagaca   2040
taaagccggt gaaggaaaag agtagtaaag aagaattaat taggtgggaa gaaggtaaga   2100
aatggcaaac caaagtagag ggactacgaa acagactaaa ggagaaggaa ggagaagccc   2160
acggcctggc aaagcagctg aatacccttaa aggaactttt tgccaaagct gataaagaga   2220
aacttacttt gcagaagaaa ctgaaaacaa caggaatgac tgttgaccag gttttaggag   2280
tgcgagcttt ggaatctgaa aaagagttgg aagagctaaa aaagaaaaat ctggacctag   2340
aaaatgacat attatacatg aggacccagc aggctcttcc acgagattct gttgtggaag   2400
acttacattt acaaaataaa taccttcaag aaaaacttca tactttagaa aaaaaacttt   2460
caaaggagaa atattctcag tctttgactt cagaaataga gtcagatgat cactgtcaaa   2520
aagaacaaga acttcagaag gaaaatttga agttgtcatc tgaaaacatc gagctgaaat   2580
```

-continued

```
ttcaacttga caagcaaat aaagatttgc caagactaaa gaatcaagtg aaagatttga    2640
aggaaatgtg tgaatttctt aagaaaggaa aactggaact tgagcggaag cttggtcagg    2700
tcagaggggc tggtagaagt gggaagacaa tcccagaact agaaaaaacc attgggttaa    2760
tgaagaaagt agttgaaaaa gtccaaagag aaaatgaaca attgaaaaag gcatcaggaa    2820
tactgactag tgaaaaaatg gctactattg aggaagaaaa tagaaactta aaggctgaac    2880
tagaaaagct taaagctcac tttggacgtc agttgagtat gcagtttgaa tctaagaaca    2940
aggtactga gaaaattgtt gccgaaaatg aacggcttcg gaaagaactt aagaaagaaa    3000
tagaagcctc tgagaaactg cggatagcta agaacaactt agagctggtg aacgacaaga    3060
tggcagctca actcgaagaa actgggaaga gactacagtt tgcagaaagt agagccccac    3120
agctggaagg tgctgacagc aagagctgga agtcaattgt ggtctcaaga gtgtatgaga    3180
ccaagatgaa agagcttgaa agtgacattg ccaaaaagaa tcaaagtatc actgacctta    3240
aacagcttgt aagagaagca acagagagag aacagaaagc taagaaatac actgaagacc    3300
ttgaacaaca gattgagatc ctcaaaaatg ttcctgaagg tgccgagaca gagcaagagc    3360
ttatacggga actccagctt cttagattag ccaataatca gatggataaa gaaagggcag    3420
aattaatcca tcagatagaa attaacaagg accaaaccag agctgacagt agcatacctg    3480
attctgatca actaaaggaa aagataaatg acctggagac acaactcaga aagttggagc    3540
tagaaaagca acattcgaag gaggaagtta aaaagctgaa aaaagaactg gaaaattttg    3600
atccttcatt ttttgaagaa attgaagacc tgaagtataa ttataaggaa gaagtgaaaa    3660
agaatatcct attagaagag aagctaaaaa aactgtcgga acagtttgga tttgaactgc    3720
ctagtcctct tgctgcttct gaacactcgg aagatggaga aagtcctcat agtttcccta    3780
tttattagag atctacatct cgctttcttg ctgtccaatt tctattaaag gttcctttgt    3840
tccctaagtc caactactaa actgggggat attatgaagg gccttgagca tctggattct    3900
gcctaataaa aaacatttat tttcattgca atgatgtatt taaattattt ctgaatattt    3960
tactaaaaag ggaatgtggg aggtcagtgc atttaaaaca taaagaaagt aggtaaccac    4020
gtgcggaccg agcggccgca ggaaccccta gtgatggagt tggccactcc ctctctgcgc    4080
gctcgctcgc tcactgaggc cgggcgacca aaggtcgccc gacgcccggg ctttgcccgg    4140
gcggcctcag tgagcgagcg agcgcgcagc tgcctgca                           4178
```

<210> SEQ ID NO 41
<211> LENGTH: 4181
<212> TYPE: DNA
<213> ORGANISM: Artificial sequence
<220> FEATURE:
<223> OTHER INFORMATION: Sequence of human Myo tail expression vector

<400> SEQUENCE: 41

```
ggcagctgcg cgctcgctcg ctcactgagg ccgcccgggc aaagcccggg cgtcgggcga      60
cctttggtcg cccggcctca gtgagcgagc gagcgcgcag agagggagtg gccaactcca     120
tcactagggg ttcctgcggc cgcacgcgtg gagctagtta ttaatagtaa tcaattacgg     180
ggtcattagt tcatagccca tatatggagt tccgcgttac ataacttacg gtaaatggcc     240
cgcctggctg accgcccaac gacccccgcc cattgacgtc aataatgacg tatgttccca     300
tagtaacgtc aatagggact ttccattgac gtcaatgggt ggagtattta cggtaaactg     360
cccacttggc agtacatcaa gtgtatcata tgccaagtac gccccctatt gacgtcaatg     420
acggtaaatg gcccgcctgg cattatgccc agtacatgac cttatgggac tttcctactt     480
```

```
ggcagtacat ctacgtatta gtcatcgcta ttaccatggt gatgcggttt tggcagtaca    540
tcaatgggcg tggatagcgg tttgactcac ggggatttcc aagtctccac cccattgacg    600
tcaatgggag tttgttttgc accaaaatca acgggacttt ccaaaatgtc gtaacaactc    660
cgccccattg acgcaaatgg gcggtaggcg tgtacggtgg gaggtctata taagcagagc    720
tcgtttagtg aaccgtcaga tcgcctggag acgccatcca cgctgttttg acctccatag    780
aagacaccgg gaccgatcca gcctccgcgg ccaccatgtt agcagaacaa aatatactgt    840
caagagacaa agtaatcaat gaactgaggc ttcgattgcc tgccactgca gaaagagaaa    900
agctcatagc tgagctaggc agaaaagaga tggaaccaaa atctcaccac acattgaaaa    960
ttgctcatca aaccattgca acatgcaag caaggttaaa tcaaaaagaa gaagtattaa    1020
agaagtatca acgtcttcta gaaaaagcca gagaggagca aagagaaatt gtgaagaaac    1080
atgaggaaga ccttcatatt cttcatcaca gattagaact acaggctgat agttcactaa    1140
ataaattcaa acaaacggct tgggatttaa tgaaacagtc tcccactcca gttcctacca    1200
acaagcattt tattcgtctg gctgagatgg aacagacagt agcagaacaa gatgactctc    1260
tttcctcact cttggtcaaa ctaaagaaag tatcacaaga tttggagaga caaagagaaa    1320
tcactgaatt aaaagtaaaa gaatttgaaa atatcaaatt acagcttcaa gaaaaccatg    1380
aagatgaagt gaaaaagta aaagcggaag tagaggattt aaagtatctt ctggaccagt    1440
cacaaaagga gtcacagtgt ttaaaatctg aacttcaggc tcaaaaagaa gcaaattcaa    1500
gagctccaac aactacaatg agaaatctag tagaacggct aaagagccaa ttagccttga    1560
aggagaaaca acagaaagca cttagtcggg cactttttaga actccgggca gaaatgacag    1620
cagctgctga agaacgtatt atttctgcaa cttctcaaaa agaggcccat ctcaatgttc    1680
aacaaatcgt tgatcgacat actagagagc taaagacaca agttgaagat ttaaatgaaa    1740
atcttttaaa attgaaagaa gcacttaaaa caagtaaaaa cagagaaaac tcactaactg    1800
ataatttgaa tgacttaaat aatgaactgc aaaagaaaca aaaagcctat aataaaaatac    1860 ttagagagaa agaggaaatt gatcaagaga atgatgaact gaaaaggcaa attaaaagac    1920
taaccagtgg attacagggc aaacccctga cagataataa acaaagtcta attgaagaac    1980
tccaaaggaa agttaaaaaa ctagagaacc aattagaggg aaaggtggag gaagtagacc    2040
taaaacctat gaaagaaaag aatgctaaag aagaattaat taggtgggaa gaaggtaaaa    2100
agtggcaagc caaaatagaa ggaattcgaa acaagttaaa agagaaagag ggggaagtct    2160
ttactttaac aaagcagttg aatactttga aggatctttt tgccaaagcc gataaagaga    2220
aacttacttt gcagaggaaa ctaaaaacaa ctggcatgac tgttgatcag gttttgggaa    2280
tacgagcttt ggagtcagaa aaagaattgg aagaattaaa aaagagaaat cttgacttag    2340
aaaatgatat attgtatatg agggcccacc aagctcttcc tcgagattct gttgtagaag    2400
atttacattt acaaaataga tacctccaag aaaaacttca tgctttagaa aaacagttttt    2460 caaaggatac atattctaag ccttcaattt caggaataga gtcagatgat cattgtcaga    2520
gagaacagga gcttcagaag gaaaacttga agttgtcatc tgaaaatatt gaactgaaat    2580
ttcagcttga acaagcaaat aaagatttgc caagattaaa gaatcaagtc agagatttga    2640
aggaaatgtg tgaatttctt aagaaagaaa aagcagaagt tcagcggaaa cttggccatg    2700
ttagagggtc tggtagaagt ggaaagacaa tcccagaact ggaaaaaacc attggtttaa    2760
tgaaaaaagt agttgaaaaa gtccagagag aaaatgaaca gttgaaaaaa gcatcaggaa    2820
```

| | |
|---|---|
| tattgactag tgaaaaaatg ctaatattg agcaggaaaa tgaaaaattg aaggctgaat | 2880 |
| tagaaaaact taaagctcat cttgggcatc agttgagcat gcactatgaa tccaagacca | 2940 |
| aaggcacaga aaaattatt gctgaaaatg aaaggcttcg taaagaactt aaaaaagaaa | 3000 |
| ctgatgctgc agagaaatta cggatagcaa agaataattt agagatatta aatgagaaga | 3060 |
| tgacagttca actagaagag actggtaaga gattgcagtt tgcagaaagc agaggtccac | 3120 |
| agcttgaagg tgctgacagt aagagctgga atccattgt ggttacaaga atgtatgaaa | 3180 |
| ccaagttaaa agaattggaa actgatattg ccaaaaaaaa tcaaagcatt actgacctta | 3240 |
| aacagcttgt aaaagaagca acagagagag aacaaaaagt taacaaatac aatgaagacc | 3300 |
| ttgaacaaca gattaagatt cttaaacatg ttcctgaagg tgctgagaca gagcaaggcc | 3360 |
| ttaaacggga gcttcaagtt cttagattag ctaatcatca gctggataaa gagaaagcag | 3420 |
| aattaatcca tcagatagaa gctaacaagg accaaagtgg agctgaaagc accatacctg | 3480 |
| atgctgatca actaaggaa aaaataaaag atctagagac acagctcaaa atgtcagatc | 3540 |
| tagaaaagca gcatttgaag gaggaaataa agaagctgaa aaaagaactg gaaaattttg | 3600 |
| atccttcatt ttttgaagaa attgaagatc ttaagtataa ttacaaggaa gaagtgaaga | 3660 |
| agaatattct cttagaagag aaggtaaaaa aactttcaga acaattggga gttgaattaa | 3720 |
| ctagccctgt tgctgcttct gaagagtttg aagatgaaga agaaagtcct gttaatttcc | 3780 |
| ccatttacta aagatctaca tctcgctttc ttgctgtcca atttctatta aaggttcctt | 3840 |
| tgttccctaa gtccaactac taaactgggg gatattatga agggccttga gcatctggat | 3900 |
| tctgcctaat aaaaaacatt tattttcatt gcaatgatgt atttaaatta tttctgaata | 3960 |
| ttttactaaa aagggaatgt gggaggtcag tgcatttaaa acataaagaa agtaggtaac | 4020 |
| cacgtgcgga ccgagcggcc gcaggaaccc ctagtgatgg agttggccac tccctctctg | 4080 |
| cgcgctcgct cgctcactga ggccgggcga ccaaaggtcg cccgacgccc gggctttgcc | 4140 |
| cgggcggcct cagtgagcga gcgagcgcgc agctgcctgc a | 4181 |

<210> SEQ ID NO 42
<211> LENGTH: 2108
<212> TYPE: DNA
<213> ORGANISM: Artificial sequence
<220> FEATURE:
<223> OTHER INFORMATION: Sequence of mouse DSD expression vector

<400> SEQUENCE: 42

| | |
|---|---|
| ggcagctgcg cgctcgctcg ctcactgagg ccgcccgggc aaagcccggg cgtcgggcga | 60 |
| cctttggtcg cccggcctca gtgagcgagc gagcgcgcag agagggagtg gccaactcca | 120 |
| tcactagggg ttcctgcggc cgcacgcgtg gagctagtta ttaatagtaa tcaattacgg | 180 |
| ggtcattagt tcatagccca tatatggagt tccgcgttac ataacttacg gtaaatggcc | 240 |
| cgcctggctg accgcccaac gacccccgcc cattgacgtc aataatgacg tatgttccca | 300 |
| tagtaacgtc aatagggact ttccattgac gtcaatgggt ggagtattta cggtaaactg | 360 |
| cccacttggc agtacatcaa gtgtatcata tgccaagtac gccccctatt gacgtcaatg | 420 |
| acggtaaatg gcccgcctgg cattatgccc agtacatgac cttatgggac ttcctactt | 480 |
| ggcagtacat ctacgtatta gtcatcgcta ttaccatggt gatgcggttt tggcagtaca | 540 |
| tcaatgggcg tggatagcgg tttgactcac ggggatttcc aagtctccac cccattgacg | 600 |
| tcaatgggag tttgttttgc accaaaatca acgggacttt ccaaaatgtc gtaacaactc | 660 |
| cgccccattg acgcaaatgg gcggtaggcg tgtacggtgg gaggtctata taagcagagc | 720 |

| | |
|---|---:|
| tcgtttagtg aaccgtcaga tcgcctggag acgccatcca cgctgttttg acctccatag | 780 |
| aagacaccgg gaccgatcca gcctccgcgg ccaccatgga tttacttaag cagtctcctg | 840 |
| ctccagttcc caccaacaaa catttcattc gtctggccga gatggagcag acagtagcag | 900 |
| aacaagatga ctctctgtcc tcacttttga ccaaactaaa gaaagtatca aaagatttgg | 960 |
| aaaaacaaaa agaaatcact gagttaaaag tcagagagtt tgaaaatacc aaactacggc | 1020 |
| tccaagaaac tcatgccagt gaggtaaaga agtgaaagc agaggtagag acttaaggc | 1080 |
| atgctctagc ccaagcacac aaggactccc agagtttaaa gtctgaactc caggctcaga | 1140 |
| aagaagcaaa ctccagagct ccaacaacca caatgaggaa tcttgtagac aggctaaaga | 1200 |
| gccaactagc cttgaaagag aagcaacaaa aggcacttag tcgagccctg ttggaacttc | 1260 |
| ggtcggaaat gacagcagca gctgaggaac gtataatcgc tgtaacttct caaaaagagg | 1320 |
| caaatctcaa tgttcaacaa gttgttgagc gccatactag agagctaaag tcacaaattg | 1380 |
| aagatttaaa tgaaaatctt ttaaaattga agaagctct taaaacaagt aagaacaaag | 1440 |
| aaaattcact agctgatgat ttaaatgaat taaataatga actgcaaaaa agcaaaaag | 1500 |
| cttataataa aatccttaga gagaaagatg gaattgatca agaaaatgat gaactgagaa | 1560 |
| gacagattaa aagactgtcc agtggactgc agagcaaaac tttgatagat aacaagcaaa | 1620 |
| gtttaatcga tgaacttcaa aagaaagtta aaaaacttga agccaactg gaaagaaagg | 1680 |
| tggatgacgt agacataaag ccggtgaagg aaaagtagag atctacatct cgctttcttg | 1740 |
| ctgtccaatt tctattaaag gttcctttgt tccctaagtc caactactaa actgggggat | 1800 |
| attatgaagg gccttgagca tctggattct gcctaataaa aaacatttat tttcattgca | 1860 |
| atgatgtatt taaattattt ctgaatattt tactaaaaag ggaatgtggg aggtcagtgc | 1920 |
| atttaaaaca taaagaaagt aggtaaccac gtgcggaccg agcggccgca ggaaccccta | 1980 |
| gtgatggagt tggccactcc ctctctcgc gctcgctcgc tcactgaggc cgggcgacca | 2040 |
| aaggtcgccc gacgcccggg ctttgcccgg gcggcctcag tgagcgagcg agcgcgcagc | 2100 |
| tgcctgca | 2108 |

<210> SEQ ID NO 43
<211> LENGTH: 2108
<212> TYPE: DNA
<213> ORGANISM: Artificial sequence
<220> FEATURE:
<223> OTHER INFORMATION: Sequence of human DSD expression vector

<400> SEQUENCE: 43

| | |
|---|---:|
| ggcagctgcg cgctcgctcg ctcactgagg ccgcccgggc aaagcccggg cgtcgggcga | 60 |
| cctttggtcg cccggcctca gtgagcgagc gagcgcgcag agagggagtg gccaactcca | 120 |
| tcactagggg ttcctgcggc cgcacgcgtg gagctagtta ttaatagtaa tcaattacgg | 180 |
| ggtcattagt tcatagccca tatatggagt tccgcgttac ataacttacg gtaaatggcc | 240 |
| cgcctggctg accgcccaac gacccccgcc cattgacgtc aataatgacg tatgttccca | 300 |
| tagtaacgtc aatagggact ttccattgac gtcaatgggt ggagtattta cggtaaactg | 360 |
| cccacttggc agtacatcaa gtgtatcata tgccaagtac gccccctatt gacgtcaatg | 420 |
| acggtaaatg gcccgcctgg cattatgccc agtacatgac cttatgggac tttcctactt | 480 |
| ggcagtacat ctacgtatta gtcatcgcta ttaccatggt gatgcggttt tggcagtaca | 540 |
| tcaatgggcg tggatagcgg tttgactcac ggggatttcc aagtctccac cccattgacg | 600 |

| | |
|---|---|
| tcaatgggag tttgttttgc accaaaatca acgggacttt ccaaaatgtc gtaacaactc | 660 |
| cgccccattg acgcaaatgg gcggtaggcg tgtacggtgg gaggtctata taagcagagc | 720 |
| tcgtttagtg aaccgtcaga tcgcctggag acgccatcca cgctgttttg acctccatag | 780 |
| aagacaccgg gaccgatcca gcctccgcgg ccaccatgga tttaatgaaa cagtctccca | 840 |
| ctccagttcc taccaacaag catttttattc gtctggctga gatggaacag acagtagcag | 900 |
| aacaagatga ctctctttcc tcactcttgg tcaaactaaa gaaagtatca caagatttgg | 960 |
| agagacaaag agaaatcact gaattaaaag taaagaatt tgaaaatatc aaattacagc | 1020 |
| ttcaagaaaa ccatgaagat gaagtgaaaa agtaaaagc ggaagtagag gatttaaagt | 1080 |
| atcttctgga ccagtcacaa aaggagtcac agtgtttaaa atctgaactt caggctcaaa | 1140 |
| aagaagcaaa ttcaagagct ccaacaacta caatgagaaa tctagtagaa cggctaaaga | 1200 |
| gccaattagc cttgaaggag aaacaacaga aagcacttag tcgggcactt ttagaactcc | 1260 |
| gggcagaaat gacagcagct gctgaagaac gtattatttc tgcaacttct caaaaagagg | 1320 |
| cccatctcaa tgttcaacaa atcgttgatc gacatactag agagctaaag acacaagttg | 1380 |
| aagatttaaa tgaaaatctt ttaaaattga agaagcact taaaacaagt aaaaacagag | 1440 |
| aaaactcact aactgataat ttgaatgact aaataatga actgcaaaag aaacaaaaag | 1500 |
| cctataataa aatacttaga gagaagagg aaattgatca agagaatgat gaactgaaaa | 1560 |
| ggcaaattaa aagactaacc agtggattac agggcaaacc cctgacagat aataaacaaa | 1620 |
| gtctaattga agaactccaa aggaaagtta aaaaactaga gaaccaatta gagggaaagg | 1680 |
| tggaggaagt agacctaaaa cctatgaaag aaaagtagag atctacatct cgctttcttg | 1740 |
| ctgtccaatt tctattaaag gttcctttgt tccctaagtc caactactaa actgggggat | 1800 |
| attatgaagg gccttgagca tctggattct gcctaataaa aaacatttat tttcattgca | 1860 |
| atgatgtatt taaattattt ctgaatattt tactaaaaag ggaatgtggg aggtcagtgc | 1920 |
| atttaaaaca taaagaaagt aggtaaccac gtgcggaccg agcggccgca ggaacccta | 1980 |
| gtgatggagt tggccactcc ctctctgcgc gctcgctcgc tcactgaggc cgggcgacca | 2040 |
| aaggtcgccc gacgcccggg ctttgcccgg gcggcctcag tgagcgagcg agcgcgcagc | 2100 |
| tgcctgca | 2108 |

<210> SEQ ID NO 44
<211> LENGTH: 5132
<212> TYPE: DNA
<213> ORGANISM: Artificial sequence
<220> FEATURE:
<223> OTHER INFORMATION: Sequence of mouse C-terminal expression vector

<400> SEQUENCE: 44

| | |
|---|---|
| ggcagctgcg cgctcgctcg ctcactgagg ccgcccgggc aaagcccggg cgtcgggcga | 60 |
| cctttggtcg cccggcctca gtgagcgagc gagcgcgcag agagggagtg gccaactcca | 120 |
| tcactagggg ttcctgcggc cgcacgcgtg gagctagtta ttaatagtaa tcaattacgg | 180 |
| ggtcattagt tcatagccca tatatggagt tccgcgttac ataacttacg gtaaatggcc | 240 |
| cgcctggctg accgcccaac gacccccgcc cattgacgtc aataatgacg tatgttccca | 300 |
| tagtaacgtc aatagggact ttccattgac gtcaatgggt ggagtattta cggtaaactg | 360 |
| cccacttggc agtacatcaa gtgtatcata tgccaagtac gccccctatt gacgtcaatg | 420 |
| acggtaaatg gcccgcctgg cattatgccc agtacatgac cttatgggac tttcctactt | 480 |
| ggcagtacat ctacgtatta gtcatcgcta ttaccatggt gatgcggttt tggcagtaca | 540 |

```
tcaatgggcg tggatagcgg tttgactcac ggggatttcc aagtctccac cccattgacg    600
tcaatgggag tttgttttgc accaaaatca acgggacttt ccaaaatgtc gtaacaactc    660
cgccccattg acgcaaatgg gcggtaggcg tgtacggtgg gaggtctata taagcagagc    720
tcgtttagtg aaccgtcaga tcgcctggag acgccatcca cgctgttttg acctccatag    780
aagacaccgg gaccgatcca gcctccgcgg ccaccatgca acaacagtcc agggaaaagg    840
aagtggaatc cctcagaacg cagctgctgg acttccaggc acaatctgac gaaaaggctc    900
taattgccaa attgcaccaa catgttgtct ctcttcaaat tagtgaggcc actgccctcg    960
gtaagttaga gtcagttacg tccaaactcc agaagatgga agcctacaat ttgcgcttag   1020
aacagaaact ggatgaaaaa gagcaggcgc tctactatgc tcgtttggaa ggtagaaaca   1080
gagcaaaaca cctgcgccaa accattcagt cgcttcgaag acagttcagt ggagctctac   1140
ccttagcaca gcaggaaaag ttctccaaaa cgatgattca gttgcaaaat gacaaactta   1200
agataatgca agaaatgaag aattcgcaac aggaacacag aaatatggaa acaaaaacac   1260
tggagttgga attaaaatta aaaggcttag aagaattgat cagtacttta aaggatgcca   1320
ggggagccca gaaggtaatc aattggcatg tgaaaataga agaacttcgc ctccaagaac   1380
ttaagctaaa tagagaacta gtcaagggta agaagaaat caaatatttg aataatatca   1440
tctctgaata tgagcataca atcaacagtc tagaggaaga aattgttcag caaagcaagt   1500
tccatgaaga aagacagatg gcttgggatc aaagagaagt tgagctggaa cgccagttag   1560
acatttttga tcatcagcaa aatgaaatac tcagtgcagc acaaaagttt gaagactcta   1620
caggatcaat gccagacccc agcttgcctc ttccaaacca acttgaaatt gctctaagaa   1680
aaattaagga gaatattcaa gtaattctta aaacacaagc aacttgcaag tcactagaag   1740
agaaactaaa agaaaagaa tctgctttac ggttggcaga gcaaaatatt ctgtcaagag   1800
acaaagtaat caatgaactg aggcttcgat tgcctgccac ggctgatcga gaaaaactta   1860
tagctgagct agaaagaaaa gagctggagc cgaaatctca tcacacaatg aaaattgccc   1920
accaaactat tgccaacatg caggcaaggt taaatcacaa ggaagaagta ttgaagaaat   1980
accagcacct tctggagaag gccagagagg agcaaagaga aattgttaag aagcatgagg   2040
aagaccttca tgttcttcat cacaaattag aacaacaggc cgataattca ctcaataaat   2100
tcagacagac agctcaggat ttacttaagc agtctcctgc tccagttccc accaacaaac   2160
atttcattcg tctggccgag atggagcaga cagtagcaga acaagatgac tctctgtcct   2220
cacttttgac caaactaaag aaagtatcaa aagatttgga aaaacaaaaa gaatcactg   2280 agttaaaagt cagagagttt gaaaatacca aactacggct ccaagaaact catgccagtg   2340
aggtaaagaa agtgaaagca gaggtagagg acttaaggca tgctctagcc caagcacaca   2400
aggactccca gagtttaaag tctgaactcc aggctcagaa agaagcaaac tccagagctc   2460
caacaaccac aatgaggaat cttgtagaca ggctaaagag ccaactagcc ttgaaagaga   2520
agcaacaaaa ggcacttagt cgagccctgt tggaacttcg gtcggaaatg acagcagcag   2580
ctgaggaacg tataatcgct gtaacttctc aaaaagaggc aaatctcaat gttcaacaag   2640
ttgttgagcg ccatactaga gagctaaagt cacaaattga agatttaaat gaaaatcttt   2700
taaaattgaa agaagctctt aaaacaagta agaacaaaga aaattcacta gctgatgatt   2760
taaatgaatt aaataatgaa ctgcaaaaaa agcaaaaagc ttataataaa atccttagag   2820
agaaagatgg aattgatcaa gaaaatgatg aactgagaag acagattaaa agactgtcca   2880
```

```
gtggactgca gagcaaaact tgatagata caagcaaag tttaatcgat gaacttcaaa    2940
agaaagttaa aaaacttgaa agccaactgg aagaaaggt ggatgacgta gacataaagc   3000
cggtgaagga aaagagtagt aaagaagaat taattaggtg ggaagaaggt aagaaatggc  3060
aaaccaaagt agagggacta cgaaacagac taaaggagaa ggaaggagaa gcccacggcc  3120
tggcaaagca gctgaatacc ttaaaggaac tttttgccaa agctgataaa gagaaactta  3180
ctttgcagaa gaaactgaaa acaacaggaa tgactgttga ccaggtttta ggagtgcgag  3240
ctttggaatc tgaaaaagag ttggaagagc taaaaaagaa aaatctggac ctagaaaatg  3300
acatattata catgaggacc cagcaggctc ttccacgaga ttctgttgtg aagacttac   3360
atttacaaaa taaataccct caagaaaaac ttcatacttt agaaaaaaaa ctttcaaagg  3420
agaaatattc tcagtctttg acttcagaaa tagagtcaga tgatcactgt caaaaagaac  3480
aagaacttca gaaggaaaat ttgaagttgt catctgaaaa catcgagctg aaatttcaac  3540
ttgaacaagc aaataaagat ttgccaagac taaagaatca agtgaaagat ttgaaggaaa  3600
tgtgtgaatt tcttaagaaa ggaaaactgg aacttgagcg gaagcttggt caggtcagag  3660
gggctggtag aagtgggaag acaatcccag aactagaaaa aaccattggg ttaatgaaga  3720
aagtagttga aaaagtccaa agagaaaatg aacaattgaa aaaggcatca ggaatactga  3780
ctagtgaaaa aatggctact attgaggaag aaaatagaaa cttaaaggct gaactagaaa  3840
agcttaaagc tcactttgga cgtcagttga gtatgcagtt tgaatctaag aacaaaggta  3900
ctgagaaaat tgttgccgaa aatgaacggc ttcggaaaga acttaagaaa gaaatagaag  3960
cctctgagaa actgcggata gctaagaaca acttagagct ggtgaacgac aagatggcag  4020
ctcaactcga gaaactgggg aagagactac agtttgcaga agtagagcc ccacagctgg   4080
aaggtgctga cagcaagagc tggaagtcaa ttgtggtctc aagagtgtat gagaccaaga  4140
tgaaagagct tgaaagtgac attgccaaaa agaatcaaag tatcactgac cttaaacagc  4200
ttgtaagaga agcaacagag agagaacaga agctaagaa atacactgaa gaccttgaac  4260
aacagattga gatcctcaaa aatgttcctg aaggtgccga gacagagcaa gagcttatac  4320
gggaactcca gcttcttaga ttagccaata atcagatgga taaagaaagg gcagaattaa  4380
tccatcagat agaaattaac aaggaccaaa ccagagctga cagtagcata cctgattctg  4440
atcaactaaa ggaaaagata aatgacctgg agacacaact cagaaagttg gagctagaaa  4500
agcaacattc gaaggaggaa gttaaaaagc tgaaaaaaga actggaaaat tttgatcctt  4560
cattttttga agaaattgaa gacctgaagt ataattataa ggaagaagtg aaaaagaata  4620
tcctattaga agagaagcta aaaaaactgt cggaacagtt tggatttgaa ctgcctagtc  4680
ctcttgctgc ttctgaacac tcggaagatg gagaaagtcc tcatagtttc cctatttatt  4740
agagatctac atctcgcttt cttgctgtcc aatttctatt aaaggttcct tgttcccta   4800
agtccaacta ctaaactggg ggatattatg aagggccttg agcatctgga ttctgcctaa  4860
taaaaaacat ttattttcat tgcaatgatg tatttaaatt atttctgaat attttactaa  4920
aaagggaatg tgggaggtca gtgcatttaa aacataaaga aagtaggtaa ccacgtgcgg  4980
accgagcggc cgcaggaacc cctagtgatg agttggcca ctccctctct gcgcgctcgc    5040
tcgctcactg aggccgggcg accaaggtc gcccgacgcc cgggctttgc ccgggcggcc   5100
tcagtgagcg agcgagcgcg cagctgcctg ca                                5132

<210> SEQ ID NO 45
<211> LENGTH: 5132
```

<212> TYPE: DNA
<213> ORGANISM: Artificial sequence
<220> FEATURE:
<223> OTHER INFORMATION: Sequence of human C-terminal expression vector

<400> SEQUENCE: 45

```
ggcagctgcg cgctcgctcg ctcactgagg ccgcccgggc aaagcccggg cgtcgggcga    60
cctttggtcg cccggcctca gtgagcgagc gagcgcgcag agagggagtg gccaactcca   120
tcactagggg ttcctgcggc cgcacgcgtg gagctagtta ttaatagtaa tcaattacgg   180
ggtcattagt tcatagccca tatatggagt tccgcgttac ataacttacg gtaaatggcc   240
cgcctggctg accgcccaac gacccccgcc cattgacgtc aataatgacg tatgttccca   300
tagtaacgtc aatagggact ttccattgac gtcaatgggt ggagtattta cggtaaactg   360
cccacttggc agtacatcaa gtgtatcata tgccaagtac gccccctatt gacgtcaatg   420
acggtaaatg gcccgcctgg cattatgccc agtacatgac cttatgggac tttcctactt   480
ggcagtacat ctacgtatta gtcatcgcta ttaccatggt gatgcggttt tggcagtaca   540
tcaatgggcg tggatagcgg tttgactcac ggggatttcc aagtctccac cccattgacg   600
tcaatgggag tttgttttgc accaaaatca acgggacttt ccaaaatgtc gtaacaactc   660
cgccccattg acgcaaatgg gcggtaggcg tgtacggtgg gaggtctata taagcagagc   720
tcgtttagtg aaccgtcaga tcgcctggag acgccatcca cgctgttttg acctccatag   780
aagacaccgg gaccgatcca gcctccgcgg ccaccatgca acaatctagg gacaaggaag   840
tagagtccct cagaatgcaa ctgctagact atcaggcaca gtctgatgaa aagtcgctca   900
ttgccaagtt gcaccaacat aatgtctctc ttcaactgag tgaggctact gctcttggta   960
agttggagtc aattacatct aaactgcaga gatggaggc ctacaacttg cgcttagagc   1020
agaaacttga tgaaaagaa caggctctct attatgctcg tttggaggga agaaacagag   1080
caaaacatct gcgccaaaca attcagtctc tacgacgaca gtttagtgga gctttacct   1140
tggcacaaca ggaaaagttc tccaaaacaa tgattcaact acaaaatgac aaacttaaga   1200
taatgcaaga aatgaaaaat tctcaacaag aacatagaaa tatggagaac aaaacattgg   1260
agatggaatt aaaattaaag ggcctggaag agttaataag cactttaaag gataccaaag   1320
gagcccaaaa ggtaatcaac tggcatatga aatagaaga acttcgtctt caagaactta   1380
aactaaatcg ggaattagtc aaggataaag aagaaataaa atatttgaat aacataattt   1440
ctgaatatga acgtacaatc agcagtcttg aagaagaaat tgtgcaacag aacaagtttc   1500
atgaagaaag acaaatggcc tgggatcaaa gagaagttga cctggaacgc caactagaca   1560
tttttgaccg tcagcaaaat gaaatactaa atgcggcaca aagtttgaa gaagctacag   1620
gatcaatccc tgaccctagt ttgcccctc caaatcaact tgagatcgct ctaaggaaaa   1680
ttaaggagaa cattcgaata attctagaaa cacgggcaac ttgcaaatca ctagaagaga   1740
aactaaaaga gaagaatct gctttaaggt tagcagaaca aaatatactg tcaagagaca   1800
aagtaatcaa tgaactgagg cttcgattgc ctgccactgc agaaagagaa aagctcatag   1860
ctgagctagg cagaaaagag atggaaccaa atctcacca cacattgaaa attgctcatc   1920
aaaccattgc aaacatgcaa gcaaggttaa atcaaaaaga agaagtatta agaagtatc   1980
aacgtcttct agaaaaagcc agagaggagc aaagagaaat tgtgaagaaa catgaggaag   2040
accttcatat tcttcatcac agattagaac tacaggctga tagttcacta aataaattca   2100
aacaaacggc ttgggattta atgaaacagt ctcccactcc agttcctacc aacaagcatt   2160
```

```
ttattcgtct ggctgagatg gaacagacag tagcagaaca agatgactct ctttcctcac    2220
tcttggtcaa actaaagaaa gtatcacaag atttggagag acaaagagaa atcactgaat    2280
taaaagtaaa agaatttgaa aatatcaaat tacagcttca agaaaaccat gaagatgaag    2340
tgaaaaagt  aaaagcggaa gtagaggatt taaagtatct tctggaccag tcacaaaagg    2400
agtcacagtg tttaaaatct gaacttcagg ctcaaaaaga agcaaattca agagctccaa    2460
caactacaat gagaaatcta gtagaacggc taaagagcca attagccttg aaggagaaac    2520
aacagaaagc acttagtcgg gcacttttag aactccgggc agaaatgaca gcagctgctg    2580
aagaacgtat tatttctgca acttctcaaa aagaggccca tctcaatgtt caacaaatcg    2640
ttgatcgaca tactagagag ctaaagacac aagttgaaga tttaaatgaa aatcttttaa    2700
aattgaaaga agcacttaaa acaagtaaaa acagagaaaa ctcactaact gataatttga    2760
atgacttaaa taatgaactg caaaagaaac aaaaagccta ataaaaata  cttagagaga    2820
aagaggaaat tgatcaagag aatgatgaac tgaaaaggca aattaaaaga ctaaccagtg    2880
gattacaggg caaacccctg acagataata aacaaagtct aattgaagaa ctccaaagga    2940
aagttaaaaa actagagaac caattagagg gaaaggtgga ggaagtagac ctaaaaccta    3000
tgaaagaaaa gaatgctaaa aagaattaa  ttaggtggga agaaggtaaa aagtggcaag    3060
ccaaaataga aggaattcga aacaagttaa agagagaaga ggggaagtc  tttactttaa    3120
caaagcagtt gaatactttg aaggatcttt ttgccaaagc cgataaagag aaacttactt    3180
tgcagaggaa actaaaaaca actggcatga ctgttgatca ggttttggga atacgagctt    3240
tggagtcaga aaaagaattg gaagaattaa aaaagagaaa tcttgactta gaaaatgata    3300
tattgtatat gagggcccac caagctcttc ctcgagattc tgttgtagaa gatttacatt    3360
tacaaaatag atacctccaa gaaaaacttc atgctttaga aaaacagttt tcaaaggata    3420
catattctaa gccttcaatt tcaggaatag agtcagatga tcattgtcag agagaacagg    3480
agcttcagaa ggaaaacttg aagttgtcat ctgaaaatat tgaactgaaa tttcagcttg    3540
aacaagcaaa taagatttg  ccaagattaa agaatcaagt cagagatttg aaggaaatgt    3600
gtgaatttct taagaaagaa aaagcagaag ttcagcggaa acttggccat gttagagggt    3660
ctggtagaag tggaaagaca atcccagaac tggaaaaaac cattggttta atgaaaaaag    3720
tagttgaaaa agtccagaga gaaaatgaac agttgaaaaa agcatcagga atattgacta    3780
gtgaaaaaat ggctaatatt gagcaggaaa atgaaaaatt gaaggctgaa ttagaaaaac    3840
ttaaagctca tcttgggcat cagttgagca tgcactatga atccaagacc aaaggcacag    3900
aaaaaattat tgctgaaaat gaaaggcttc gtaaagaact taaaaagaa  actgatgctg    3960
cagagaaatt acggatagca aagaataatt tagagatatt aaatgagaag atgacagttc    4020
aactagaaga gactggtaag agattgcagt ttgcagaaag cagaggtcca cagcttgaag    4080
gtgctgacag taagagctgg aaatccattg tggttacaag aatgtatgaa accaagttaa    4140
aagaattgga aactgatatt gccaaaaaaa atcaaagcat tactgacctt aaacagcttg    4200
taaagaagc  aacagagaga gaacaaaaag ttaacaaata caatgaagac cttgaacaac    4260
agattaagat tcttaaacat gttcctgaag gtgctgagac agagcaaggc cttaaacggg    4320
agcttcaagt tcttagatta gctaatcatc agctggataa agagaaagca gaattaatcc    4380
atcagataga agctaacaag gaccaaagtg gagctgaaag caccataccct gatgctgatc    4440
aactaaagga aaaaataaaa gatctagaga cacagctcaa aatgtcagat ctagaaaagc    4500
agcatttgaa ggaggaaata aagaagctga aaaagaact  ggaaaatttt gatccttcat    4560
```

```
                                        -continued
tttttgaaga aattgaagat cttaagtata attacaagga agaagtgaag aagaatattc    4620
tcttagaaga gaaggtaaaa aaactttcag aacaattggg agttgaatta actagccctg    4680
ttgctgcttc tgaagagttt gaagatgaag aagaaagtcc tgttaatttc cccatttact    4740
aaagatctac atctcgcttt cttgctgtcc aatttctatt aaaggttcct ttgttcccta    4800
agtccaacta ctaaactggg ggatattatg aagggccttg agcatctgga ttctgcctaa    4860
taaaaaacat ttattttcat tgcaatgatg tatttaaatt atttctgaat attttactaa    4920
aaagggaatg tgggaggtca gtgcatttaa aacataaaga aagtaggtaa ccacgtgcgg    4980
accgagcggc cgcaggaacc cctagtgatg gagttggcca ctccctctct gcgcgctcgc    5040
tcgctcactg aggccgggcg accaaaggtc gcccgacgcc cgggctttgc ccgggcggcc    5100
tcagtgagcg agcgagcgcg cagctgcctg ca                                  5132
```

METHODS AND COMPOSITIONS FOR TREATING LEBER CONGENITAL AMAUROSIS

CROSS REFERENCE TO RELATED APPLICATIONS

This application is a divisional of U.S. patent application Ser. No. 15/506,323, filed Feb. 24, 2017, which is a national stage application under 35 U.S.C. 371 and claims the benefit of PCT Application No. PCT/US2015/047209 having an international filing date of 27 Aug. 2015, which designated the United States, which PCT application claimed the benefit of the U.S. Provisional Application No. 62/042,703, filed 27 Aug. 2014, the disclosure of each of which are incorporated herein by reference.

REFERENCE TO SEQUENCE LISTING

This application contains a Sequence Listing submitted as an electronic text file named "6137NEI-2-PUS-D1_Sequence_Listing_ST25.txt", having a size in bytes of 236 KB, and created on May 28, 2019. The information contained in this electronic file is hereby incorporated by reference in its entirety pursuant to 37 CFR § 1.52(e)(5).

TECHNICAL FIELD

The invention relates to gene therapy and expression vectors and therapeutic methods of using such vectors in the treatment of diseases of the eye resulting from failure to produce a specific protein in the eye, or the production of a non-functional protein in the eye.

BACKGROUND

Leber congenital amaurosis (LCA) is an inherited eye disorder that primarily affects the retina, a specialized neuronal tissue at the back of the eye that detects light and color. People with this disease have severe visual impairment beginning in infancy. It occurs in 1 per 50,000 newborns and is one of the most common causes of blindness in children. So far, LCA-disease causing mutations have been identified in twenty-one genes. Mutations in the Centrosomal Protein 290 (CEP290) (NP_079390) gene account for 20-25 percent of LCA, afflicting an estimated 20,000 people worldwide. There is no treatment for this disease to date.

In recent years, gene therapy has emerged as a promising treatment modality for inherited eye disorders. Functional improvement has been achieved by gene therapy in patients with mutations in another gene, RPE65, which accounts for about 5% of LCA. Gene therapy for CEP290-related LCA (i.e., LCA caused by mutations in the CEP290 gene) has not been successful, even in animal models of the disease. A major reason for this lack of success is the difficulty of delivering the correct copy of CEP290 gene into the diseased retina due to the large size of the complete coding region. To treat LCA patients with CEP290 mutations, a correct copy of the CEP290 gene needs to be transferred into the patients' photoreceptor cells in their retinas. But the 7.4 kb size of the wild-type CEP290 cDNA significantly hampers its delivery into photoreceptors in the eye. Consequently, there is a need for an efficient treatment of CEP290-realted LCA. The present invention addressees this need and achieves other advantages, which are discussed more fully below.

SUMMARY OF THE INVENTION

The present disclosure provides expression vectors and therapeutic methods of using the vectors for gene therapy to improve the visual function of a patient suffering from diseases of the eye, particularly Leber Congenital Amaurosis (LCA) and CEP290-related LCA. The invention relates to the inventors' surprising discovery that only a portion of the CEP290 coding region is necessary to restore proper CEP290 function in the eye, thereby improving visual function in individuals suffering from CEP290-related LCA.

Thus, one aspect of this disclosure is an isolated deoxyribonucleic acid (DNA) molecule comprising a nucleotide sequence at least 95% identical to at least a portion of a CEP290 open reading frame (ORF), wherein the nucleotide sequence encodes a protein that, when expressed in the photoreceptor cells of a patient suffering from CEP290-related Leber congenital amaurosis (LCA), increases the visual function of the patient. The portion of the CEP290 ORF may be less than a full-length CEP290 ORF. The portion of the CEP290 ORF may be less than 500 nucleotides in length. The CEP290 protein may be human CEP290. The portion of a CEP290 ORF may consist of SEQ ID NOs:4 or 10. The portion of CEP290 ORF may encode a protein at least 95% identical to SEQ ID NOs:4 or 10. The nucleotide sequence may encode a protein at least 95% identical to SEQ ID NOs:5 or 11 (referred to as the "myosin tail"; see FIG. 1). The nucleotide sequence may encode a protein comprising SEQ ID NOs:5 or 11. The nucleotide sequence may encode a protein comprising SEQ ID NO:8. The nucleotide sequence may be functionally linked to a photoreceptor cell-specific promoter.

Another aspect of this disclosure is a plasmid comprising the isolated DNA molecule comprising a nucleotide sequence at least 95% identical to at least a portion of a CEP290 gene open reading frame (ORF), wherein the nucleotide sequence encodes a protein that when expressed in the photoreceptor cells of a patient suffering from CEP290-related LCA, increases the visual function of the patient.

Another aspect of this disclosure is a vector comprising a deoxyribonucleic acid (DNA) molecule comprising a nucleotide sequence at least 95% identical to at least a portion of a CEP290 open reading frame (ORF), wherein the nucleotide sequence encodes a protein that when expressed in the photoreceptor cells of a patient suffering from CEP290-related LCA, increases the visual function of the patient. In these aspects, the vector may be a virus. The virus may be capable of transducing photoreceptor cells. The vector may be an adeno-associated virus. The vector may be a viral vector selected from the group consisting of AAV1, AAV2, AAV3, AAV5, AAV6, AAV7, AAV8, AAV9, and AAV10. The CEP290 may be human CEP290. The portion of a CEP290 ORF may consist of SEQ ID NO:4 or 10. The portion of a CEP290 ORF may encode a protein at least 95% identical to SEQ ID NO:11. The nucleotide sequence may encode a protein at least 95% identical to SEQ ID NO:5 or 11. The nucleotide sequence may encode a protein comprising SEQ ID NO:5 or 11. The nucleotide sequence may be functionally linked to a photoreceptor cell-specific promoter.

Another aspect of this disclosure is a pharmaceutical composition comprising a vector comprising a deoxyribonucleic acid (DNA) molecule comprising a nucleotide sequence at least 95% identical to at least a portion of a CEP290 open reading frame (ORF), wherein the nucleotide sequence encodes a protein that when expressed in the photoreceptor cells of a patient suffering from CEP290-related LCA, increases the visual function of the patient.

Another aspect of this disclosure provides methods of improving the visual function of a patient having CEP290-related LCA comprising administering an isolated DNA molecule comprising a nucleotide sequence at least 95% identical to at least a portion of a CEP290 open reading frame (ORF) to a patient in need thereof. The CEP290 may be human CEP290. The portion of a CEP290 ORF may consist of SEQ ID NO: 10. The portion of a CEP290 ORF may encode a protein at least 95% identical to SEQ ID NO:11. The nucleotide sequence may encode a protein at least 95% identical to SEQ ID NO:11. The nucleotide sequence may encode a protein comprising SEQ ID NO:11. The nucleotide sequence may be functionally linked to a photoreceptor cell-specific promoter. The isolated DNA molecule may be administered as naked DNA. The isolated DNA molecule may be coated with a transfection agent. The isolated DNA molecule may be in the form of a plasmid. The isolated DNA molecule may be administered in a viral vector. The viral vector is preferably capable of transducing photoreceptor cells. The administering may include subretinal injection of the isolated DNA molecule. The administering may include intravitreal injection of the isolated DNA molecule. Related aspects of this disclosure provide the use of an isolated DNA molecule comprising SEQ ID NO:10 in the manufacture of a medicament for the treatment of CEP290-related Leber Congenital Amaurosis. Another aspect provides an isolated DNA molecule comprising SEQ ID NO:10 for use in the treatment of CEP290-related Leber Congenital Amaurosis.

This Summary of the Invention is neither intended nor should it be construed as being representative of the full extent and scope of the invention. Aspects of the present invention are set forth in various levels of detail in this disclosure and no limitation as to the scope of the present invention is intended by either the inclusion or non-inclusion of elements, components, etc. in this Summary. Additional aspects of the present invention will become more readily apparent from the Description of Embodiments, particularly when taken together with the drawings.

BRIEF DESCRIPTION OF DRAWINGS

FIG. 2a shows the results of administration of the DSD fragment vector; FIG. 2b shows the results of administration of the myosin tail fragment vector; FIG. 2c shows the results of administration of the c-terminal vector. The control eyes were injected with an equal dose of viral particle with no expression cassette (null vector).

FIG. 3a shows the results of administration of 5e8 vg/eye of the myosin tail fragment vector; FIG. 3b shows the results of administration of 1e9 vg/eye of the myosin tail fragment vector; FIG. 3c shows the results of administration of 2e9 vg/eye of the myosin tail fragment vector.

DESCRIPTION OF EMBODIMENTS

Figure 1:
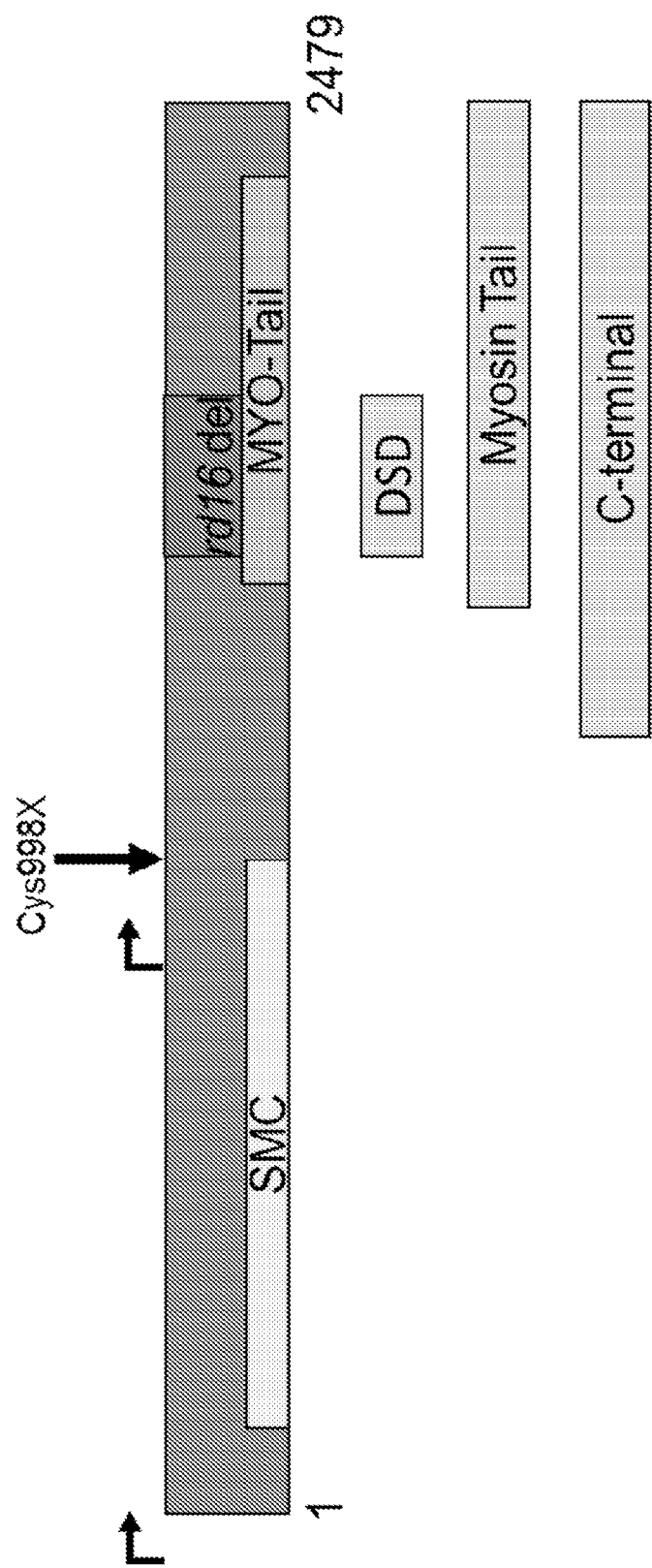
FIG. 1 is a schematic of the full-length CEP290 protein and the length and position of three CEP290 protein fragments (DSD, Myosin Tail, and C-terminal fragments) referenced in this disclosure. The position of the retinal dystrophy-16 (rd16) portion of the CEP290 protein is indicated. This portion of the CEP290 protein is absent in the Cep290 protein expressed by Cep290$^{rd16}$ mice, which have a phenotype that resembles LCA. The position of one CEP290 mutation (Cys998X), a splice-site change resulting in a premature stop codon, is also indicated. A region that has homology to SMC chromosome segregation ATPases, is also indicated.

The present disclosure relates to novel methods and compositions for treating Leber congenital amaurosis (LCA). More specifically, the present disclosure relates to novel nucleic acid molecules, and proteins encoded therein, that when administered to a patient suffering from LCA resulting from mutations in the CEP290 gene (herein "CEP290-realted LCA"), are capable of improving visual function in the patient. The present invention also relates to vectors for administering such nucleic acid molecules as well as methods of administering such vectors in order to improve the visual function of a patient suffering from CEP290-related LCA.

As used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation The publications discussed herein are provided solely for their disclosure prior to the filing date of the present application. Nothing herein is to be construed as an admission that the present invention is not entitled to antedate such publication by virtue of prior invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

Previous attempts at treating CEP290-related LCA through the use of gene therapy have been unsuccessful due in large part to the difficulty in delivering the CEP290 coding region into the eye of the patient. In particular, the coding sequence for the full-length CEP290 protein is 7.4 kilobases (kb) in length, making it difficult to package the entire coding region into a single vector. The present inventors have surprisingly discovered that only a portion of the CEP290 coding region is necessary to restore proper CEP290 function and thus, improve visual function in individuals suffering from CEP290-related LCA. Thus, one aspect of the present invention is an isolated nucleic acid molecule (e.g., deoxyribonucleic acid (DNA) molecule) comprising a portion of a CEP290 open reading frame (ORF), wherein the portion of the CEP290 ORF is no more than about 5,000 nucleotides in length, and wherein the portion of the CEP290 ORF encodes a protein that is able to bind BBS6 protein, or that when expressed in photoreceptor cells in a patient suffering from CEP290-related LCA, increases the visual function of the patient.

As used herein, and with particular regard to amino acid and nucleotide sequences, the term "about" refers to a variation of +/−10%.

As used herein, "a portion of a CEP290 ORF" refers to at least 500 contiguous nucleotides from a CEP290 ORF, wherein the at least 500 contiguous nucleotides encode a protein having at least one activity specified herein, and wherein the portion of a CEP290 ORF does not comprise a full-length CEP290 ORF. That is, the portion of a CEP290 ORF is less than a full-length CEP290 ORF. The portion of the CEP290 ORF may comprise at least about 1,000, at least about 1,500, at least about 2,000, at least about 2,500, at least about 3,000, at least about 3,500, at least about 4,000, a least about 4,500 or at least about 5,000 contiguous nucleotides from a CEP290 ORF. Similarly, the portion of a CEP290 ORF may be less than about 4,500 nucleotides, less than about 4,000 nucleotides, less than about 3500 nucleotides, less than about 3,400 nucleotides, less than about 3,300 nucleotides, about 3,200 nucleotides, less than about 3,100, less than about 3,000 nucleotides, less than about 2,900 nucleotides, less than about 2,800 nucleotides, less than about 2,700, less than about 2,600 nucleotides, less than about 2,500 nucleotides, less than about 2,400 nucleotides, less than about 2,300 nucleotides, less than about 2,200 nucleotides, less than about 2,100, less than about 2,000 nucleotides, less than about 1,900 nucleotides, about 1,800 nucleotides, less than about 1,700 nucleotides, less than 1,600 nucleotides or less than about 1,500 nucleotides in length.

According to the present invention, a CEP290 open reading frame (ORF) refers to a series of contiguous nucleotides that does not contain any intron sequences or stop codons, and which encode a full-length CEP290 protein. The portion of a CEP290 ORF can be obtained from the CEP290 ORF of any animal, so long as the encoded protein possesses the desired activity. Desired activities include binding BBS6 protein (McKusick-Kaufman syndrome (MKS) and Bardet-Biedl syndrome (BBS) putative chaperonin protein) and/or improving the visual function of a patient suffering from CEP290-related LCA when the encoded protein is expressed in the cells of an eye of the patient. Examples of suitable animals from which to obtain the CEP290 sequence include, but are not limited to, humans and other primates, non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. In one embodiment, the portion of a CEP290 ORF is obtained from a mouse CEP290 ORF. One mouse CEP290 ORF is represented by SEQ ID NO:1, which encodes a CEP290 protein represented by SEQ ID NO:2. In a preferred embodiment, the portion of a CEP290 ORF is obtained from a human CEP290 ORF. A human CEP290 ORF is represented by SEQ ID NO:7, which encodes a CEP290 protein represented by SEQ ID NO:8. Representative examples of useful CEP290 genes, portions thereof, and other sequences useful for producing constructs of the present invention, are listed below in Table 1.

TABLE 1

| SEQ ID NO | Description |
|---|---|
| 1 | Nucleotide sequence encoding mouse CEP290 protein |
| 2 | Protein encoded by SEQ ID NO: 1 |
| 3 | Complement of SEQ ID NO: 1 |
| 4 | Nucleotide sequence encoding mouse CEP290 myosin tail (2970 nts) |
| 5 | Protein encoded by SEQ ID NO: 4 (989 aa) |
| 6 | Complement of SEQ ID NO: 4 |
| 7 | Nucleotide sequence encoding human CEP290 protein |
| 8 | Protein encoded by SEQ ID NO: 7 |
| 9 | Complement of SEQ ID NO: 7 |
| 10 | Nucleotide sequence encoding human CEP290 myosin tail (2973 nts) |
| 11 | Protein encoded by SEQ ID NO: 10 (990 aa) |
| 12 | Complement of SEQ ID NO: 10 |
| 13 | Sequence of AAV2 ITR -upstream |
| 14 | Sequence of AAV2 ITR -downstream |
| 15 | Sequence of AAV2 terminal resolution site (trs) |
| 16 | Sequence of AAV2 REP binding site (RBS) |
| 17 | Sequence of human rhodopsin kinase promoter |
| 18 | Sequence of CMV IE promoter |
| 19 | Nucleotide sequence encoding AAV8 Cap protein |
| 20 | Protein encoded by SEQ ID NO: 17 |

TABLE 1-continued

| SEQ ID NO | Description |
|---|---|
| 21 | Complement of SEQ ID NO: 17 |
| 22 | Nucleotide sequence encoding mouse CEP290 DSD region (nts 4816-5712 of SEQ ID NO: 1) (896 nts) |
| 23 | Protein encoded by SEQ ID NO: 22 (aa 1606-1904 of SEQ ID NO: 2) (299 aa) |
| 24 | Complement of SEQ ID NO: 22 |
| 25 | Nucleotide sequence encoding human CEP290 DSD region (nts 4813-5709 of SEQ ID NO: 7) |
| 26 | Protein encoded by SEQ ID NO: 25 (299 aa) (aa 1605-1903 of SEQ ID NO: 8) |
| 27 | Complement of SEQ ID NO: 25 |
| 28 | Nucleotide sequence encoding mouse CEP290 C-terminal region (nts 3517-7440 of SEQ ID NO: 1) (3924 nts) |
| 29 | Protein encoded by SEQ ID NO: 28 (1307 aa) |
| 30 | Complement of SEQ ID NO: 28 |
| 31 | Nucleotide sequence encoding human CEP290 C-terminal region (nts 3517-7440 of SEQID NO: 7) |
| 32 | Protein encoded by SEQ ID NO: 31 (1307 aa) |
| 33 | Complement of SEQ ID NO: 31 |
| 34 | Nucleotide sequence of expression cassette - CMV-Mouse Myo tail-poly A |
| 35 | Nucleotide sequence of expression cassette - CMV-Human Myo tail-poly A |
| 36 | Nucleotide sequence of expression cassette - CMV-Mouse DSD -poly A |
| 37 | Nucleotide sequence of expression cassette - CMV-Human DSD -poly A |
| 38 | Nucleotide sequence of expression cassette - CMV-Mouse C-terminal-poly A |
| 39 | Nucleotide sequence of expression cassette - CMV-Human C-terminal-poly A |
| 40 | Nucleotide sequence of mouse Myo tail AAV expression vector |
| 41 | Nucleotide sequence of human Myo tail AAV expression vector |
| 42 | Nucleotide sequence of mouse DSD AAV expression vector |
| 43 | Nucleotide sequence of human DSD AAV expression vector |
| 44 | Nucleotide sequence of mouse C-terminal AAV expression vector |
| 45 | Nucleotide sequence of human C-terminal AAV expression vector |

It will be appreciated by those skilled in the art that genes found in nature often contain polymorphisms. A polymorphism, or variant, refers to a nucleic acid molecule (or its encoded protein), the sequence of which is similar, but not identical, to a reference sequence, often referred to as the wild-type sequence. While some sequence variations result in the reduction or elimination of the activity of the encoded protein, many have minimal or no effect on the activity of the encoded protein. According to the present invention, the portion of a CEP290 ORF can be obtained from any polymorphic variant of a CEP290 ORF, so long as the portion encodes a protein that is capable of increasing the visual function of a patient suffering from CEP290 related LCA.

Variations in the sequence of a CEP290 ORF, or portions thereof, used in the present invention may also be made through the use of genetic engineering techniques known to those skilled in the art. Examples of such techniques may be found in Sambrook J, Fritsch E F, Maniatis T et al., in Molecular Cloning-A Laboratory Manual, 2nd Edition, Cold Spring Harbor Laboratory Press, 1989, pp. 9.31-9.57, or in Current Protocols in Molecular Biology, John Wiley & Sons, N.Y. (1989), 6.3.1-6.3.6. With regard to such variants, any type of alteration in the nucleic acid sequence is permissible so long as the resulting variant protein retains the ability to increase the visual function of a patient suffering from CPE290-related LCA. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxyl terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

Any variation in the sequence of these proteins is permissible so long as the ability of the variant protein to increase visual function in the specified LCA patient is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions. Naturally occurring residues may be divided into classes based on common side chain properties, as follows:

1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class.

In making amino acid changes in the protein encoded by the portion of a CPE290 ORF, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functional equivalent protein or peptide thereby created is intended for therapeutic uses, as in the present case. The greatest local average hydrophilicity of a protein, as governed by the hydrophilicity of its adjacent amino acids, correlates with its immunogenicity and antigenicity, i.e., with one biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred.

Desired amino acid substitutions (whether conservative or non-conservative) can be determined by those skilled in the art at the time such substitutions are desired. For example, amino acid substitutions can be used to identify important residues of the therapeutic protein, or to increase or decrease the immunogenicity, solubility or stability of the therapeutic proteins described herein. Exemplary amino acid substitutions are shown in the following table:

| Amino Acid Substitutions | |
| --- | --- |
| Original Amino Acid | Exemplary Substitutions |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase "significantly affect a protein's activity" refers to a decrease in the activity of a protein by at least 20%, at least 30%, at least 40% or at least 50%. Methods of measuring such activities are known to those skilled in the art.

The portion of a CEP290 ORF may include a nucleotide sequence at least 85%, at least 90%, at least 95%, at least 98% or at least 99% identical to at least 500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 750 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,000 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,800 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,900 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,000 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 4,000 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 4,500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 5,000 contiguous nucleotides from a CEP290 ORF, wherein the portion encodes a protein that is capable of increasing visual function in a patient suffering from CEP290-related LCA.

While any portion of a CEP290 ORF having one or more of the desired activities described above can be used in the methods of the present disclosure, the inventors have discovered that particular portions of a CEP290 ORF are more suitable than others in increasing visual function in a patient suffering from CEP290-related LCA. Portions of a CEP290 ORF region corresponding to nucleotides 4471-7440 of SEQ ID NO:1, which is represented by SEQ ID NO:4, or nucleotides 4468-7440 of SEQ ID NO:7, which is represented by SEQ ID NO:10, are examples of such particularly suitable portions. It will be appreciated by those skilled in the art that due to the polymorphic variations previously described, variant CEP290 proteins, or CEP290 proteins from different species, can have slightly different sequences and as a result, may differ in length or sequence by a few amino acid residues. Thus, while the overall sequences of two or more variants may be nearly identical, the same (i.e., corresponding) region (e.g., domain) in two or more variants may differ slightly in sequence or may be slightly shifted upstream or downstream within the amino acid sequence relative to one another due to insertions or deletions. For example, amino acid residues 5-50 in one CEP290 protein may correspond to amino acid residues 4-49, 3-49, 3-51, 3-52, 5-5 or 3-56 in a variant CEP290 protein. As a more specific example, amino acid residues 257-292 of CEP290 from several species are predicted to form an amphipathic helix that is believed to mediate membrane binding of the protein. The corresponding region in CEP290 from organisms in the Genus *Danio* (minnow-type fish) spans amino acids 252-287 (J. of Clin. Invest., Vol. 123, No. 10, 2013). Consequently, as used herein, a region of an ORF (or protein) corresponding to a specified sequence (reference sequence) refers to a polynucleotide (or amino acid) sequence in the ORF (or protein) that is identical, or nearly so (e.g., 2%, 4%, 6%, 8%, 10%, 15% or 20% variation in sequence), in sequence to the reference sequence and which encodes (or is) a domain having the same structure and/or function.

Thus, the portion of a CEP290 ORF may include a nucleotide sequence at least 85%, at least 90%, at least 95%, at least 98% or at least 99% identical to at least 1,000, at least 1,500, at least 2,000, at least 2,500, at least 2,700, at least 2,800 or at least 2,900 contiguous nucleotides from region of a CEP290 ORF encoding the myosin tail domain (FIG. 1). Thus, the portion of a CEP290 ORF may include a nucleotide sequence at least 85%, at least 90%, at least 95%, at least 98% or at least 99% identical to at least 1,000 contiguous nucleotides from the region of a CEP290 ORF corresponding to nucleotides 4471-7440 of SEQ ID NO:1 or nucleotides 4468-7440 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,000 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 1,500 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,500 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,000 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,500 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,700 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,800 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,800 contiguous nucleotides from SEQ ID NO:4 or SEQ ID NO:10, wherein the portion encodes a protein that is capable of increasing visual function in a patient suffering from CEP290-related LCA.

The portion of a CEP290 ORF comprises a nucleotide sequence at least 85%, at least 90%, at least 95%, at least 98% or at least 99% identical to at least 2,900 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,900 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include the nucleotide sequence of SEQ ID NO:4 or SEQ ID NO:10. In specific embodiments, the portion of a CEP290 ORF consists of SEQ ID NO:4 or SEQ ID NO:10.

As noted above, an isolated DNA molecule of the present invention encodes at least a portion of a CEP290 protein that is capable of increasing the visual function in a patient suffering from CEP290-related LCA. The portion of a CEP290 ORF may encode a protein comprising an amino acid sequence at least 85%, at least 90%, at least 95%, at least 97% or at least 99% identical to at least 500 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 600 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 700 contiguous amino acid residues from SEQ ID NO:5 or SEQ ID NO:11. The portion of a CEP290 ORF may encode a protein comprising an amino acid sequence at least 85%, at least 90%, at least 95%, at least 97% or at least 99% identical to at least 800 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 900 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 950 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 960 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 970 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 980 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to SEQ ID NO:5 or SEQ ID NO:11, wherein the portion of the CEP290 protein is capable of increasing visual function in a patient suffering from CEP290-related LCA. The portion of a CEP290 ORF may encode a protein comprising SEQ ID NO:5 or SEQ ID NO:11. The portion of a CEP290 ORF may also encode a protein consisting of SEQ ID NO:5 or SEQ ID NO:11.

The portion of a CEP290 ORF may include a nucleotide sequence at least 85%, at least 90%, at least 95%, at least 98% or at least 99% identical to at least 300, at least 350, at least 400, at least 450, at least 500, at least 550, at least 600, at least 650, at least 700, at least 750, at least 800, or at least 850 contiguous nucleotides from the "deleted in sensory dystrophy" (DSD) domain of CEP290 ORF (FIG. 1). The portion of a CEP290 ORF may include a CEP290 ORF region corresponding to nucleotides 4816-5712 of SEQ ID NO:1, which is represented by SEQ ID NO:22, or nucleotides 4813-5709 of SEQ ID NO:7, which is represented by SEQ ID NO:25. The portion of a CEP290 ORF may include a nucleotide sequence at least 85%, at least 90%, at least 95%, at least 98% or at least 99% identical to at least 300 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF comprises a nucleotide sequence at least 85%, at least 90%, at least 95%, at least 98% or at least 99% identical to at least 300 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 350 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 350 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 400 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 400 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 450 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 450 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 500 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 500 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 550 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 550 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 600 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 600 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 650 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 650 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 700 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 700 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 750 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 750 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 800 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 800 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 850 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 850 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include SEQ ID NO:22 or SEQ ID NO:25. In specific embodiments, the portion of a CEP290 ORF consists of SEQ ID NO:22 or SEQ ID NO:25.

In one embodiment, an isolated DNA molecule of the present invention encodes protein comprising an amino acid sequence at least 85%, at least 90%, at least 95%, at least 97% or at least 99% identical to at least 100 contiguous amino acids, at least 150 contiguous amino acids, at least 200 contiguous amino acids, at least 250 contiguous amino acids, at least 275 contiguous amino acids or at least 290 contiguous amino acids, from a region of a CEP290 protein corresponding to the "deleted in sensory dystrophy" (DSD) domain (FIG. 1).

The portion of a CEP290 ORF encodes a protein comprising an amino acid sequence at least 85%, at least 90%, at least 95%, at least 97% or at least 99% identical to at least 100 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 150 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 200 contiguous amino acid residues from SEQ ID NO:23 or SEQ ID NO:26. The portion of a CEP290 ORF encodes a protein comprising an amino acid sequence at least 85%, at least 90%, at least 95%, at least 97% or at least 99% identical to at least 250 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 275 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 290 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to SEQ ID NO:23 or SEQ ID NO:26, wherein the CEP290 protein is capable of increasing visual function in a patient suffering from CEP290-related LCA. The portion of a CEP290 ORF encode a protein comprising an amino acid sequence comprising SEQ ID NO:23 or SEQ ID NO:26. The portion of a CEP290 ORF encode a protein consisting of SEQ ID NO:23 or SEQ ID NO:26.

The portion of a CEP290 ORF may include a nucleotide sequence at least 85%, at least 90%, at least 95%, at least 98% or at least 99% identical to at least 1,000, at least 1,500, at least 2,000, at least 2,500, at least 3,000, at least 3,200, at least 3,500, at least 3,700, at least 3,800 or at least 3,900 contiguous nucleotides from the region of the CEP290 ORF encoding the C-Terminal domain (FIG. 1). The portion of a CEP290 ORF may include a CEP290 ORF region corresponding to nucleotides 3517-7440 of SEQ ID NO:1, which is represented by SEQ ID NO:28, or nucleotides 3517-7440 of SEQ ID NO:7, which is represented by SEQ ID NO:31. The portion of a CEP290 ORF may include a nucleotide sequence at least 85%, at least 90%, at least 95%, at least 98% or at least 99% identical to at least 1,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,000 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 1,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,200 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,200 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,700 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,700 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,800 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,800 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,900 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,900 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include SEQ ID NO:28 or SEQ ID NO:31. In specific embodiments, the portion of a CEP290 ORF consists of SEQ ID NO:28 or SEQ ID NO:31.

As noted above, an isolated DNA molecule of the present invention encodes a CEP290 protein that is capable of increasing the visual function in a patient suffering from CEP290-related LCA. The portion of a CEP290 ORF encodes a protein comprising an amino acid sequence at least 85%, at least 90%, at least 95%, at least 97% or at least 99% identical to at least 500 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 600 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 700 contiguous amino acid residues from SEQ ID NO:28 or SEQ ID NO:31. The portion of a CEP290 ORF encodes a protein comprising an amino acid sequence at least 85%, at least 90%, at least 95%, at least 97% or at least 99% identical to at least 800 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 900 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1000 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1,100 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1,200 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1,250 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1,300 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to SEQ ID NO:28 or SEQ ID NO:31, wherein the CEP290 protein is capable of increasing visual function in a patient suffering from CEP290-related LCA. The portion of a CEP290 ORF encode a protein comprising SEQ ID NO:28 or SEQ ID NO:31. The portion of a CEP290 ORF encode a protein consisting of SEQ ID NO:28 or SEQ ID NO:31.

Isolated DNA molecules of the present invention are useful for expressing CEP290 protein when introduced into the eye of a patient suffering from CEP290-related LCA in such a manner suitable for delivery of the DNA molecules to cells of the eye. Thus, preferred DNA molecules of the present invention include a promoter sequence that is functionally linked to the portion of a CEP290 ORF. As used herein, the term functionally linked refers to the fact that the promoter is connected to a nucleotide sequence containing an open-reading frame such that when the construct is placed into the appropriate conditions, the promoter causes transcription (expression) of the open reading frame. Any promoter can be used so long as it is capable of driving expression of the ORF. Because molecules of the present invention are meant for treating conditions of the eye, preferred promoters are those that are functional in cells of the eye. The promoter is functional when introduced into the eye of a patient. The promoter is specific for cells of the eye. The promoter is functional when introduced into photoreceptor cells. The promoter is specific for photoreceptor cells.

The promoter is a rhodopsin promoter. The promoter is a rhodopsin kinase promoter. The promoter sequence may include SEQ ID NO:17. The promoter may be an Interstitial retinol-binding protein (IRBP promoter). The promoter may be a cytomegalovirus (CMV) promoter. The promoter may be a CMV intermediate-early (IE) promoter. The promoter may be a sequence consisting of SEQ ID NO:18.

One aspect of the present disclosure is a vector comprising an isolated DNA molecule of the present disclosure. As used herein, a vector is any agent comprising an isolated DNA molecule of the present disclosure that can be used to deliver a DNA molecule of the present disclosure into a cell. Examples of suitable vectors include, but are not limited to, plasmids, cosmids, phage and viruses. In one aspect, the vector is a virus. It will be appreciated by those skilled in the art that, in some instances, packaging of heterologous DNA into a virus requires specific sequences from the DNA of the virus into which the heterologous DNA is being packaged. Thus, an isolated DNA molecule of the present invention may include viral DNA that allows for packaging of the isolated DNA molecule into a virus. Any viral vector can be used to package isolated DNA of the present invention, so long as the virus is capable of containing the DNA and delivering it to the cells of an eye of a patient in need of such treatment.

One example of a suitable viral vector for use in the present invention is adeno-associated virus. Adeno-associated viruses are small, replication-defective, non-enveloped viruses that belong to the family Parvoviridae. The Parvoviridae family is characterized by having a single-stranded linear DNA genome of about 4,800 nucleotides and a small icosahedral shaped capsid measuring about 20 nm in diameter. The AAV genome contains two open reading frames called 'rep' and 'cap.' The rep ORF encodes all of the non-structural proteins that are necessary for replication and packaging of the viral genome, while the cap ORF encodes the viral capsid proteins. The viral capsid proteins are the structural proteins of the virus and assemble into the viral particle.

The AAV genome is terminated at each end by an inverted terminal repeat (ITR) of approximately 150 nucleotides in length. The sequences of the ITRs are palindromes that fold back on themselves to form T-shaped hairpin structures. Each ITR contains a Rep binding site (RBS) and a sequence referred to as the terminal resolution site (trs), which is cleaved by the viral Rep protein. These sequences in the ITR are important for replication and packaging of the viral genome. Thus, the ITRs can be combined with DNA molecules of the present invention to produce nucleic acid molecules that can be packaged into AAV particles and/or virus-like particles. Similar use of ITRs is described in U.S. Pat. No. 8,927,269, the entirety of which is incorporated herein by reference. Thus, an isolated DNA molecule of the present invention may be flanked by ITR sequences, wherein at least one ITR comprises AAV sequences that allow packaging of the DNA molecule into an AAV particle. The AAV sequences may be from an AAV ITR. At least one ITR may include an AAV RBS and a trs. At last one ITR may include SEQ ID NO:16 and SEQ ID NO:15. At least one ITR may be at least 85%, at least 90%, at least 95% or at least 97% identical to an AAV ITR, wherein the ITR comprises a RBS and a trs. An isolated DNA molecule of the present disclosure may be flanked by ITRs from an AAV virus. The ITRs can contain sequence from any AAV, so long as the virus strain from which the ITRs are obtained is capable of delivering the packaged DNA into a cell of the eye. An isolated DNA molecule of the present invention may be flanked by ITRs from a virus selected from the group consisting of AAV2, AAV3, AAV5, AAV6, AAV7, AAV8, AAV9 and AAV10. The ITRs may include a sequence selected from SEQ ID NO:13 and SEQ ID NO:14.

One aspect of the present disclosure is an isolated nucleic acid molecule of the present invention flanked by ITRs. Another aspect of the present invention is an isolated nucleic acid molecule comprising: a) a pair of inverted terminal repeats (ITRs), each of which is capable of forming a T-shaped hairpin structure, wherein at least one inverted terminal repeat comprises an AAV RBS and an AAV trs; and, b) a polynucleotide sequence between the terminal repeats, wherein the polynucleotide sequence comprises at least a portion of a CEP290 protein. Examples of suitable portions of a CEP290 protein have been described above.

Another aspect of this disclosure is an isolated nucleic acid molecule comprising: a) a pair of inverted terminal repeats (ITRs), each of which is capable of forming a T-shaped hairpin structure, wherein at least one inverted terminal repeat comprises an AAV RBS and an AAV trs; and, b) a polynucleotide sequence between the terminal repeats, wherein the polynucleotide sequence comprises at least a portion of a CEP290 ORF functionally linked to a promoter, wherein the portion of the CEP290 ORF is no more than 5000 nucleotides in length and encodes a protein that when expressed in the photoreceptor cells of a patient suffering from CEP-290-related LCA, increases the visual function of the patient. The AAV trs may include SEQ ID NO:15. The AAV RBS may include SEQ ID NO:16. Each ITR may include an AAV RBS and an AAV tsr. The ITRs may independently include a nucleic acid sequence at least 80% identical to an ITR from a virus selected from the group consisting of AAV2, AAV3, AAV5, AAV6, AAV7, AAV8, AAV9 and AAV10, wherein at least one ITR comprises an AAV Rep site and an AAV trs. The ITRs may independently include a nucleic acid sequence at least 95% identical to an ITR from a virus selected from the group consisting of AAV2, AAV3, AAV5, AAV6, AAV7, AAV8, AAV9 and AAV10, wherein at least one ITR comprises an AAV Rep site and an AAV trs. The ITRs may independently include an ITR from a virus selected from the group consisting of AAV2, AAV3, AAV5, AAV6, AAV7, AAV8, AAV9 and AAV10. The ITRs may include a sequence selected from SEQ ID NO:13 and SEQ ID NO:14.

The portion of CEP290 ORF may include a nucleotide sequence at least 85%, at least 90%, at least 95%, at least 98% or at least 99% identical to at least 1,000 contiguous nucleotides from the region of a CEP290 ORF corresponding to nucleotides 4471-7440 of SEQ ID NO:1 or nucleotides 4468-7440 of SEQ ID NO:7, wherein the portion encodes a protein that is capable of increasing visual function in a patient suffering from CEP290-related LCA. The portion of CEP290 ORF may include a nucleotide sequence at least 85%, at least 90%, at least 95%, at least 98% or at least 99% identical to at least 1,000 contiguous nucleotides from SEQ ID NO:4 or SEQ ID NO:10, wherein the portion encodes a protein that is capable of increasing visual function in a patient suffering from CEP290-related LCA.

The portion of CEP290 ORF may include a nucleotide sequence at least 85%, at least 90%, at least 95%, at least 98% or at least 99% identical to at least 1,500 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of CEP290 ORF may include a nucleotide sequence at least 85%, at least 90%, at least 95%, at least 98% or at least 99% identical to at least 1,500 contiguous nucleotides from SEQ ID NO:4 or SEQ ID NO:10, wherein the portion encodes a protein that is capable of increasing visual function in a patient suffering from CEP290-related LCA.

The portion of CEP290 ORF may include a nucleotide sequence at least 85%, at least 90%, at least 95%, at least 98% or at least 99% identical to at least 2,000 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,500 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,700 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,800 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,800 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,900 contiguous nucleotides from the region of a CEP290 ORF corresponding to 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,900 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include SEQ ID NO:4 or SEQ ID NO:10. In specific embodiments, the portion of CEP290 ORF consists of SEQ ID NO:4 or SEQ ID NO:10.

The portion of a CEP290 ORF may include a nucleotide sequence at least 85%, at least 90%, at least 95%, at least 98% or at least 99% identical to at least 300, at least 350, at least 400, at least 450, at least 500, at least 550, at least 600, at least 650, at least 700, at least 750, at least 800, or at least 850 contiguous nucleotides from the DSD domain of CEP290 ORF. The portion of a CEP290 ORF may include a CEP290 ORF region corresponding to nucleotides 4816-5712 of SEQ ID NO:1, which is represented by SEQ ID NO:22, or nucleotides 4813-5709 of SEQ ID NO:7, which is represented by SEQ ID NO:25. The portion of a CEP290 ORF may include a nucleotide sequence at least 85%, at least 90%, at least 95%, at least 98% or at least 99% identical to at least 300 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 300 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 350 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 350 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 400 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 400 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 450 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 450 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 500 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 500 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 550 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 550 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 600 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 600 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 650 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 650 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 700 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 700 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 750 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 750 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 800 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 800 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 850 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 850 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include SEQ ID NO:22 or SEQ ID NO:25. In specific embodiments, the portion of a CEP290 ORF consists of SEQ ID NO:22 or SEQ ID NO:25.

An isolated DNA molecule of the present disclosure may encode protein comprising an amino acid sequence at least 85%, at least 90%, at least 95%, at least 97% or at least 99% identical to at least 100 contiguous amino acids, at least 150 contiguous amino acids, at least 200 contiguous amino acids, at least 250 contiguous amino acids, at least 275 contiguous amino acids or at least 290 contiguous amino acids, from a region of a CEP290 protein corresponding to the DSD region.

The portion of a CEP290 ORF may encode a protein comprising an amino acid sequence at least 85%, at least 90%, at least 95%, at least 97% or at least 99% identical to at least 100 contiguous amino acid residues from SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 150 contiguous amino acid residues from SEQ ID NO:23 or SEQ ID NO:26, wherein the CEP290 protein is capable of increasing visual function in a patient suffering from CEP290-related LCA. The portion of a CEP290 ORF may endoce a protein comprising an amino acid sequence at least 85%, at least 90%, at least 95%, at least 97% or at least 99% identical to at least 200 contiguous amino acid residues from SEQ ID NO:23 or SEQ ID NO:26. The portion of a CEP290 ORF may encode a protein comprising an amino acid sequence at least 85%, at least 90%, at least 95%, at least 97% or at least 99% identical to at least 250 contiguous amino acid residues from SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 275 contiguous amino acid residues from SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 290 contiguous amino acid residues from SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence comprising SEQ ID NO:23 or SEQ ID NO:26. The portion of a CEP290 ORF may encode a protein consisting of SEQ ID NO:23 or SEQ ID NO:26.

The portion of a CEP290 ORF may include a nucleotide sequence at least 85%, at least 90%, at least 95%, at least 98% or at least 99% identical to at least 1,000, at least 1,500, at least 2,000, at least 2,500, at least 3,000, at least 3,200, at least 3,500, at least 3,700, at least 3,800 or at least 3,900 contiguous nucleotides from the region of the CEP290 ORF encoding the C-Terminal domain (FIG. 1). The portion of a CEP290 ORF may include a CEP290 ORF region corresponding to nucleotides 3517-7440 of SEQ ID NO:1, which is represented by SEQ ID NO:28, or nucleotides 3517-7440 of SEQ ID NO:7, which is represented by SEQ ID NO:31. The portion of a CEP290 ORF may include a nucleotide sequence at least 85%, at least 90%, at least 95%, at least 98% or at least 99% identical to at least 1,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,000 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 1,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,200 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,200 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,700 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,700 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,800 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,800 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,900 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,900 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include SEQ ID NO:28 or SEQ ID NO:31. The portion of a CEP290 ORF may consist of SEQ ID NO:28 or SEQ ID NO:31.

As noted above, an isolated DNA molecule of the present disclosure encodes a CEP290 protein that is capable of increasing the visual function in a patient suffering from CEP290-related LCA. The portion of a CEP290 ORF may encode a protein comprising an amino acid sequence at least 85%, at least 90%, at least 95%, at least 97% or at least 99% identical to at least 500 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 600 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 700 contiguous amino acid residues from SEQ ID NO:28 or SEQ ID NO:31. The portion of a CEP290 ORF may encode a protein comprising an amino acid sequence at least 85%, at least 90%, at least 95%, at least 97% or at least 99% identical to at least 800 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 900 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1000 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1,100 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1,200 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1,250 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1,300 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to SEQ ID NO:28 or SEQ ID NO:31, wherein the CEP290 protein is capable of increasing visual function in a patient suffering from CEP290-related LCA. The portion of a CEP290 ORF may encode a protein comprising SEQ ID NO:28 or SEQ ID NO:31. The portion of a CEP290 ORF may also encode a protein consisting of SEQ ID NO:28 or SEQ ID NO:31.

It is well appreciated in the art that the efficiency of delivery of nucleic acid molecules into cells can be increased using a delivery means such as a viral particle. Moreover, isolated DNA molecules of the present invention that comprise viral packaging sequences may be packaged into viral particles for use in delivering the CEP290 ORF to the eye of a patient in need of such treatment. As used herein, a viral particle refers to a particle comprising capsid proteins from one or more viruses, and which can encapsulate, or contain, isolated DNA containing the appropriate packaging sequences. Thus, one embodiment of the present invention is a virus particle comprising an isolated nucleic acid molecule of the present invention. In one embodiment, the viral particle comprises capsid proteins from an AAV. Such a particle can be referred to as an adeno-associated virus (AAV) particle. Thus, one embodiment of the present invention is an AAV particle comprising a nucleic acid molecule of the present invention. As noted previously, the AAV particle can be from any serotype of AAV as long as the virus particle is capable of delivering the isolated DNA of the present invention into a cell of the eye. In one embodiment, the virus particle is selected from the group consisting of AAV2, AAV3, AAV5, AAV6, AAV7, AAV8, AAV9 and AAV10. The general use of such particles is described in International Application No. PCT/US14/16389, the entirety of which is incorporated herein by reference.

Another aspect of this disclosure provides therapeutic compositions including isolated DNA molecules or viral particles of the present invention. Such compositions include physiologically acceptable solutions that comprise, for example, water, saline, salts, buffers, diluents, stabilizing agents, polymers, chelating agents and the like. One example of a physiologically acceptable solution is a solution comprising about 10 mM Tris-HCl (pH 7.4) and about 180 mM NaCl. It will be appreciated by those skilled in the art that such concentrations are approximate and may vary by as much as 10% or more, without significant affect on the efficacy of the composition.

One aspect of the invention provides methods of treating a patient having CEP290-related LCA. These methods include administering to the patient's eye an isolated DNA molecule of the present invention.

As used herein, the terms "patient," "individual" and "subject" are well-recognized in the art, and are used interchangeably to refer to any human or other animal in need of treatment of a disease of the eye. Examples include, but are not limited to, humans and other primates, non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. A preferred patient to treat is a human patient. The terms patient, individual and subject by themselves do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European.

Any method that delivers an isolated DNA molecule of the present invention into the eye of the patient can be employed. For example, in one embodiment, the isolated DNA is delivered as "naked" DNA. That is, the DNA can be injected into the eye such that it is taken up by the appropriate cells of the eye. Alternatively, the DNA may first be mixed with a lipid carrier such that, following injection of the DNA:lipid complex into the eye, the DNA enters the cells of the eye by transduction. Methods of delivering DNA to cells by transduction are known to those skilled in the art.

In one or more embodiments, an isolated DNA molecule of this disclosure is administered using a viral particle of the present disclosure. Thus, one embodiment of the present invention is a method of treating a patient having CEP290-related LCA, the method including administering to the eye of a patient having CEP290-related LCA a virus particle of the present invention. As noted above, virus particles of the present invention include nucleic acid molecules comprising at least a portion of a CEP290 ORF encoding a protein capable of improving visual function in a patient to whom it is administered. Thus, administration of a viral particle of the present invention will result in expression of the encoded portion of the CEP290 protein and subsequent improvement in visual function. In one embodiment, the viral particle is an AAV particle comprising a nucleic acid molecule of the present invention. Any method of administration can be used to deliver the expression vector, so long as the expression vector is delivered to the appropriate location of the eye resulting in expression of the encoded portion of the CEP290 protein.

In one or more embodiments, a nucleic acid molecule of the present invention is encapsulated in a viral particle that is able to traverse the outer layers of the eye (i.e., cornea, iris, sclera, pupil, lens, or conjunctiva) and enter into the intraocular fluid (also referred to as the aqueous humor). Thus, an isolated DNA molecule of the invention, either alone or in an encapsulated form, may be administered topically to the eye.

An isolated DNA molecule, either alone or in an encapsulated form, may be injected into the eye. This may include subconjunctival, sub-Tenon's, intravitreal, subretinal and intracameral injections. Such injections can deliver an isolated DNA molecule or a viral particle of the present invention to the intraocular fluid or to a location within the retina. In one embodiment, the injection delivers the isolated DNA, or a viral particle of the present invention, to the intraocular fluid. In one embodiment, the injection delivers the isolated DNA, or a viral particle containing the isolated DNA, into the retina. In specific embodiments, the isolated DNA, or a viral particle of the invention, is administered by intravitreal injection. In another embodiment, the isolated DNA, or a viral particle of the present invention, is administered by subretinal injection. In another embodiment, the isolated DNA, or a viral particle of the present invention, is administered by sub-Tenon's injection. Methods of performing intraocular injections are known to those skilled in the art. In all of these methods, the isolated DNA, or a viral particle of the present invention, is preferably contained within, and administered via a polypropylene syringe.

Another aspect of this disclosure provides a method of treating CEP290-related LCA in a human including administering to a human subject diagnosed with, or suspected of having, or being at risk of developing CEP290-related LCA, a therapeutically-effective amount of a vector of the present invention, wherein administration of the vector causes expression of a human CEP290 protein fragment of the invention in a cell in the eye of the human subject, and reduces at least one symptom of LCA. The vector may be administered as naked, or encapsulated, DNA. The vector may be administered as a viral particle. The vector may be an AAV particle comprising a nucleic acid molecule of the present invention. The cell in the eye may be a photoreceptor cell. The vector may be administered using intravitreal, subretinal or subtenon injection techniques.

The vector of the invention is administered in an amount that is therapeutically effective. When administered by injection, the single injection dosage may include between $1e^8$ nams/eye and $3e^{13}$ nams/eye (i.e., $1\times10^8$ nucleic acid molecules (nams) per eye to $3\times10^{13}$ nams per eye). When administered by these means, the single injection dosage may be between $3e^8$ nams/eye and $1e^{13}$ nams/eye, or between $1e^8$ nams/eye and $1e^{13}$ nams/eye, or between $3e^9$ nams/eye and $1e^{13}$ nams/eye, or between $1e^{10}$ nams/eye and $1e^{13}$ nams/eye, or between $3e^{10}$ nams/eye and $1e^{13}$ nams/eye, or between $1e^{11}$ nams/eye and $1e^{13}$ nams/eye, or between $3e^{11}$ nams/eye and $1e^{13}$ nams/eye, or between $1e^{12}$ nams/eye and $1e^{13}$ nams/eye, or between $3e^{12}$ nams/eye and $1e^{13}$ nams/eye.

The present invention also provides kits for practicing the disclosed methods. Kits of the present invention may include expression vectors of the present invention and viral vectors of the present invention. Such kits may also include reagents and tools necessary for practicing the disclosed methods, such as buffers, diluents, syringes, needles and instructions for administering such reagents.

While these aspects of this disclosure have been described with reference to preferred constructs, reagents and administration techniques, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

EXAMPLES

Example 1: Comparison of Therapeutic Effect of Different CEP290 Fragments in Rd16/Nrl KO Mice by Photopic Electroretinogram (ERG)

Figure 2A:
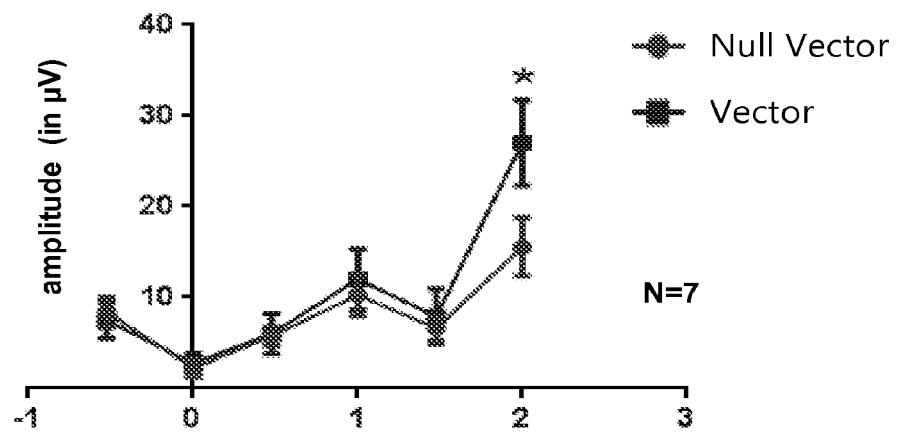
FIGS. 2a, 2b, and 2c show electroretinogram (ERG) data comparing the therapeutic effect of administration of the DSD, Myosin Tail, or C-terminal fragment.
Figure 2B:
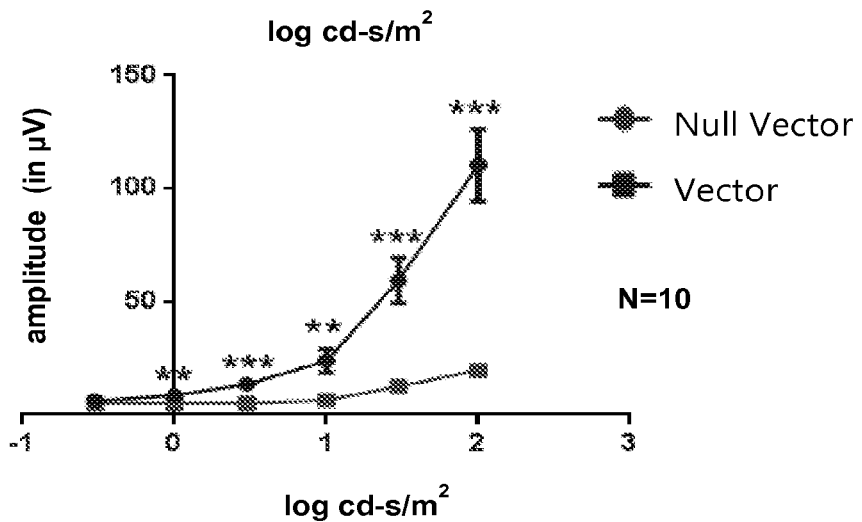
Figure 2C:
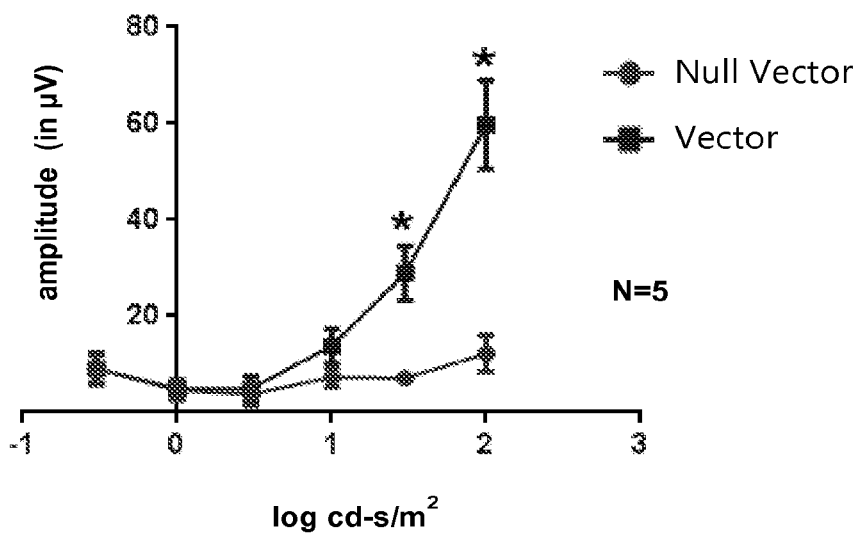

Two-week old mice were administered 8.8e8 AAV vector particles unilaterally through subretinal injection (results of administration of the DSD fragment vector are shown in FIG. 2a, results of administration of myosin tail fragment vector are shown in FIG. 2b, results of administration of c-terminal vector are shown in FIG. 2c). The control eyes were injected with an equal dose of viral particle with no expression cassette (null vector). The mice were followed by ERG 6 or 8 weeks after injection. These data demonstrate that the vector containing the Myosin-tail CEP290 protein fragment showed the best therapeutic effect.

Example 2: The Myosin-Tail Vector is Effective within a Wide-Dose Range

Figure 3A:
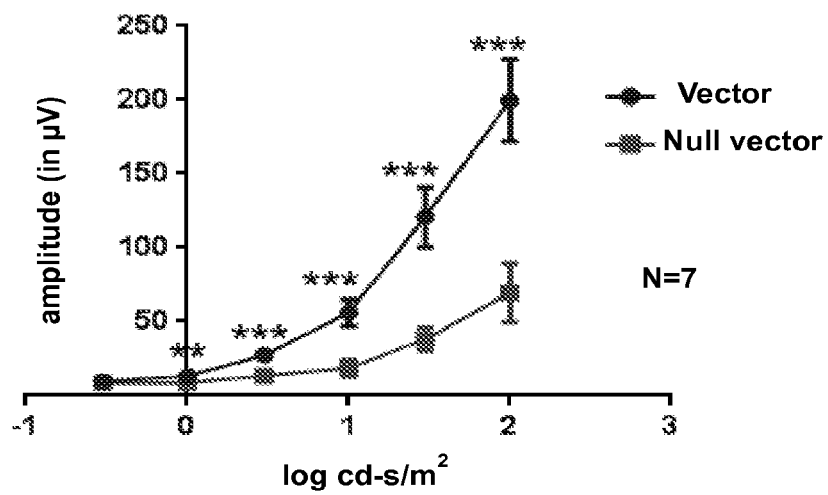
FIGS. 3a, 3b, and 3c show a dose-response study of the therapeutic effect of administration of the Myosin Tail fragment.
Figure 3B:
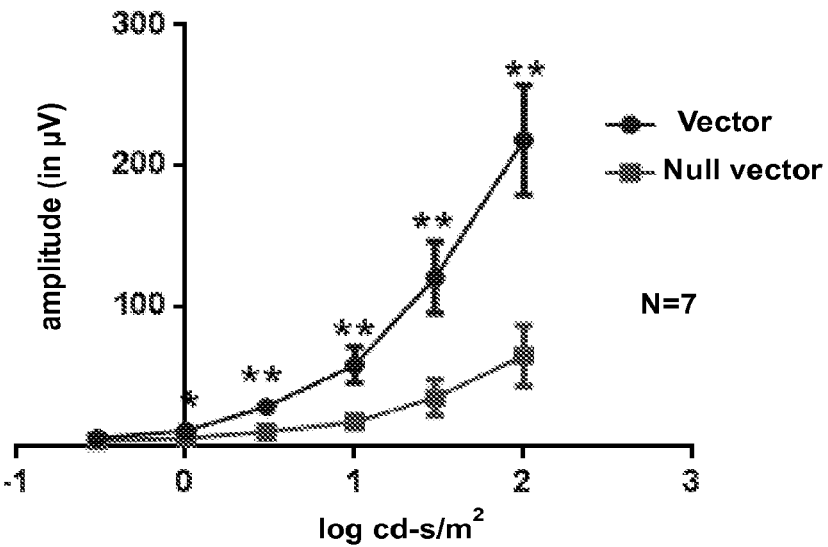
Figure 3C:
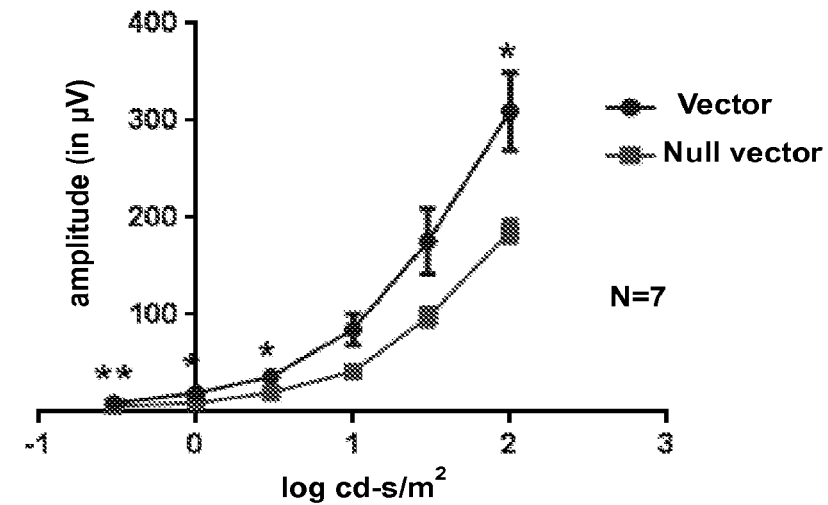

Two week old Rd16/NrlKO mice were administrated 5e8 to 2e9 vg AAV CEP290 myosin tail fragment vector unilaterally through subretinal injection (FIG. 3a shows 5e8 vg/eye dose; FIG. 3b shows 1e9 vg/eye dose; FIG. 3c shows 2e9 vg/eye dose). The control eyes were injected with equal dose of viral particle with no expression cassette (null vector). These mice were followed by photopic ERG 1 month after injection. These data demonstrate that the vector containing the Myosin-tail CEP290 protein fragment was effective following administration at all doses spanning 5e8 to 2e9 vg AAV vector.

Figure 4A:
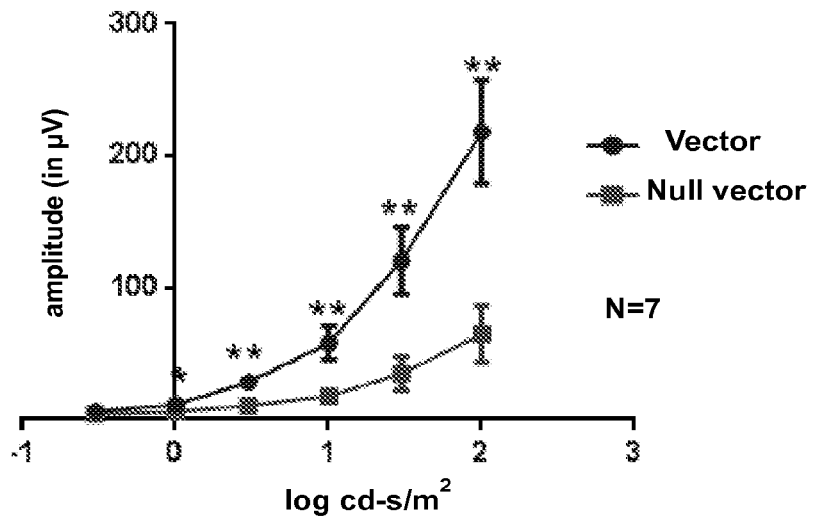
FIGS. 4a, 4b, and 4c show electroretinogram (ERG) data monitoring the therapeutic effect of administration of the Myosin Tail fragment at one month (FIG. 4a), four months (FIG. 4b), and eight months (FIG. 4c) after vector administration.
Figure 4B:
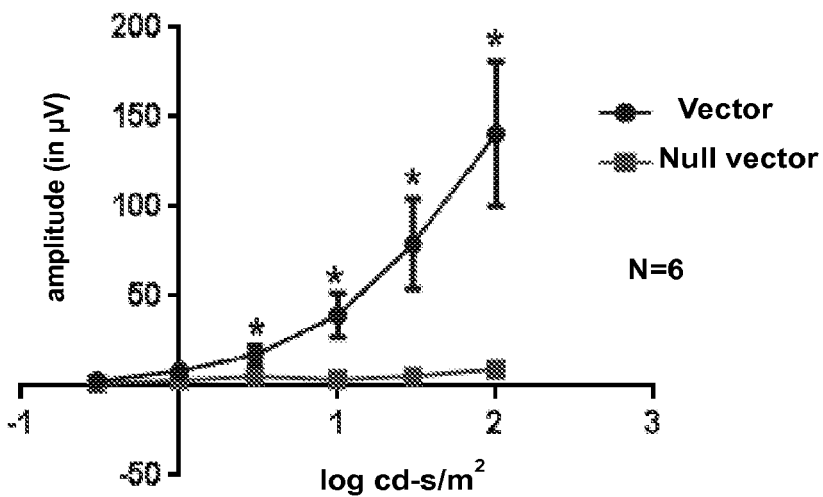
Figure 4C:
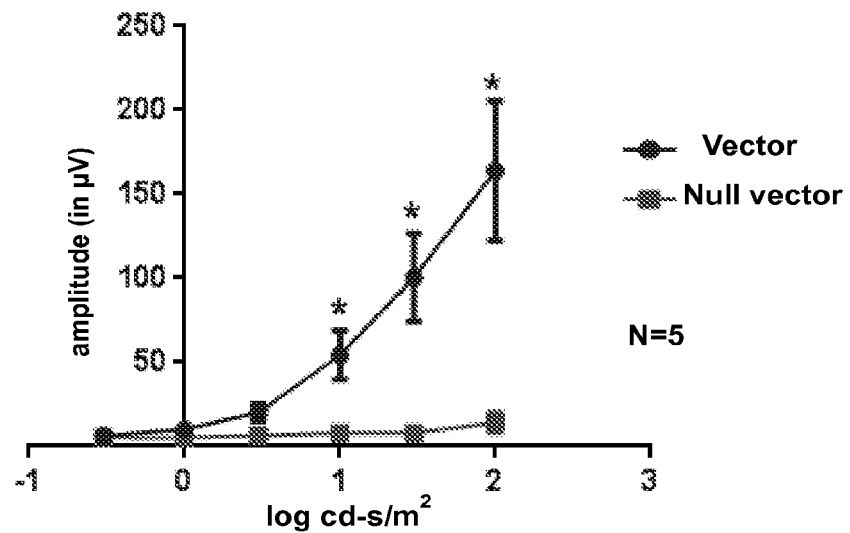

Example 3: Long-Term Therapeutic Effect of Administration of the Myosin-Tail Fragment Vector Two week old Rd16/Nrl knockout (KO) mice were administered 1e9 vg AAV myosin tail CEP290 fragment vector unilaterally through subretinal injection. The control eyes were injected with an equal dose of viral particle with no expression cassette (null vector). These mice were followed by photopic ERG for 8 months after injection. FIG. 4a shows the results of vector administration one month post administration, FIG. 4b shows the results of vector administration at four months post administration, and FIG. 4c shows the results of vector administration at eight months post administration. These data demonstrate that administration of the vector containing the Myosin-tail CEP290 protein fragment was effectively expressed for many months following an initial administration.

Figure 5:
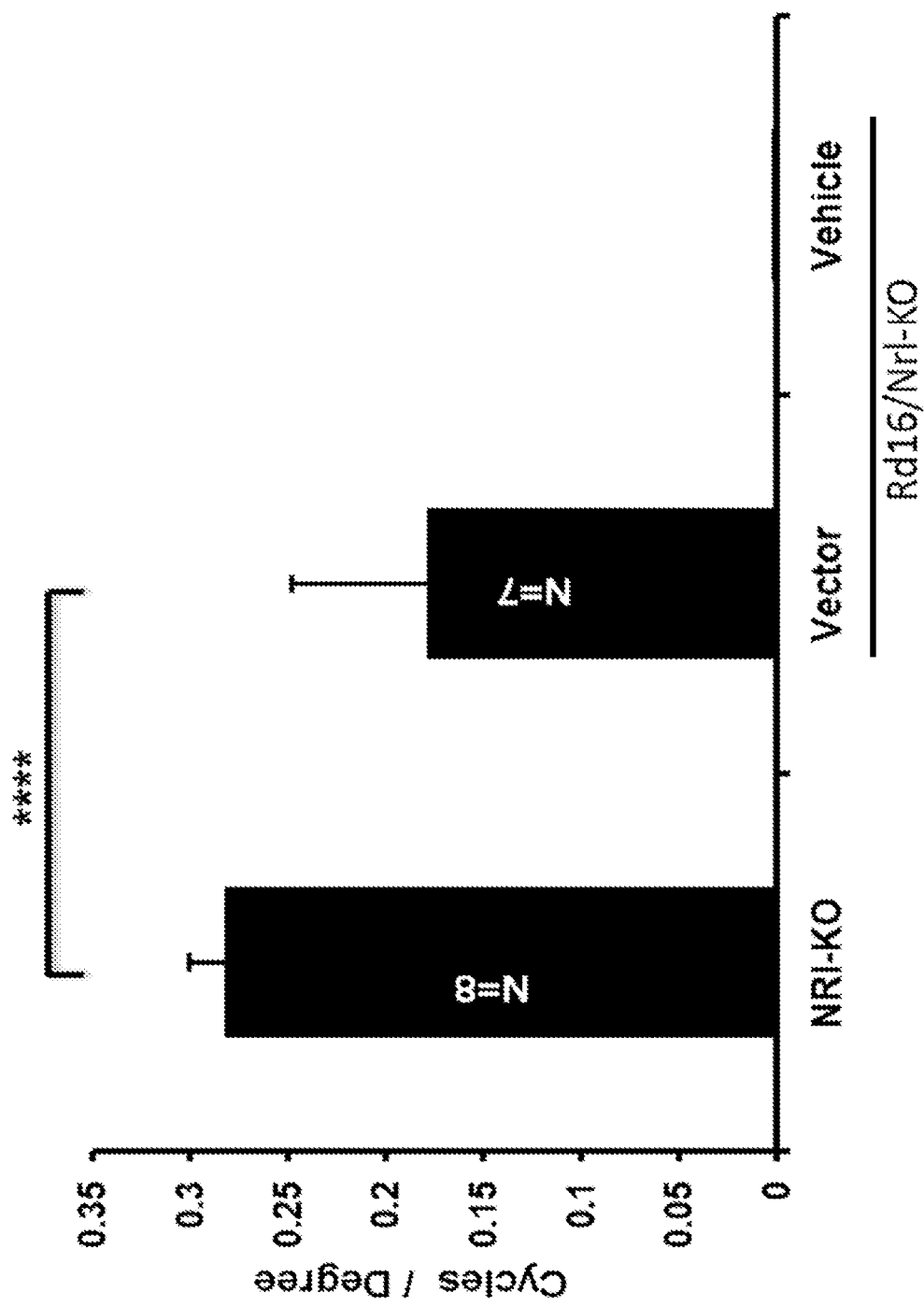
FIG. 5 shows the results of photopic optomotor testing of mice following administration of CEP290 protein fragment vector of this disclosure.

Example 4: Improved Visual Behavior Following Myosin-Tail CEP290 Protein Fragment Vector Treatment FIG. 5 shows the results of photopic optomoter testing of three-week old Rd16/NrlKO mice administered 8e8 vg myosin tail CEP290 fragment vector unilaterally through subretinal injection. The control eyes were injected with equal volume of vehicle. The photopic optomotor tests were administered to these mice at 3 months of age. Nrl-KO mice with all cone retina were used as positive controls. These data demonstrate the significant increase in visual function lasting at least three months in these test animals following administration of a vector encoding a CEP290 protein fragment of this disclosure.

Figure 6:
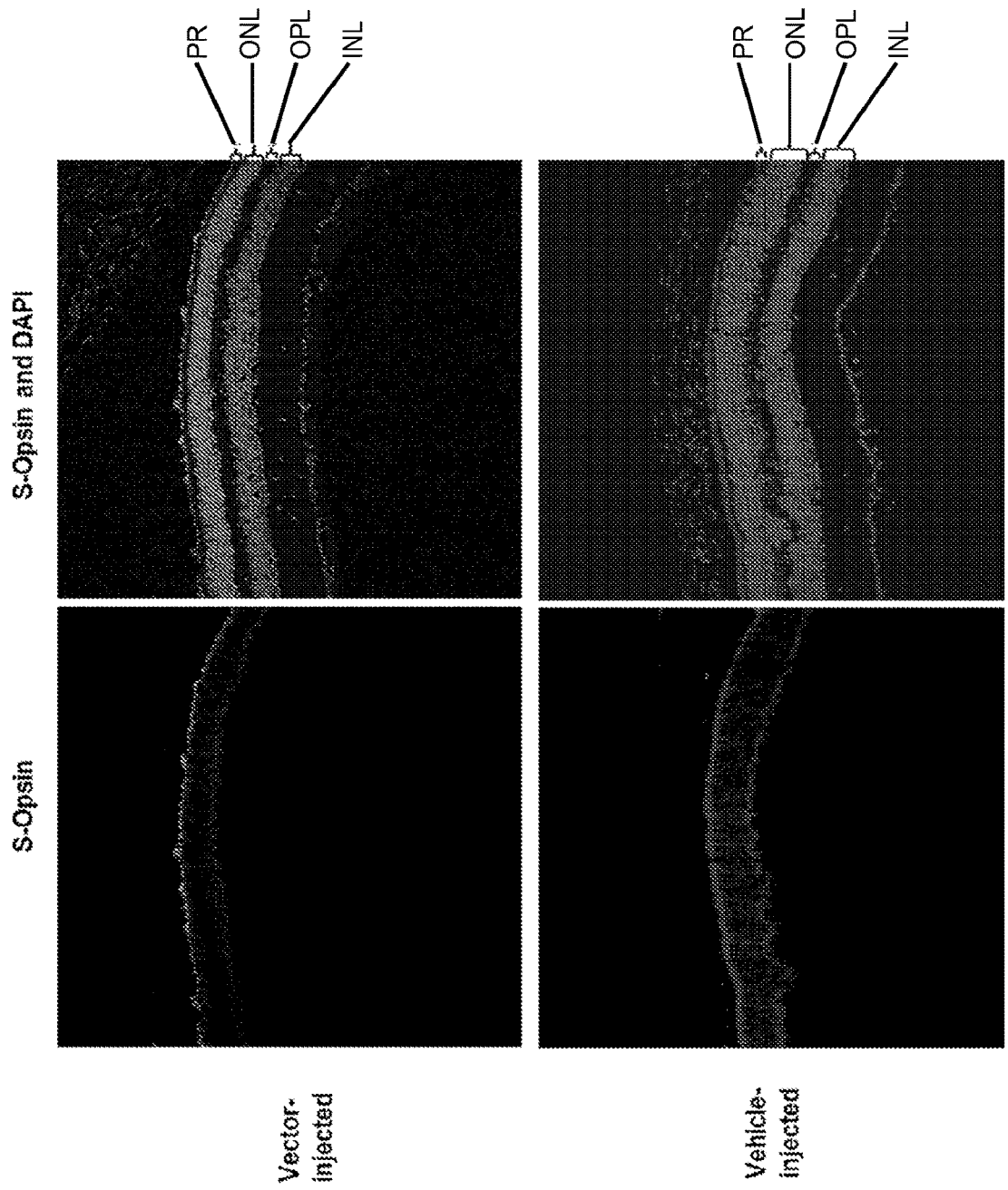
FIG. 6 shows immunohistochemistry data showing corrected s-opsin mislocalization along with higher s-opsin expression in the retina of mice treated with vector particles containing CEP290 protein fragment constructs of this disclosure.

Example 5: Correction of s-Opsin Mislocalization and Higher s-Opsin Expression in Vector Treated Retinas Two week old RD16/NRL KO mice were administered $2 \times 10^9$ AAV vector particles unilaterally through subretinal injection. Control eyes were injected with vehicle. These mice were euthanized four months after injection and their eyes are analyzed by immunohistochemistry (IHC) (FIG. 6). In the vehicle-treated eyes, s-opsin was mislocalized to photoreceptor cell bodies and synaptic terminals. These data demonstrate that vector-treated eye showed corrected s-opsin localization (outer-segments) and a higher s-opsin expression. In FIG. 6, PR: photoreceptor; ONL: outer nuclear layer; OPL; Outer plexiform layer, INL: inner nuclear layer: s-opsin staining appears in PR in all four IHC images; s-opsin also appears in OPL in vehicle-injected IHC images.

What is claimed is:

1. A method of treating CEP290-related Leber Congenital Amaurosis in an individual in need thereof, comprising administering an effective amount of a vector comprising a deoxyribonucleic acid (DNA) molecule comprising a nucleotide sequence that encodes a protein consisting of the amino acid sequence of SEQ ID NO:11, to the individual in need thereof, wherein the protein consisting of the amino acid sequence of SEQ ID NO:11 increases visual function of the individual when expressed in photoreceptor cells.

2. The method of claim 1, wherein the vector is delivered as naked DNA.

3. The method of claim 1, wherein the vector is delivered as a viral particle.

4. The method of claim 1, wherein the vector is administered into an eye by an injection method selected from subconjunctival, sub-Tenon's, intravitreal, subretinal, and intracameral injection.

5. The method of claim 1, wherein the vector is administered in a dosage of between $3e^8$ nucleic acid molecules per eye (nams/eye) and $1e^{13}$ nams/eye.

6. The method of claim 1, wherein the nucleotide sequence that encodes the protein of SEQ ID NO:11 consists of the nucleotide sequence of SEQ ID NO:10.

7. The method of claim 1, wherein the vector is an adeno-associated virus (AAV) vector.

8. The method of claim 7, wherein the AAV vector is an AAV8 vector.

9. The method of claim 1, wherein the vector further comprises a promoter sequence functionally linked to the nucleotide sequence to cause expression of the protein consisting of the amino acid sequence of SEQ ID NO: 11, selected from the group consisting of a rhodopsin promoter, a rhodopsin kinase promoter, an Interstitial retinol-binding protein (IRBP promoter), a cytomegalovirus (CMV) promoter, and a CMV intermediate-early (IE) promoter.

10. The method of claim 1, wherein the vector further comprises at least one inverted terminal repeat (ITR) nucleotide sequence that comprises an AAV Rep binding site (RBS) and a terminal resolution site (trs) sequence.

11. The method of claim 10, wherein the at least one ITR comprises an ITR from an AAV2 virus.

\* \* \* \* \*